US010914747B2

(12) United States Patent
Sexton et al.

(10) Patent No.: US 10,914,747 B2
(45) Date of Patent: Feb. 9, 2021

(54) IMMUNOASSAY TO DETECT CLEAVED HIGH MOLECULAR WEIGHT KININOGEN

(71) Applicant: Dyax Corp., Lexington, MA (US)

(72) Inventors: Daniel J. Sexton, Melrose, MA (US); Ryan Faucette, Melrose, MA (US); Janja Cosic, Arlington, MA (US)

(73) Assignee: Dyax Corp., Lexington, MA (US)

( * ) Notice: Subject to any disclaimer, the term of this patent is extended or adjusted under 35 U.S.C. 154(b) by 0 days.

(21) Appl. No.: 15/769,237

(22) PCT Filed: Oct. 19, 2016

(86) PCT No.: PCT/US2016/057640
§ 371 (c)(1),
(2) Date: Apr. 18, 2018

(87) PCT Pub. No.: WO2017/070170
PCT Pub. Date: Apr. 27, 2017

(65) Prior Publication Data
US 2018/0306807 A1 Oct. 25, 2018

Related U.S. Application Data

(60) Provisional application No. 62/335,311, filed on May 12, 2016, provisional application No. 62/243,505, filed on Oct. 19, 2015.

(51) Int. Cl.
*G01N 33/86* (2006.01)
*C07K 16/36* (2006.01)
(Continued)

(52) U.S. Cl.
CPC ......... *G01N 33/6893* (2013.01); *C07K 16/36* (2013.01); *G01N 33/54306* (2013.01);
(Continued)

(58) Field of Classification Search
CPC ......... G01N 33/6893; G01N 33/54306; G01N 33/743; G01N 33/53; G01N 33/58;
(Continued)

(56) References Cited

U.S. PATENT DOCUMENTS 4,882,272 A 11/1989 Scott et al.
4,908,431 A 3/1990 Colman et al.
(Continued)

FOREIGN PATENT DOCUMENTS

CN 102405228 A 4/2012
CN 102762203 A2 10/2012
(Continued)

OTHER PUBLICATIONS

Berrettini et al., Detection of in vitro and in vivo cleavage of high molecular weight kininogen in human plasma by immunoblotting with monoclonal antibodies. Blood. Aug. 1986;68(2):455-62.
(Continued)

*Primary Examiner* — Gailene Gabel
(74) *Attorney, Agent, or Firm* — Wolf, Greenfield & Sacks, P.C.

(57) ABSTRACT

The present disclosure provides immunoassay methods of detecting a cleaved high molecular weight kininogen (HMWK) with high sensitivity and specificity and isolated antibodies that specifically bind cleaved HMWK.

50 Claims, 24 Drawing Sheets

Specification includes a Sequence Listing.

(51) Int. Cl.
*G01N 33/68* (2006.01)
*G01N 33/543* (2006.01)

(52) U.S. Cl.
CPC ....... *G01N 33/86* (2013.01); *G01N 2333/745* (2013.01); *G01N 2800/50* (2013.01)

(58) Field of Classification Search
CPC ............... G01N 33/6854; G01N 33/86; G01N 2333/745; G01N 2800/50; C07K 16/36; C07K 2317/70; A61P 7/10
See application file for complete search history.

(56) References Cited

U.S. PATENT DOCUMENTS

| | | | |
|---|---|---|---|
| 4,985,354 | A | 1/1991 | Toyomaki et al. |
| 5,025,796 | A | 6/1991 | Hargreaves et al. |
| 5,047,323 | A | 9/1991 | Colman et al. |
| 5,472,945 | A | 12/1995 | Schmaier et al. |
| 6,242,210 | B1 | 6/2001 | Bjoerck et al. |
| 6,913,900 | B2 | 7/2005 | Kaplan et al. |
| 10,101,344 | B2 | 10/2018 | Sexton et al. |
| 10,648,990 | B2 | 5/2020 | Sexton et al. |
| 2005/0223416 | A1 | 10/2005 | Nuijens et al. |
| 2006/0069020 | A1 | 3/2006 | Blair et al. |
| 2007/0192882 | A1 | 8/2007 | Dewald |
| 2008/0038276 | A1 | 2/2008 | Sinha et al. |
| 2008/0299549 | A1 | 12/2008 | Sorge et al. |
| 2009/0075887 | A1 | 3/2009 | McPherson |
| 2011/0154517 | A1 | 6/2011 | Dewald |
| 2011/0200611 | A1 | 8/2011 | Sexton |
| 2011/0212104 | A1 | 9/2011 | Beaumont et al. |
| 2011/0318359 | A1 | 12/2011 | Feener et al. |
| 2012/0201756 | A1 | 8/2012 | Sexton |
| 2013/0156753 | A1 | 6/2013 | Jin |
| 2014/0128436 | A1 | 5/2014 | Sinha et al. |
| 2015/0362493 | A1* | 12/2015 | Sexton .................. C07K 16/40 424/142.1 |
| 2016/0252527 | A1 | 9/2016 | Sexton et al. |
| 2016/0252533 | A1 | 9/2016 | Sexton et al. |
| 2019/0120862 | A1 | 4/2019 | Sexton et al. |

FOREIGN PATENT DOCUMENTS

| | | | | |
|---|---|---|---|---|
| EP | 0 210 029 | A2 | 1/1987 | |
| JP | S63-185398 | A | 7/1988 | |
| WO | WO 2006/101387 | A2 | 9/2006 | |
| WO | WO 2007/079096 | A2 | 7/2007 | |
| WO | WO 2011/075684 | A1 | 6/2011 | |
| WO | WO 2012/094587 | A1 | 7/2012 | |
| WO | WO 2012/170945 | A2 | 12/2012 | |
| WO | WO 2012/170947 | A2 | 12/2012 | |
| WO | WO 2014/113712 | A1 * | 7/2014 | ............. C07K 16/40 |
| WO | WO 2015/061182 | A1 | 4/2015 | |
| WO | WO 2015/061183 | A1 | 4/2015 | |

OTHER PUBLICATIONS

[No Author Listed], Image Studio Software Compatible with Mac® Systems Now Available from LI-COR!. BioB Blog. May 8, 2012:1-3.

[No Author Listed], Mouse High Molecular Weight Kininogen (HMWK) ELISA Kit (Cat. No. MBS089195). MyBiosource Datasheet. Jan. 2, 1984. Retrieved from <https://www.mybiosource.com/prods/ELIS-A-Kit/Mouse/High-Molecular-Weight-Kinogen/HMWK/datasheet.php?products_id=89195> on Dec. 13, 2018. 4 pages.

Blais et al., The kallikrein-kininogen-kinin system: lessons from the quantification of endogenous kinins. Peptides. Dec. 2000;21(12):1903-40. Review.

Bühler et al., Improved detection of proteolytically cleaved high molecular weight kininogen by immunoblotting using an antiserum against its reduced 47 kDa light chain. Blood Coagul Fibrinolysis. May 1995;6(3):223-32.

Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.

Colman et al., Studies on the prekallikrein (kallikreinogen)—kallikrein enzyme system of human plasma. I. Isolation and purification of plasma kallikreins. J Clin Invest. Jan. 1969;48(1):11-22.

Cugno et al., Activation of factor XII and cleavage of high molecular weight kininogen during acute attacks in hereditary and acquired C1-inhibitor deficiencies. Immunopharmacology. Jun. 1996;33(1-3):361-4.

Cugno et al., Activation of the coagulation cascade in C1-inhibitor deficiencies. Blood. May 1, 1997;89(9):3213-8.

Cugno et al., Activation of the contact system and fibrinolysis in autoimmune acquired angioedema: A rationale for prophylactic use of tranexamic acid. J Allergy Clin Immunol. 1994;93(5):870-876.

Defendi et al., Enzymatic assays for the diagnosis of bradykinin-dependent angioedema. PLoS One. Aug. 5, 2013;8(8):e70140. doi:10.1371/journal.pone.0070140. Print 2013. Erratum in: PLoS One. 2014;9(6):e100345.

Devani et al., Kallikrein-kinin system activation in Crohn's disease: differences in intestinal and systemic markers. Am J Gastroenterol. Aug. 2002;97(8):2026-32.

Dobó et al., Cleavage of kininogen and subsequent bradykinin release by the complement component: mannose-binding lectin-associated serine protease (MASP)-1. PLoS One. 2011;6(5):e20036. doi: 10.1371/journal.pone.0020036. Epub May 23, 2011.

Faucette et al., A Biomarker Assay for the Detection of Contact System Activation. Blood. 2013;122:2347. Available online at http://www.bloodjournal.org/conten/122/21/2347. Last accessed on Mar. 30, 2018. Abstract only.

Gallimore et al., Plasma levels of factor XII, prekallikrein and high molecular weight kininogen in normal blood donors and patients having suffered venous thrombosis. Thromb Res. 2004;114(2):91-6.

Ishiguro et al., Mapping of functional domains of human high molecular weight and low molecular weight kininogens using murine monoclonal antibodies. Biochemistry. Nov. 3, 1987;26(22):7021-9.

Isordia-Salas et al., The mutation Ser511Asn leads to N-glycosylation and increases the cleavage of high molecular weight kininogen in rats genetically susceptible to inflammation. Blood. Oct. 15, 2003;102(8):2835-42. Epub Jul. 3, 2003.

Isordia-Salas et al., The role of plasma high molecular weight kininogen in experimental intestinal and systemic inflammation. Arch Med Res. Jan.-Feb. 2005;36(1):87-95.

Joseph et al., Studies of the mechanisms of bradykinin generation in hereditary angioedema plasma. Ann Allergy Asthma Immunol. Sep. 2008;101(3):279-86. doi: 10.1016/S1081-1206(10)60493-0.

Katori et al., Evidence for the involvement of a plasma kallikrein-kinin system in the immediate hypotension produced by endotoxin in anaesthetized rats. Br J Pharmacol. Dec. 1989;98(4):1383-91.

Kerbiriou-Nabias et al., Radioimmunoassays of human high and low molecular weight kininogens in plasmas and platelets. Br J Haematol. Feb. 1984;56(2):273-86.

Khan et al., High-molecular-weight kininogen fragments stimulate the secretion of cytokines and chemokines through uPAR, Mac-1, and gC1qR in monocytes. Arterioscler Thromb Vasc Biol. Oct. 2006;26(10):2260-6. Epub Aug. 10, 2006. Erratum in: Arterioscler Thromb Vasc Biol. Nov. 2006;26(11):e146.

Ladner et al., Discovery of Ecallantide: A Potent and Selective Inhibitor of Plasma Kallikrein. J Allergy and Clinical Immunol. Jan. 1, 2007;119(1):S312.

Merlo et al., Elevated levels of plasma prekallikrein, high molecular weight kininogen and factor XI in coronary heart disease. Atherosclerosis. Apr. 2002;161(2):261-7.

Nguyen et al., The Simple Western™: a gel-free, blot-free, hands-free Western blotting reinvention. Nature Methods. Oct. 28, 2011;8:5-6.

Nielsen et al., Hereditary angio-oedema: new clinical observations and autoimmune screening, complement and kallikrein-kinin analyses. J Intern Med. Feb. 1996;239(2):119-30.

Page et al., An autoantibody to human plasma prekallikrein blocks activation of the contact system. Br J Haematol. May 1994;87(1):81-6.

(56) References Cited

OTHER PUBLICATIONS

Phipps et al., Plasma kallikrein mediates angiotensin II type 1 receptor-stimulated retinal vascular permeability. Hypertension. Feb. 2009;53(2):175-81. Epub Jan. 5, 2009.
Raymond et al., Quantification of des-Arg$^9$-bradykinin using a chemiluminescence enzyme immunoassay: application to its kinetic profile during plasma activation. J Immunol Methods. Mar. 27, 1995;180(2):247-57.
Reddigari et al., Cleavage of human high-molecular weight kininogen by purified kallikreins and upon contact activation of plasma. Blood. May 1988;71(5):1334-40.
Reddigari et al., Monoclonal antibody to human high-molecular-weight kininogen recognizes its prekallikrein binding site and inhibits its coagulant activity. Blood. Aug. 1, 1989;74(2):695-702.
Reddigari et al., Quantification of human high molecular weight kininogen by immunoblotting with a monoclonal anti-light chain antibody. J Immunol Methods. Apr. 21, 1989;119(1):19-25.
Schmaier et al., Determination of the bifunctional properties of high molecular weight kininogen by studies with monoclonal antibodies directed to each of its chains. J Biol Chem. Jan. 25, 1987;262(3):1405-11.
Schousboe et al., High molecular weight kininogen binds to laminin—characterization and kinetic analysis. FEBS J. Sep. 2009;276(18):5228-38. doi: 10.1111/j.1742-4658.2009.07218.x. Epub Aug. 19, 2009.
Scott et al., A new assay for high molecular weight kininogen in human plasma using a chromogenic substrate. Thromb Res. Dec. 15, 1987;48(6):685-700.
Scott et al., Sensitive antigenic determinations of high molecular weight kininogen performed by covalent coupling of capture antibody. J Lab Clin Med. Jan. 1992;119(1):77-86. Abstract only.
Sexton et al., Discovery and Characterization of a Fully Human Monoclonal Antibody Inhibitor of Plasma Kallikrein for the Treatment of Plasma Kallikrein-Mediated Edema. J. Allergy Clin. Immunol. Feb. 2013;131(2):AB32.
Syvänen et al., A radioimmunoassay for the detection of molecular forms of human plasma kininogen. FEBS Lett. Jul. 6, 1981;129(2):241-5.
Torzewski et al., Animal Models of c-Reactive Protein. Hindawi Publishing Corpl, Mediators of Inflammation. 2014:1-7.
Uchida et al., Differential assay method for high molecular weight and low molecular weight kininogens. Thromb Res. 1979;15(1-2):127-34.
Van Der Vekens et al., Human and equine cardiovascular endocrinology: beware to compare. Cardiovascular Endocrinology. 2013;2(4):67-76.
Veloso et al., A monoclonal anti-human plasma prekallikrein antibody that inhibits activation of prekallikrein by factor XIIa on a surface. Blood. Oct. 1987;70(4):1053-62.

Williams et al., DX-88 and HAE: a developmental perspective. Transfus Apher Sci. Dec. 2003;29(3):255-8.
Zhang et al., Two-chain high molecular weight kininogen induces endothelial cell apoptosis and inhibits angiogenesis: partial activity within domain 5. FASEB J. Dec. 2000;14(15):2589-600.
U.S. Appl. No. 15/030,790, filed Apr. 20, 2016, Sexton et al.
U.S. Appl. No. 16/131,781, filed Sep. 14, 2018, Sexton et al.
U.S. Appl. No. 14/761,690, filed Jul. 17, 2015, Sexton et al.
U.S. Appl. No. 15/030,811, filed Apr. 20, 2016, Sexton et al.
EP 14855002.3, Feb. 20, 2017, Supplementary European Search Report.
PCT/US2014/061242, Feb. 3, 2015, International Search Report and Written Opinion.
PCT/US2014/061242, May 6, 2016, International Preliminary Report on Patentability.
EP 14740444.6, Jun. 17, 2016, Extended European Search Report.
EP 18186356.4, Jan. 18, 2019, Extended European Search Report.
PCT/US2014/012107, Apr. 14, 2014, International Search Report and Written Opinion.
PCT/US2014/012107, Jul. 30, 2015, International Preliminary Report on Patentability.
EP 14856778.7, Feb. 28, 2017, Supplementary Partial European Search Report.
EP 14856778.7, Jun. 16, 2017, Supplementary European Search Report.
PCT/US2014/061247, Feb. 4, 2015, International Search Report and Written Opinion.
PCT/US2014/061247, May 6, 2016, International Preliminary Report on Patentability.
PCT/US2016/057640, Jan. 26, 2017, International Search Report and Written Opinion.
PCT/US2016/057640, May 3, 2018, International Preliminary Report on Patentability.
U.S. Appl. No. 16/849,492, filed Apr. 14, 2020, Sexton et al.
Chaudhuri et al., Glucocorticoids and rheumatoid arthritis—a reappraisal. I. J. Rheumatol. Mar. 1, 2008;3(1):21-8.
Huang, Alzheimer Disease. Merck Manual, Professional Version. Dec. 2019:1-7.
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kontzias, Rheumatoid Arthritis (RA). Merck Manual, Professional Version. Dec. 2018:1-19.
Maggio, Sepsis and Septic Shock. Merck Manual, Professional Version. Jan. 2020:1-8.
Mehta, Diabetic Retinopathy. Merck Manual, Professional Version. Jun. 2019:1-5.

* cited by examiner

A

B

A

B

A

B

C

D

A

B

C

D

A

B

C

D

A

B

C

D

IMMUNOASSAY TO DETECT CLEAVED HIGH MOLECULAR WEIGHT KININOGEN

CROSS REFERENCE TO RELATED APPLICATIONS

This application is a national stage filing under 35 U.S.C. 371 of International Patent Application Serial No. PCT/US2016/057640, filed Oct. 19, 2016, entitled "IMMUNOASSAY TO DETECT CLEAVED HIGH MOLECULAR WEIGHT KININOGEN", which claims the benefit of U.S. Provisional Application Ser. No. 62/243,505, filed Oct. 19, 2015, and 62/335,311, filed May 12, 2016 under 35 U.S.C. § 119, the entire content of each of which is herein incorporated by reference.

BACKGROUND OF PRESENT DISCLOSURE

Kininogens are precursors of kinin, such as bradykinin and kallidin. There are two types of human kininogens, high molecular-weight kininogen (HMWK) and low molecular-weight kininogen (LMWK), which are splicing variants. HMWK acts mainly as a cofactor on coagulation and inflammation and is the preferred substrate for plasma kallikrein (pKal)-mediated bradykinin generation.

Plasma kallikrein (pKal) is the primary bradykinin-generating enzyme in the circulation. The activation of pKal occurs via the contact system which has been linked to disease pathology associated with hereditary angioedema (HAE). pKal cleaves HMWK (a single-chain polypeptide) to produce bradykinin and a cleaved form HMWK, which contains two polypeptide chains held together by a disulfide bond. Cugno et al., Blood (1997) 89:3213-3218.

Cleaved HMWK increased to about 47% of total kininogen during a hereditary angioedema (HAE) attack. Cugno et al., Blood (1997) 89:3213-3218, making it a biomarker for monitoring HAE attack. It is therefore of interest to develop sensitive and reliable assays for detecting the level of cleaved HMWK in biological samples.

SUMMARY OF PRESENT DISCLOSURE

Some aspects of the present disclosure provide an immunoassay for detecting a cleaved high molecular weight kininogen (HMWK) with high sensitivity and specificity. The method comprises (i) providing a support member on which a first agent (e.g., an antibody such as 559B-M004-B04) that specifically binds a cleaved HMWK is attached; (ii) contacting the support member of (i) with a biological sample suspected of containing a cleaved HMWK; (iii) contacting the support member obtained in (ii) with a second agent that binds HMWK, wherein the second agent is conjugated to a label; and (iv) detecting a signal released from the label of the second agent that is bound to the support member, directly or indirectly, to determine the level of the cleaved HMWK in the biological sample. In some instances, step (ii) may be performed in the presence of $ZnCl_2$.

In some embodiments, prior to step (ii), the support member of (i) is incubated with a blocking buffer.

In some embodiments, the second agent is a polyclonal antibody, a monoclonal antibodies, or a mixture of two or more monoclonal antibodies that bind to HMWK. The two or more monoclonal antibodies in the mixture may bind to different epitopes in HMWK. In some embodiments, the label is a signal releasing agent. In some embodiments, the label is a member of a receptor-ligand pair. In that case, the immunoassay may further comprise, prior to step (iv), contacting the second agent in (iii), which is immobilized on the support member, with the other member of the receptor-ligand pair, wherein the other member is conjugated to a signal releasing agent. In one example, the receptor-ligand pair is biotin and streptavidin.

Another aspect of the present disclosure provides methods for detecting a cleaved high molecular kininogen (HMWK) in a sample, the method comprising (i) contacting a sample suspected of containing a cleaved HMWK with any of the antibodies described herein (e.g. 559B-M004-B04); (ii) measuring a complex of the cleaved HMWK and the antibody formed in step (i); and (iii) determining the level of the cleaved HMWK in the sample based on the result of step (ii). In some embodiments, step (i) is performed in the presence of $ZnCl_2$. In some embodiments, step (i) is performed using an enzyme-linked immunosorbent assay (ELISA) or an immunoblotting assay.

In any of the methods described herein, the sample may be a biological sample obtained from a subject (e.g., a human patient), such as a serum sample of a plasma sample. In some embodiments, the method further comprises collecting the sample into an evacuated blood collection tube, which comprises one or more protease inhibitors.

Any of the assay methods (e.g., immunoassays) described herein may be a ELISA assay, a Western blot assay, or lateral flow assay.

In some embodiments, the biological sample is obtained from a subject (e.g., a human patient) having a disease. The assay method may further comprise determining whether the disease is mediated by plasma kallikrein based on the level of the cleaved HMWK, a deviation of the level of the cleaved HMWK in the sample from that of a control sample being indicative that the disease is mediated by plasma kallikrein.

Any of the assay methods described herein may further comprise identifying patients with diseases or disorders mediated by plasma kallikrein, or evaluating the efficacy of a treatment of the disease or disorder based on the levels of cleaved HMWK. In some embodiments, the method may further comprises administering to the subject an effective amount of a therapeutic agent, such as a plasma kallikrein (pKal) inhibitor, a bradykinin 2 receptor (B2R) inhibitor, and/or a C1 esterase inhibitor, for treating the disorder, if the subject is identified as having the disorder. In some embodiments the pKal inhibitor is an anti-pKal antibody. In some embodiments, the therapeutic agent is lanadelumab, ecallantide, icatibant, or human plasma-derived C1 esterase inhibitor.

In some embodiments, the subject is a human patient who is on a treatment for the disorder, and wherein the method further comprises assessing the efficacy of the treatment based on the level of the cleaved HMWK determining in step (iii), a deviation of the level of the cleaved HMWK in the sample from the subject from that of a control sample being indicative of the treatment efficacy. In some embodiments, the method further comprises identifying a suitable treatment for the subject based on the level of the cleaved HMWK. In some embodiments, the method further comprises identifying the subject as a candidate for a treatment of the disease based on the level of the cleaved HMWK.

In some embodiments, the human patient has a history of the disease (e.g., HAE). In some embodiments, the method further comprises assessing the risk of disease attack in the subject based on the level of the cleaved HMWK, a deviation of the level of the cleaved HMWK in the sample from the subject from that of a control sample being indicative of the risk of disease attack. In some embodiments, the method further comprises administering a therapeutic agent to the subject, if the subject is at risk of disease attack.

In another aspect, a kit is provided for detecting a cleaved high molecular weight kininogen (HMWK), the kit comprising a first agent (e.g., an antibody as described herein) that specifically binds a cleaved HMWK. In some embodiments, the kit further comprises a second agent that binds HMWK, a support member, or both, and optionally instructions for detecting the cleaved HMWK. In some examples, the support member is a 96-well plate.

In another aspect of the disclosure, an isolated antibody is provided, which specifically binds a cleaved high molecular weight kininogen (HMWK). In some embodiments, the antibody binds the same epitope as 559B-M004-B04 or competes against 559B-M004-B04 for binding to the cleaved HMWK. In some embodiments, the antibody comprises the same heavy chain and light chain complementary determining regions as 559B-M004-B04, e.g., the same heavy chain and light variable regions as 559B-M004-B04. In one example, the antibody is 559B-M004-B04.

Any of the antibodies specific to a cleaved HMWK as described herein can be used in a method for detecting a cleaved high molecular kininogen (HMWK) in a sample. Such a method may comprise (i) contacting a sample suspected of containing a cleaved HMWK with the antibody; (ii) measuring a complex of the cleaved HMWK and the antibody formed in step (i); and determining the level of the cleaved HMWK in the sample based on the result of step (ii). In some embodiments, the sample is a biological sample such as a serum sample or a plasma sample obtained from a human subject. The result obtained from this method may be relied on to determine the risk of a subject from whom the sample is obtained for developing a disorder mediated by plasma kallikrein such as HAE. In some instances, step (i) can be performed in the presence of $ZnCl_2$.

Any of the immunoassay methods described herein can be in Western blot format or ELISA format.

In yet another aspect, an isolated antibody is provided that binds both intact high molecular weight kininogen (HMWK) and a cleaved HMWK.

In some embodiments, the antibody that binds both intact and cleaved HMWK does not bind to low molecular weight kininogen (LMWK). In some embodiments, the antibody binds the same epitope as 559B-M0067-E02, 559B-M0039-G07, 559B-M0044-E09, 559B-M0003-008, 559B-M0039-H06, 559B-M0039-D08, 559B-M0068-C07, 559B-M0021-G11, 559B-M0061-G06, 559B-M0036-G12, 559B-M0042-E06, 559B-M0070-H10, 559B-M0068-D01, or 559B-M0004-E08. In some embodiments, the antibody competes against 559B-M0067-E02, 559B-M0039-G07, 559B-M0044-E09, 559B-M0003-C08, 559B-M0039-H06, 559B-M0039-D08, 559B-M0068-C07, 559B-M0021-G11, 559B-M0061-G06, 559B-M0036-G12, 559B-M0042-E06, 559B-M0070-H10, 559B-M0068-D01, or 559B-M0004-E08 for binding to the intact HMWK and/or the cleaved HMWK.

In some embodiments, the antibody comprising the same heavy chain and light chain CDRs as 559B-M0067-E02, 559B-M0039-G07, 559B-M0044-E09, 559B-M0003-C08, 559B-M0039-H06, 559B-M0039-D08, 559B-M0068-C07, 559B-M0021-G11, 559B-M0061-G06, 559B-M0036-G12, 559B-M0042-E06, 559B-M0070-H10, 559B-M0068-D01, or 559B-M0004-E08. In some examples, the antibody is selected from the group consisting of 559B-M0067-E02, 559B-M0039-G07, 559B-M0044-E09, 559B-M0003-C08, 559B-M0039-H06, 559B-M0039-D08, 559B-M0068-C07, 559B-M0021-G11, 559B-M0061-G06, 559B-M0036-G12, 559B-M0042-E06, 559B-M0070-H10, 559B-M0068-D01, and 559B-M0004-E08.

In other embodiments, the antibody that binds both intact and cleaved HMWK also binds LMWK. In some embodiments, the antibody binds the same epitope as 559B-M0069-C09, 559B-M0038-F04, 559B-M0044-C05, 559B-M0047-H01, 559B-M0019-E12, 559B-X0004-B05, 559B-M0048-D12, 559B-M0053-G01, 559B-M0038-H03, 559B-M0017-H08, 559B-M0035-F05, 559B-M0035-H09, 559B-M0043-C06, 559B-M0003-A08, 559B-M0054-B11, 559B-M0067-G11, 559B-M0064-H02, or 559B-M0065-B10. In some embodiments, the antibody competes against 559B-M0069-C09, 559B-M0038-F04, 559B-M0044-C05, 559B-M0047-H01, 559B-M0019-E12, 559B-X0004-B05, 559B-M0048-D12, 559B-M0053-G01, 559B-M0038-H03, 559B-M0017-H08, 559B-M0035-F05, 559B-M0035-H09, 559B-M0043-C06, 559B-M0003-A08, 559B-M0054-B11, 559B-M0067-G11, 559B-M0064-H02, or 559B-M0065-B10 for binding to the intact HMWK, the cleaved HMWK, and/or the LMWK.

In some embodiments, the antibody comprises the same heavy chain and light chain CDRs as 559B-M0069-C09, 559B-M0038-F04, 559B-M0044-C05, 559B-M0047-H01, 559B-M0019-E12, 559B-X0004-B05, 559B-M0048-D12, 559B-M0053-G01, 559B-M0038-H03, 559B-M0017-H08, 559B-M0035-F05, 559B-M0035-H09, 559B-M0043-C06, 559B-M0003-A08, 559B-M0054-B11, 559B-M0067-G11, 559B-M0064-H02, or 559B-M0065-B10. In some examples, the antibody is selected from the group consisting of 559B-M0069-C09, 559B-M0038-F04, 559B-M0044-C05, 559B-M0047-H01, 559B-M0019-E12, 559B-X0004-B05, 559B-M0048-D12, 559B-M0053-G01, 559B-M0038-H03, 559B-M0017-H08, 559B-M0035-F05, 559B-M0035-H09, 559B-M0043-C06, 559B-M0003-A08, 559B-M0054-B11, 559B-M0067-G11, 559B-M0064-H02, and 559B-M0065-B10.

The details of one or more embodiments of the disclosure are set forth in the description below. Other features or advantages of the present disclosure will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

A: plots the ratio of the result of a 2-chain HWMK binding assay to a LMWK binding assay on the y-axis compared to the ratio of the result of a 2-chain HMWK binding assay to a 1-chain HMWK binding assay on the x-axis for each antibody (Fab) tested. Recombinant Fab fragments were passively immobilized onto 384-well plates prior to addition of biotinylated 2-chain HMWK, 1-chain HMWK, or LMWK, followed by streptavidin-HRP. B: shows binding to 1-chain HMWK, 2-chain HMWK, or LMWK for the indicated isolated Fab fragments.

Figure 15:
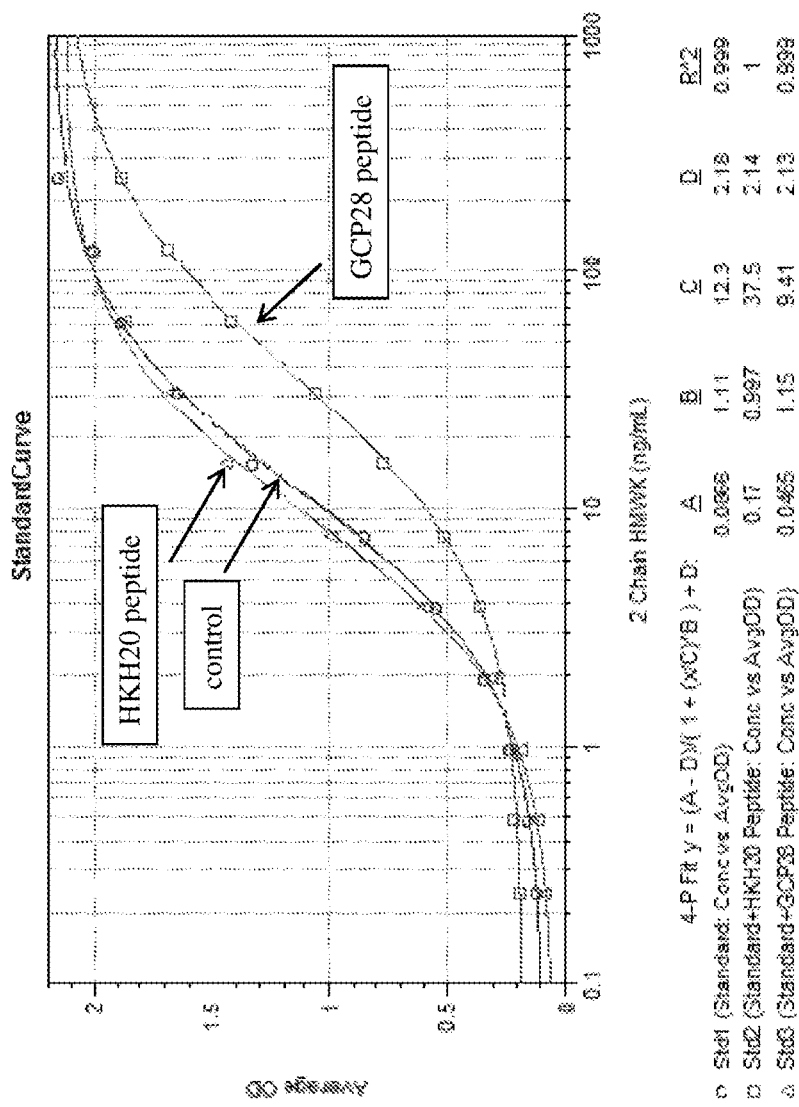

FIG. 15 is a graph showing competition of 2-chain HMWK and kininogen peptides (HKH20 and GCP28) for binding to 559B-M0004-B04.

Figure 16:
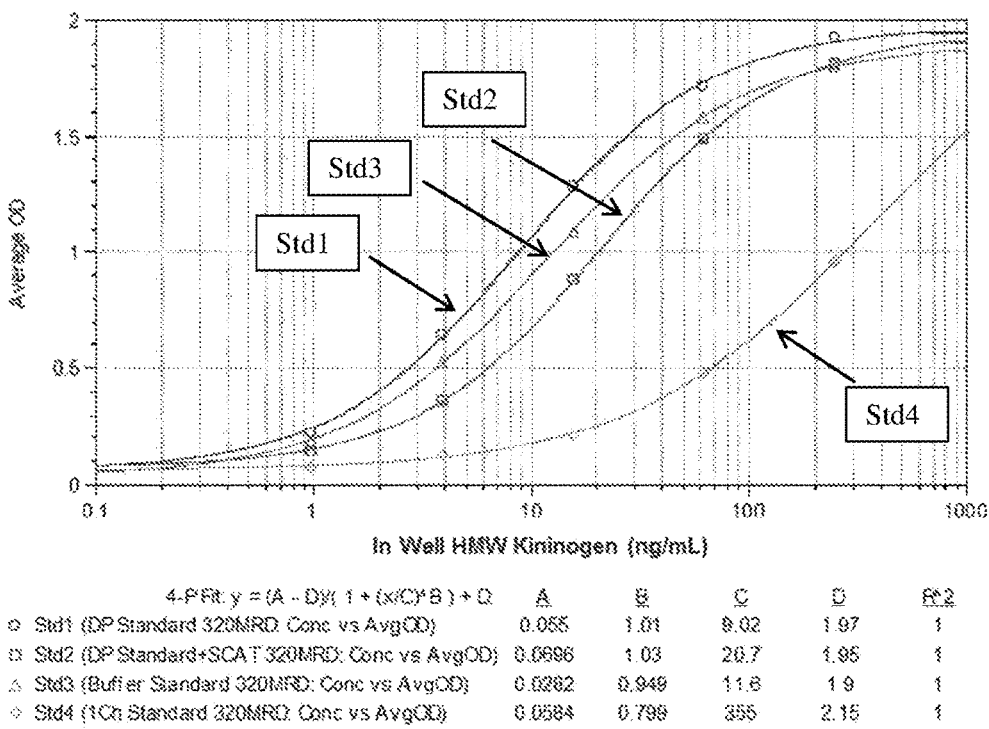

FIG. 16 is a graph showing a standard curve for an optimized sandwich ELISA for the detection of 2-chain HMWK in human plasma samples.

Figure 17:
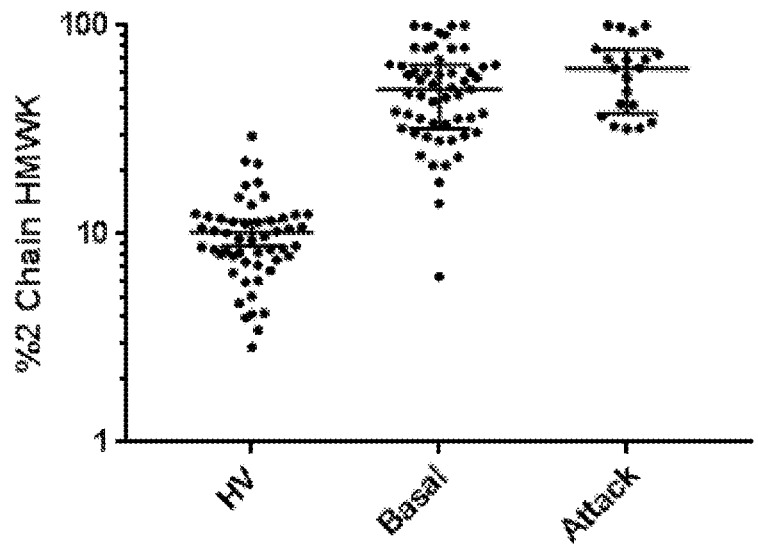
Figure 17:
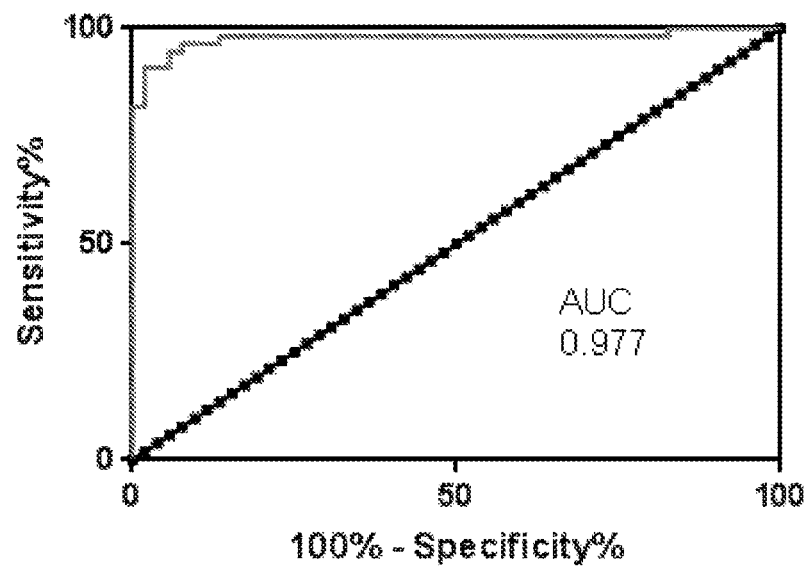
Figure 17:
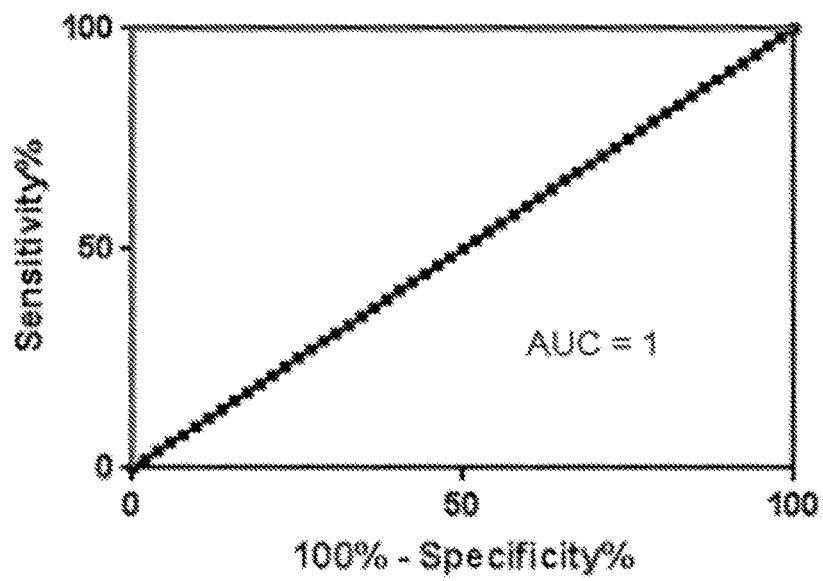
Figure 17:
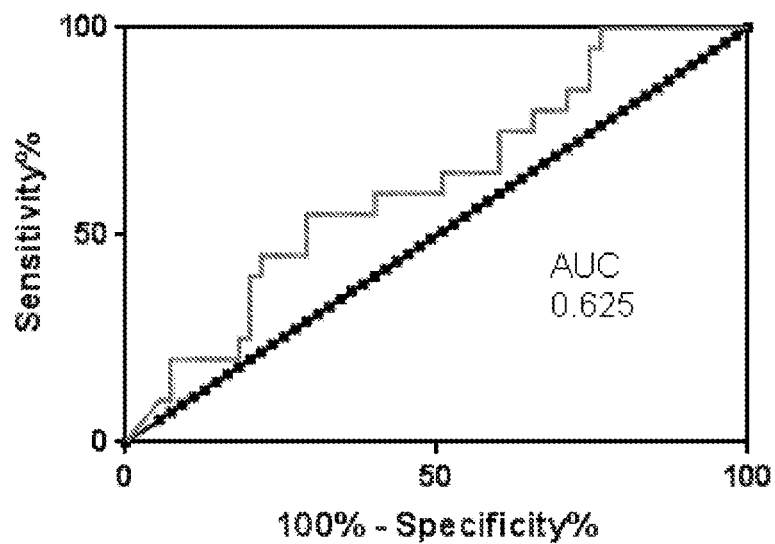

FIG. 17 presents graphs of Western blotting analyses comparing the level of 2-chain HMWK in citrated plasma samples from healthy subjects and HAE patients. A: scatter plot comparing the percent 2-chaim HMWK in samples from healthy subjects ("HV") and HAE patients between HAE attacks ("Basal") and during an HAE attack ("Attack"). B: ROC (receiver operating characteristic) analysis comparing the sensitivity and specificity for the detection of HAE basal samples versus samples from healthy subjects (AUC=0.977). C: ROC analysis comparing the sensitivity and specificity for the detection of HAE attack samples versus samples from healthy subjects (AUC=1). D: ROC analysis comparing the sensitivity and specificity for the detection of HAE attack samples versus HAE basal samples (AUC=0.625).

Figure 18:
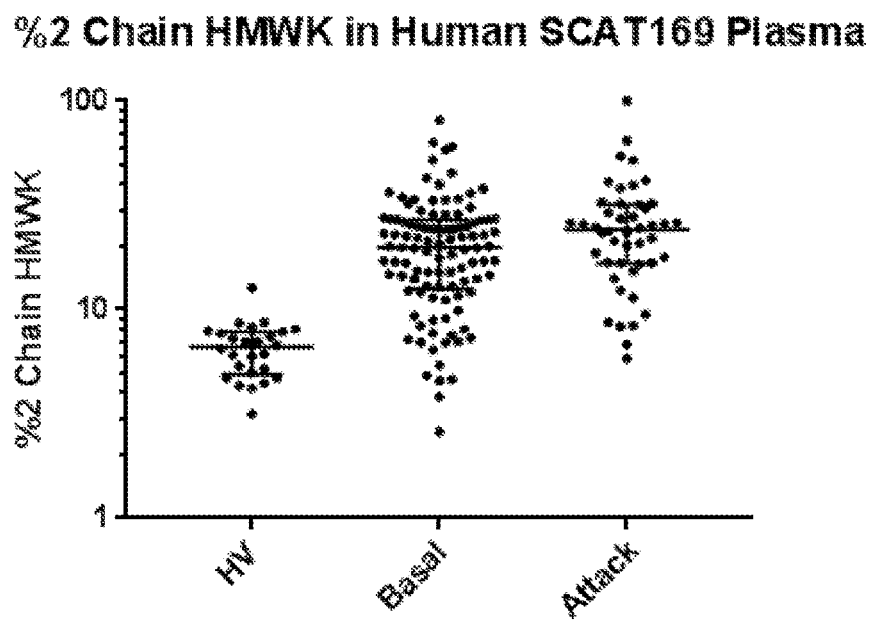
Figure 18:
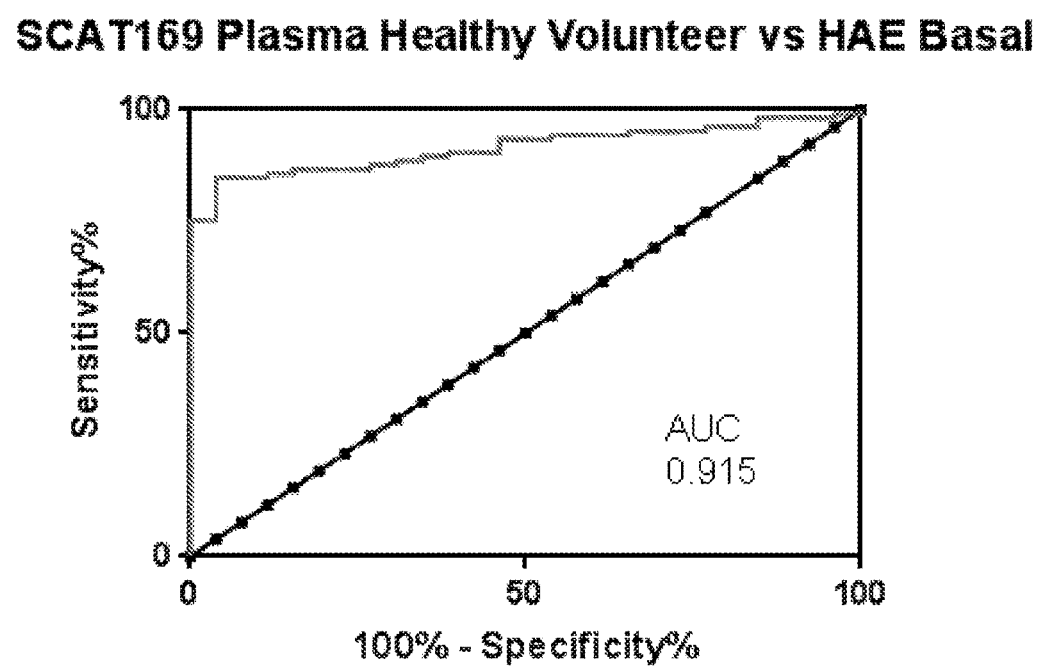
Figure 18:
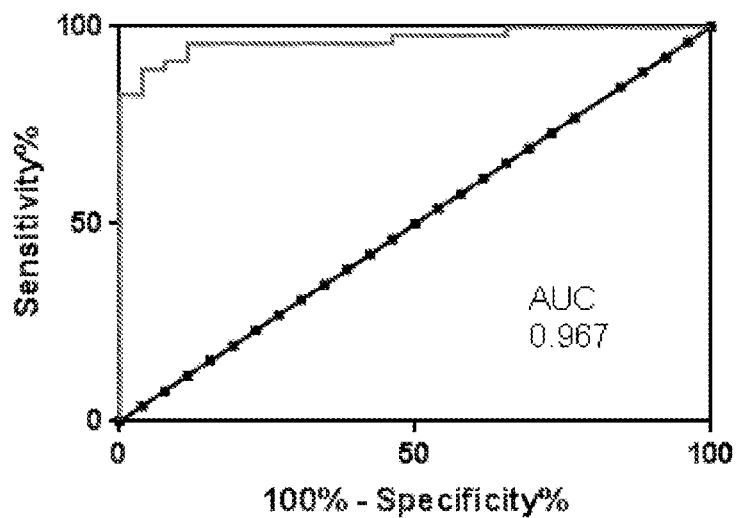
Figure 18:
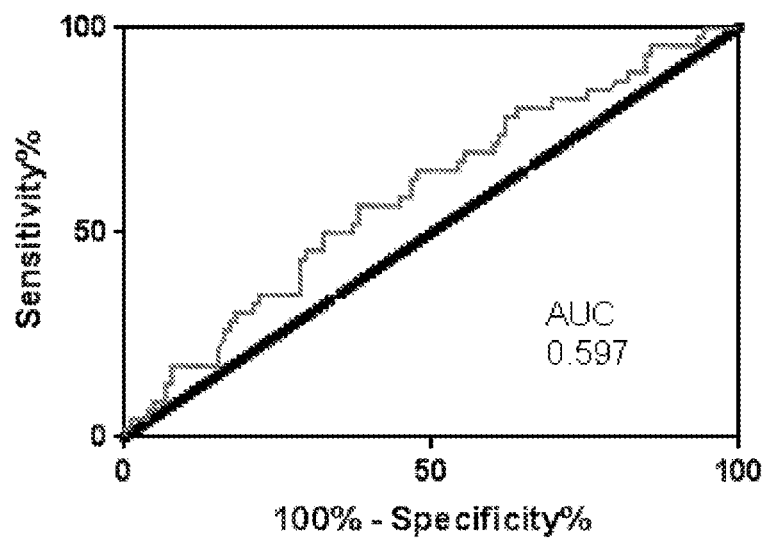

FIG. 18 presents graphs of Western blotting analyses comparing the level of 2-chain HMWK in SCAT169 plasma samples from healthy subjects and HAE patients. A: scatter plot comparing the percent 2-chaim HMWK in samples from healthy subjects ("HV") and HAE patients between HAE attacks ("Basal") and during an HAE attack ("Attack"). B: ROC analysis comparing the sensitivity and specificity for the detection of HAE basal samples versus samples from healthy subjects (AUC=0.915). C: ROC analysis comparing the sensitivity and specificity for the detection of HAE attack samples versus samples from healthy subjects (AUC=0.967). D: ROC analysis comparing the sensitivity and specificity for the detection of HAE attack samples versus HAE basal samples (AUC=0.597).

Figure 19:
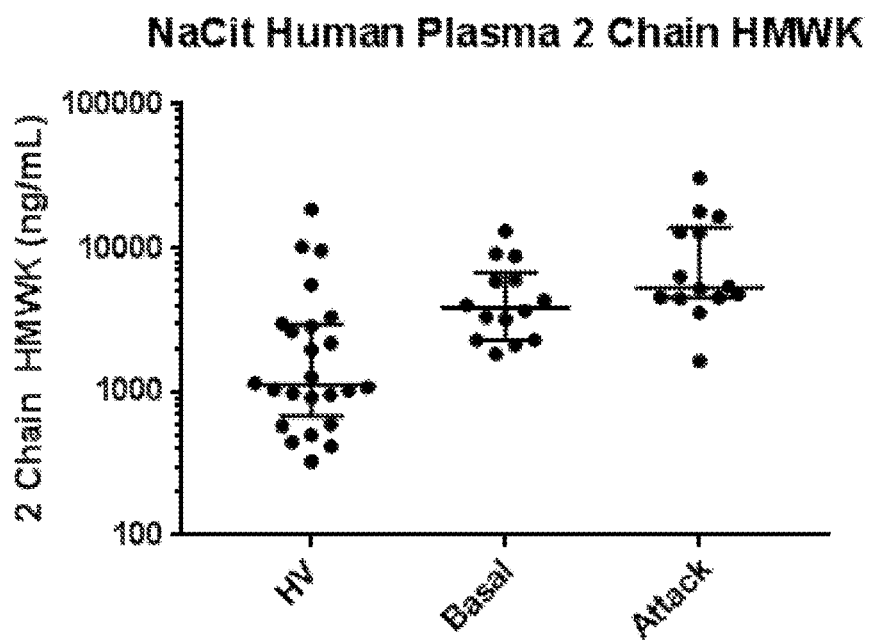
Figure 19:
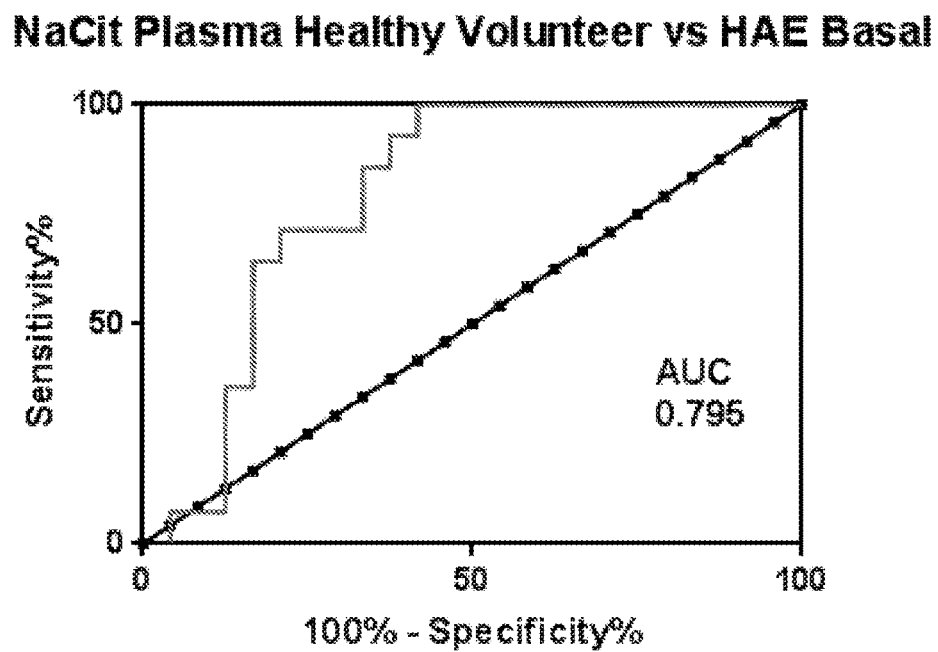
Figure 19:
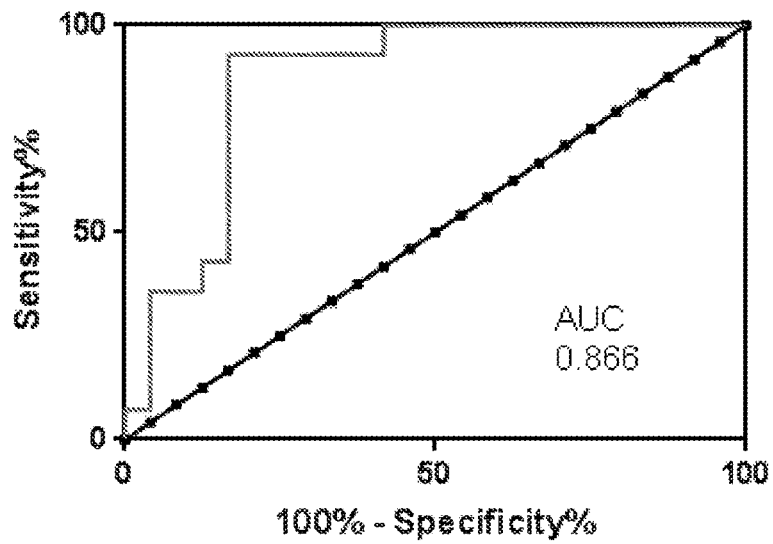
Figure 19:
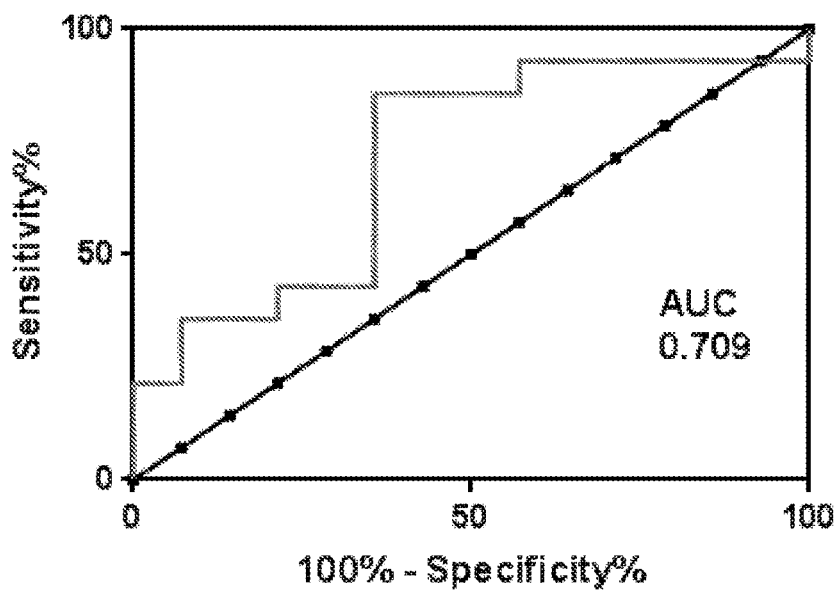

FIG. 19 presents graphs of ELISA analyses comparing the level of 2-chain HMWK in citrated plasma samples from healthy subjects and HAE patients. A: scatter plot comparing the percent 2-chaim HMWK in samples from healthy subjects ("HV") and HAE patients between HAE attacks ("Basal") and during an HAE attack ("Attack"). B: ROC analysis comparing the sensitivity and specificity for the detection of HAE basal samples versus samples from healthy subjects (AUC=0.795). C: ROC analysis comparing the sensitivity and specificity for the detection of HAE attack samples versus samples from healthy subjects (AUC=0.866). D: ROC analysis comparing the sensitivity and specificity for the detection of HAE attack samples versus HAE basal samples (AUC=0.709).

Figure 20:
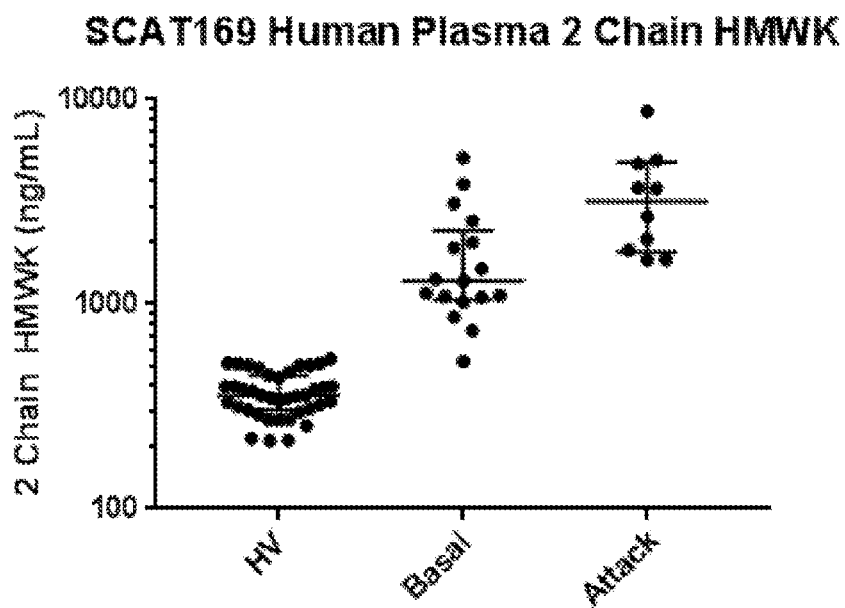
Figure 20:
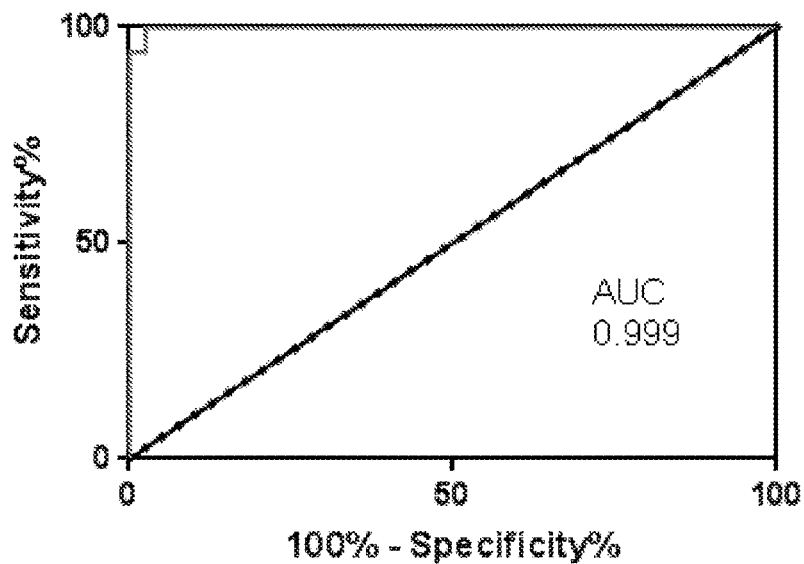
Figure 20:
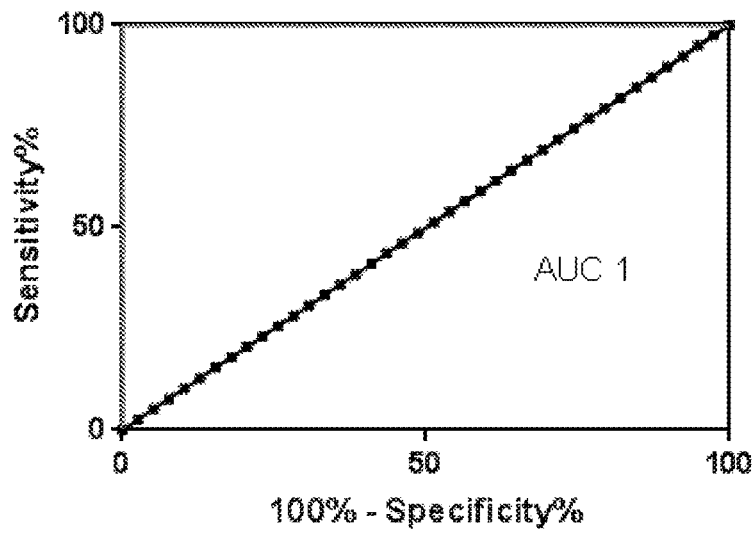
Figure 20:
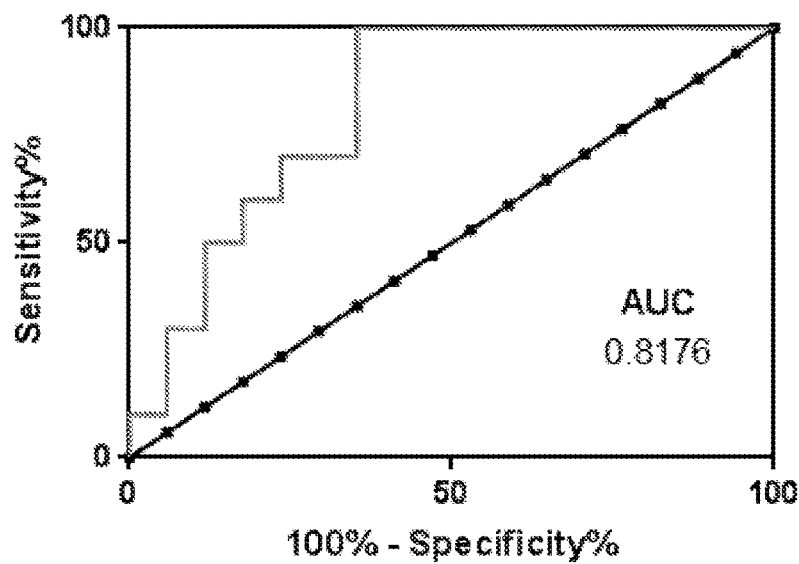

FIG. 20 presents graphs of ELISA analyses comparing the level of 2-chain HMWK in SCAT169 samples from healthy subjects and HAE patients. A: scatter plot comparing the percent 2-chaim HMWK in samples from healthy subjects ("HV") and HAE patients between HAE attacks ("Basal") and during an HAE attack ("Attack"). B: ROC analysis comparing the sensitivity and specificity for the detection of HAE basal samples versus samples from healthy subjects (AUC=0.999). C: ROC analysis comparing the sensitivity and specificity for the detection of HAE attack samples versus samples from healthy subjects (AUC=1). D: ROC analysis comparing the sensitivity and specificity for the detection of HAE attack samples versus HAE basal samples (AUC=0.8176).

DETAILED DESCRIPTION OF PRESENT DISCLOSURE

Plasma kallikrein (PKal) is a serine protease component of the contact system and is the primary bradykinin-generating enzyme in the circulation. The contact system is activated by either factor XIIa (the active form of Factor XII or FXII) upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and proteolytically cleaves the kininogen precursor, high molecular weight kininogen (HMWK), releasing the proinflammatory nonapeptide bradykinin and a cleaved HMWK, which contains two polypeptide chains linked by a disulfide bond (also known as 2-chain HMWK).

As the primary kininogenase in the circulation, plasma kallikrein is largely responsible for the generation of bradykinin in the vasculature. A genetic deficiency in the C1-inhibitor protein (C1-INH) leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

The level of cleaved HMWK was found to be elevated in HAE attack, as well as in other pKal-associated disorders. Thus, cleaved HMWK can serve as a biomarker for monitoring disease development and/or treatment efficacy. However, the art lacks suitable agents and/or suitable assays that can effectively distinguish intact HMWK from its cleaved version.

The present disclosure is based, at least in part, on the development of specific immunoassays that allows for detection of cleaved HMWK with high specificity and sensitivity. It was observed that a Sandwich ELISA in which an agent that specifically binds cleaved HMWK is immobilized on a support member (e.g., a multi-well plate) unexpectedly enhanced detection efficiency as compared to the setting of ELISA in which the antigen (in this case, the cleaved HMWK) is immobilized on the support member. Further, it was observed, unexpectedly, that using the Low-Cross blocking buffer (containing casein), rather than a blocking buffer containing bovine serum album (BSA), enhanced detection specificity and sensitivity during the initial screening to discover antibodies specific for cleaved HMWK. Moreover, the detection specificity and sensitivity was further enhanced when a 96-well plate was used, as compared with a 384-well plate. The present disclosure is also based on, at least in part, the isolation of antibodies that specifically bind a cleaved HMWK.

Accordingly, provided herein are immunoassays for detecting the presence or measuring the level of a cleaved HMWK in a biological sample suspected of containing HMWK species, using an agent (e.g., an antibody) that specifically binds a cleaved HMWK (e.g., the cleaved HMWK having a molecular weight of 46 kDa). Given the correlation between the level of cleaved HMWK and disorders associated with or mediated by pKal (e.g., HAE), the imunoassays described herein can be applied to identify patients who are at risk of such diseases, to monitor disease progression, and/or to monitor efficacy of a treatment against such a disorder.

I. Immunoassays for Specific Detection of Cleaved HMWK

One aspect of the present disclosure relates to immunoassays for detecting cleaved HMWK with high sensitivity and specificity. Such immunoassays may involve a Sandwich ELISA in which an agent that specifically binds a cleaved HMWK is immobilized on a support member, which can be a 96-well plate. The immunoassays described herein allows for selective detection of cleaved HMWK in biological samples, e.g., serum samples or plasma samples, which may contain both intact and cleaved HMWK, as well as LMWK.

(i) High Molecular-Weight Kininogen

High molecular-weight kininogen (HMWK) exists in the plasma as a single polypeptide (1-chain) multi-domain (domains 1-6) protein with a molecular weight of approximately 110 kDa, referred to herein as intact HWMK. The human gene encoding HMWK is kininogen 1 (KNG1). KNG1 is transcribed and alternatively spliced to form mRNAs that encode either HMWK or low molecular weight kininogen (LMWK). An exemplary protein sequence of HMWK is provided below:

```
>gi|156231037|ref|NP_001095886.1| kininogen-1
isoform 1 precursor [Homo sapiens]
                                      (SEQ ID NO: 1)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAATGECTATVGKRSSTKFSVATQTCQITPAEGPVVTAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKARVQVVAGKKYFIDEVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

QGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS
```

Intact HMWK, also referred to herein as "intact kininogen," can be assayed, for example, using coagulant or immunological methods, e.g., radioimmunoassay (see, e.g., Kerbiriou-Nabias, D. M., Br J Haematol, 1984, 56(2):2734-86). A monoclonal antibody to the light chain of human HMWK is known. See, e.g., Reddigari, S. R. & Kaplan, A. P., Blood, 1999, 74:695-702. An assay for HMWK that relies on a chromogenic substrate can also be used. See, e.g., Scott, C. F. et al. Thromb Res, 1987, 48(6):685-700; Gallimore, M. J. et al. Thromb Res, 2004, 114(2):91-96.

HMWK is cleaved by pKal within domain 4 to release the 9 amino acid, pro-inflammatory peptide bradykinin, and a 2-chain form of HMWK, referred to herein as cleaved HMWK. The 2 chains of HMWK are the heavy chain, which contains domains 1-3, and the light chain, which contains domains 5 and 6, joined by a disulfide bond. Upon initial cleavage of intact HMWK, the heavy and light chains have a molecular weight of approximately 65 kDa and 56 kDa, respectively. Further proteolytic processing results in generation of a 46 kDa light chain.

Exemplary sequences of the heavy and light chains of cleaved kininogen are provided below.

> cleaved kininogen-1 heavy chain
(SEQ ID NO: 2)
QESQSEEIDCNDKDLFKAVDAALKKYNSQNQSNNQFVLYRITEATKTVGS

DTFYSFKYEIKEGDCPVQSGKTWQDCEYKDAAKAATGECTATVGKRSSTK

FSVATQTCQITPAEGPVVTAQYDCLGCVHPISTQSPDLEPILRHGIQYFN

NNTQHSSLFMLNEVKRAQRQVVAGLNFRITYSIVQTNCSKENFLFLTPDC

KSLWNGDTGECTDNAYIDIQLRIASFSQNCDIYPGKDFVQPPTKICVGCP

RDIPTNSPELEETLTHTITKLNAENNATFYFKIDNVKKARVQVVAGKKYF

IDFVARETTCSKESNEELTESCETKKLGQSLDCNAEVYVVPWEKKIYPTV

NCQPLGMISLMK

> cleaved kininogen-1 light chain
(SEQ ID NO: 3)
SSRIGEIKEETTVSPPHTSMAPAQDEERDSGKEQGHTRRHDWGHEKQRKH

NLGHGHKHERDQGHGHQRGHGLGHGHEQQHGLGHGHKFKLDDDLEHQGGH

VLDHGHKHKHGHGHGKHKNKGKKNGKHNGWKTEHLASSSEDSTTPSAQTQ

EKTEGPTPIPSLAKPGVTVTFSDFQDSDLIATMMPPISPAPIQSDDDWIP

DIQIDPNGLSFNPISDFPDTTSPKCPGRPWKSVSEINPTTQMKESYYFDL

TDGLS (ii) Antibodies Specific to Cleaved HMWK

The immunoassays described herein may use any agent that can specifically bind a cleaved HMWK, for example, an agent that recognizes a neoepitope on cleaved HMWK that is not present on intact HMWK. In some embodiments, the cleaved HMWK-binding agent is an antibody.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

An antibody that "specifically binds" a cleaved HMWK or an epitope thereof is a term well understood in the art, and methods to determine such specific binding are also well known in the art. A molecule is said to exhibit "specific binding" if it reacts or associates more frequently, more rapidly, with greater duration and/or with greater affinity with a particular target antigen (here a cleaved HMWK) than it does with alternative targets (e.g., intact HMWK and/or LMWK). An antibody "specifically binds" to a target antigen if it binds with greater affinity, avidity, more readily, and/or with greater duration than it binds to other substances. For example, an antibody that specifically (or preferentially) binds to cleaved HMWK or an epitope therein is an antibody that binds this target antigen with greater affinity, avidity, more readily, and/or with greater duration than it binds to other antigens (e.g., intact HMWK or LMWK) or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, the antibodies that specifically binds cleaved HMWK (as well the other antibodies that bind both cleaved and intact, and optionally LMWK) described herein have a suitable binding affinity to a cleaved HMWK (or another target antigen as described herein). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. For example, the binding affinity of an antibody that specifically binds a cleaved HMWK as described herein may be 10-fold, 100-fold, 10,000-fold, or $10_5$-fold higher than the binding affinity of that antibody to intact HMWK and/or LMWK.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[N][Free]/(Kd+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the antibody that specifically binds to cleaved HMWK (also referred to as an anti-cleaved HMWK antibody) binds to the same epitope of a cleaved HMWK as 559B-M004-B04. An "epitope" refers to the site on a target antigen that is bound by a binding protein (e.g., an antibody such as a Fab or full length antibody). The site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature. In some cases, the epitope is linear; in other instances, the epitope is conformational.

A first antibody "binds to the same epitope" as a second antibody if the first antibody binds to the same site on a target antigen that the second antibody binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group) with the site that the second antigen binds.

In some embodiments, the antibody that specifically binds to cleaved HMWK competes against 559B-M004-B04 for binding to HMWK. A first antibody "competes for binding" with a second antibody if the binding of the first antibody to its epitope decreases (e.g., by 10%, 20%, 30%, 40%, 50%, 60%, 70%, 80%, 90%, 100%, or more) the amount of the second antibody that binds to its epitope. The competition can be direct (e.g., the first antibody binds to an epitope that is the same as, or overlaps with, the epitope bound by the second antibody), or indirect (e.g., the binding of the first antibody to its epitope causes a steric change in the target antigen that decreases the ability of the second antibody to bind to its epitope).

In some examples, the antibody that specifically binds to cleaved HMWK comprises a $V_H$ chain that includes a $V_H$ CDR1, a $V_H$ CDR2, and/or a $V_H$ CDR3 at least 75% (e.g., 80%, 85%, 90%, 95%, 96%, 97%, 98%, or 99%) identical to the corresponding $V_H$ CDRs of 559B-M004-B04. Alternatively or in addition, the antibody that specifically binds to cleaved HMWK comprises a $V_L$ CDR1, a $V_L$ CDR2, and/or a $V_L$ CDR3 at least 75% (e.g., 80%, 85%, 90%, 95%, 96%, 97%, 98%, or 99%) identical to the corresponding $V_L$ CDRs of 559B-M004-B04. In some embodiments, the antibody that specifically binds to cleaved HMWK has the same heavy chain and/or light chain complementarity determining regions (CDRs) as 559B-M004-B04.

"Complementarity determining regions" or "CDRs" are known in the art as referring to non-contiguous sequences of amino acids within antibody variable regions, which confer antigen specificity and binding affinity. In general, there are three (3) CDRs in each heavy chain variable region and three (3) CDRs in each light chain variable region. The precise amino acid sequence boundaries of a given CDR can be readily determined using any of a number of well-known schemes, including those described by Kabat et al. (1991), 5th Ed. Public Health Service, National Institutes of Health, Bethesda, Md. (the Kabat" numbering scheme), Al-Lazikani et al., (1997) JMB 273, 927-948 (the Chothia" numbering scheme), MacCallum et al., J. Mol. Biol. 262:732-745 (1996) (the Contact numbering scheme), Lefranc M P et al., Dev Comp Immunol, 2003 January; 27(1):55-77 (the IMGT numbering scheme), and Honegger A and Pluckthun A, J Mol Biol, 2001 Jun. 8; 309(3):657-70, (the AHo numbering scheme).

The boundaries of a given CDR may vary depending on the scheme used for identification. For example, the Kabat scheme is based structural alignments, while the Chothia scheme is based on structural information. The Contact scheme is based on analysis of complex crystal structures and is similar in many respects to the Chothia numbering scheme. Thus, unless otherwise specified, the term "complementary determining region" or "CDR" of a given antibody should be understood to encompass the complementary determining region as defined by any of the known schemes described herein above.

If, determined by the same numbering scheme, an antibody has the same $V_H$ and/or $V_L$ CDRs as 559B-M004-B04 (as well as other exemplary antibodies disclosed herein), such an antibody is deemed as having the same CDRs as 559B-M004-B04 (or the other exemplary antibodies disclosed herein) and is within the scope of the present disclosure. For example, such an antibody may have the same $V_H$ and/or $V_L$ CDRs as clone 559B-M004-B04 as determined by the Chothia numbering scheme. In another example, an anti-cleaved HMWK antibody within the scope of the present disclosure may have the same $V_H$ and/or $V_L$ CDRs as clone 559B-M004-B04, as determined by the Kabat numbering scheme.

Alternatively or in addition, the anti-cleaved HMWK antibody comprises a $V_H$ chain at least 75% (e.g., 80%, 85%, 90%, 95%, 96%, 97%, 98%, or 99%) identical to the $V_H$ chain of 559B-M004-B04 and/or a $V_L$ chain at least 75% (e.g., 80%, 85%, 90%, 95%, 96%, 97%, 98%, or 99%) identical to the $V_L$ chain of 559B-M004-B04. In some embodiments, the antibody is 559B-M004-B04.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NB LAST) can be used.

The sequences of the heavy chain variable region and the light chain variable region of 559B-M004-B04 are shown below. Heavy chain CDR1, CDR2, and CDR3 sequences and light chain CDR1, CDR2, and CDR3 sequences are underlined and in boldface (identified by one scheme as an example).

```
>559B-R0048-A01 (559B-M0004-B04) Heavy Chain Amino
Acid Sequence
                                        (SEQ ID NO: 4)
EVQLLESGGGLVQPGGSLRLSCAASGFT FSFYVMV WVRQAPGKGLEWVSG

ISPSGGNTAYADSVK GRFTISRDNSKNTLYLQMNSLRAEDTAVYYCAR KL

FYYDDTKGYFDF WGQGTLVTVSS

>559B-R0048-A01 (559B-M0004-B04) Light Chain Amino
Acid Sequence
                                        (SEQ ID NO: 5)
QYELTQPPSASGTPGQRVTLSC SGSSSNIGSNYVY WYQQLPGTAPKLLIY

RNNQRPS GVPDRFSGSKSGTSASLAISGLQSEDEADYYCA AWDDSLNGRV

FGGGTKLTVL
```

In some instances, the antibody that specifically binds a cleaved HMWK may contain one or more (e.g., up to 5, up to 3, or up to 1) conservative mutations in one or more of the heavy chain CDRs, or one or more of the light chain CDRs in 559B-M0004-B04, e.g., at positions where the residues are not likely to be involved in interacting with the cleaved HMWK. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Antibodies capable of binding to cleaved HMWK (as well as antibodies capable of binding to intact HMWK and/or LMWK) as described herein can be made by any method known in the art. See, for example, Harlow and Lane, (1988) Antibodies: A Laboratory Manual, Cold Spring Harbor Laboratory, New York.

In some embodiments, antibodies specific to a target antigen (a cleaved HMWK, the intact HMWK, and/or LMWK) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-PKal monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the PKal activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to improve the affinity (affinity maturation), or other characteristics of the antibody. It may be desirable to genetically manipulate the antibody sequence to obtain greater affinity and/or specificity to the target antigen. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348: 552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704, 692) can be adapted to produce a phage or yeast scFv library and scFv clones specific to a PKal can be identified from the library following routine procedures. Positive clones can be subjected to further screening to identify those that specifically bind a target antigen, such as a cleaved HMWK.

In some embodiments, the antibodies specific to a cleaved HMWK (or to intact HMWK or LMWK) may be isolated from an antibody library, which may be a synthetic library or a natural library. A natural antibody library refers to a library derived from a natural source (e.g., a human donor) following routine practice. A synthetic antibody library refers to a library the members of which are designed following predetermined rules (e.g., having a complete randomized CDR region such as CDRs or a semi randomized CDR region such as CDR1 or CDR2 of the heavy chain, the light chain, or both).

In some instances, the antibody library is a display library (e.g., a phage display library or a yeast display library). A display library is a collection of entities; each entity includes an accessible polypeptide component and a recoverable component that encodes or identifies the polypeptide component. The polypeptide component is varied so that different amino acid sequences are represented. The polypeptide component can be of any length, e.g., from three amino acids to over 300 amino acids. A display library entity can include more than one polypeptide component, for example, the two polypeptide chains of a sFab. In one exemplary implementation, a display library can be used to identify proteins that bind to a cleaved HMWK (as well as other target antigens described herein). In a selection, the polypeptide component of each member of the library is probed with a cleaved HMWK (or a fragment thereof) and if the polypeptide component binds to the cleaved HMWK, the display library member is identified, typically by retention on a support. An exemplary illustration for identifying antibodies specific to cleaved HMWK using a phage display antibody library is provided in FIG. 12.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis.

Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the HMWK polypeptide have been replaced (swapped) with sequences from a closely related, but antigenically distinct protein. By assessing binding of the antibody to the mutant HMWK, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Any of the anti-cleaved HMWK antibodies is also within the scope of the present disclosure.

(iii) Immunoassays

Provided herein are immunoassays for detecting a cleaved HMWK. As used herein, the term "immunoassay" may be referred to interchangeably as an immune-based assay or immuno-based assay. In general, an immunoassay detects the presence and/or concentration (level) of a molecule (e.g., HMWK), in a sample using an agent that binds to the molecule, such as an antibody. Examples of immunoassays include Western blots, enzyme linked immunosorbent assays (ELISAs), lateral flow assay, radioimmunoassays, electrochemiluminescence-based detection assays, magnetic immunoassays, and related techniques. In some embodiments, the immunoassay is an ELISA assay. In some embodiments, the immunoassay is a sandwich ELISA assay. In some embodiments, the immunoassay is a lateral flow assay.

ELISAs are known in the art (see, e.g., Crowther, John R (2009). "The ELISA Guidebook." 2nd ed. Humana Press and Lequin R (2005). "Enzyme immunoassay (EIA)/enzyme-linked immunosorbent assay (ELISA)". Clin. Chem. 51 (12): 2415-8) and exemplary ELISAs are described herein. Kits for performing ELISAs are also known in the art and commercially available (see, e.g., ELISA kits from Life Technologies and BD Biosciences).

To perform the immunoassay described herein, a sample may be obtained from a subject. As used herein, a "sample" refers to a composition that comprises tissue, e.g., blood, plasma or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is a body fluid sample such as a serum or plasma sample. A sample to be analyzed by the immunoassay described herein can be either an initial unprocessed sample taken from a subject or subsequently processed, e.g., partially purified or preserved forms. In some embodiments, multiple (e.g., at least 2, 3, 4, 5, or more) samples may be collected from the subject, over time or at particular time intervals, for example to assess the progression of a disease or disorder or evaluate the efficacy of a treatment. The multiple samples may be obtained before and after a treatment, or during the course of a treatment.

A sample can be obtained from a subject using any means known in the art. In some embodiments, the sample is obtained from the subject by collecting the sample (e.g., a blood sample) into an evacuated collection tube (e.g., an evacuated blood collection tube). In some embodiments, the evacuated collection tube contains one or more protease inhibitors, for example, to reduce or prevent ex vivo activation of the contact system during sample collection. Such protease inhibitors may be contained in a liquid formulation. In some embodiments, the protease inhibitors comprise at least one serine protease inhibitor and at least one cysteine protease inhibitor. Such evacuated collection tubes are known in the art. See, for example, PCT Application No. US2016/046681. Optionally, an evacuated blood collection tube may further comprise one or more anti-coagulants.

A "patient," "subject" or "host" (these terms are used interchangeably) to be treated by the subject method may mean either a human or non-human animal. In some embodiments, a subject is suspected of or is at risk for or suffers from a kallikrein-mediated disorder, e.g., a bradykinin-mediated disorder, such as hereditary angioedema (HAE), non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g., anaphylaxis, asthma, chronic obstructive pulmonary disease, acute respiratory distress syndrome, cystic fibrosis, persistent, rhinitis) and tissue injuries (e.g., burn or chemical injury).

Alternatively or in addition, the subject who needs the analysis described herein may be a patient of the disease or disorder. Such a subject may be under the attack of the disease (e.g., HAE) currently, or may suffer from the disease in the past (e.g., during disease quiescence currently). In some examples, the subject is a human patient who may be on a treatment of the disease, for example, a treatment involving a C1 esterase inhibitor (C1-INH), a plasma kallikrein inhibitor, or a bradykinin inhibitor. In other instances, such a human patient may be free of such a treatment.

The sample described herein can be subject to analysis using an agent that specifically binds a cleaved HMWK to determine the level of the cleaved HMWK in the sample. In some embodiments, the immunoassays described herein may in the format of a sandwich ELISA, in which a first agent (e.g., the antibody described herein) that specifically binds the cleaved HMWK is immobilized on a support member. The support member can then be incubated with a sample as described herein for a suitable period of time under conditions that allow for the formation of cleaved HMWK/first agent (e.g., antibody) complex. Such a complex can then be detected using a second agent that binds HMWK. The second agent can be conjugated to a label, which can release a signal directly or indirectly. The intensity of the signal represents the level of the cleaved HMWK in the sample.

Any support member known in the art may be used in the method, including but not limited to a membrane, a bead, a slide, or a multi-well plate. Selection of an appropriate support member for the immunoassay will depend on various factor such as the number of samples and method of detecting the signal released from label conjugated to the second agent.

In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput immunoassays. Individual immunoassays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate::vision system available from Perkin Elmer, Waltham, Mass.) may be used. This plate reader is capable of kinetic-based fluorescence analysis. The plate::vision system has high collection efficiency optics and has special optics designed for the analysis of 96 wells in parallel. Additional suitable parallel plate readers include but are not limited to the SAFIRE (Tecan, San Jose, Calif.), the FLIPRTETRA® (Molecular Devices, Union City, Calif.), the FDSS7000 (Hamamatsu, Bridgewater, N.J.), and the CellLux (Perkin Elmer, Waltham, Mass.).

As described in Example 1, it was unexpectedly discovered that the surface area and/or volume of the wells of the multi-well plate may affect the results of the immunoassay. In some embodiments, the described immunoassays are performed in 96-well plates, such as a 96-well ELISA plate.

In other embodiments, high-throughput screening immunoassays of the present disclosure can be automated (e.g., adapted to robotic assays).

In some embodiments, the immunoassays may be performed on low-throughput platforms, including single immunoassay format. For example, a low-throughput platform may be used to measure the presence and amount of cleaved HMWK in biological samples (e.g., biological tissues, tissue extracts) for diagnostic methods, monitoring of disease and/or treatment progression, and/or predicting whether a disease or disorder may benefit from a particular treatment.

Any method known in the art can be used to immobilize an agent that specifically binds a cleaved HMWK such as the antibodies described herein onto a support member as also described herein. In some embodiments, the immobilization involves binding the agent (e.g., the antibody) to the support member. In other embodiments, the immobilization involves adsorbing the antibody to the support member. Such adsorption methods may be performed, for example, by incubating the antibody in a buffer in the wells of a multi-well plate. In some embodiments, the agent such as the antibody is provided in a coating buffer and incubated in the wells of a multi-well plate. Coating buffers will be evident to one of skill in the art and may be prepared or obtained from a commercial source. Non-limiting examples of coating buffers include 50 mM sodium bicarbonate, pH 9.6; 0.2 M sodium bicarbonate, pH 9.4; phosphate buffered solution (50 mM phosphate, pH 8.0, 0.15 M NaCl); carbonate-bicarbonate solution; and TBS (50 mM TRIS, pH 8.0, 0.15 M NaCl).

In some embodiments, the first agent is immobilized on the support member by hydrophobic interactions between the first agent and the support member. In some embodiments, the first agent is immobilized on the support member using electrophoretic transfer.

Either before or after immobilization, or both, the support member may be incubated with a blocking buffer. In general, blocking buffers are used to block any of the exposed surface of the support membrane (e.g., sites on the support membrane unoccupied by the first agent). Use of a blocking buffer may reduce the baseline signal detected (i.e., "background interference") and/or improve the sensitivity of the immunoassay and/or reduce non-specific binding of components of the sample to the support membrane. As described in Example 1, selection of the blocking buffer affected the results of the immunoassay. In some embodiments, the blocking buffer contains serum albumin, such as bovine serum albumin or human serum albumin. In some embodiments, the blocking buffer is a BSA buffer (e.g., 2% BSA in PBS buffer). In some embodiments, the blocking buffer is free from serum albumin, such as bovine serum albumin or human serum albumin. In some embodiments, the blocking buffer comprises casein fragments, and optionally NaCl and Tween and may have a pH 7.0-7.4. In some embodiments, the casein fragments are high purity casein fragments. Such a blocking buffer may be prepared or obtained from a commercial source (e.g., The Blocking Solution LowCross from CANDOR Bioscience).

The support member, on which the agent specific to a cleaved HMWK is attached, can be brought in contact (incubated) with a sample as described herein, which is suspected of containing the cleaved HMWK. In general, the term "contact" refers to an exposure of the support member with the biological sample or agent for a suitable period sufficient for the formation of complexes between the agent, such as an antibody, and the cleaved HMWK in the sample, if any. Afterwards, the sample may be removed from the support member, which can then be washed for multiple times to remove any unbound cleaved HMWK. In some embodiments, the contacting is performed by capillary action in which a biological sample or agent is moved across a surface of the support membrane.

The support member can then be incubated with a second agent that binds HMWK for a suitable period allowing for the binding of the second agent to HMWK attached to the support member.

The second agent can be any agent capable of binding to HMWK, such as an antibody capable of binding to HMWK (either specific to the cleaved form of HMWK or can cross react to both the cleaved HMWK and intact HMWK). In some embodiments, the second agent comprises one or more antibodies that bind HWMK (cleaved and/or intact). In some embodiments, the antibody is a mouse monoclonal antibody or a monoclonal sheep antibody. It is conjugated with a label, which is a compound capable of releasing a signal either directly or indirectly (e.g., via interaction with one or more additional compounds).

In some embodiments, the label is a signal releasing agent, which is an agent that either directly releases a signal (e.g., a dye or fluorophore) or releases a signal upon interacting with a substrate (e.g., an enzyme such as HRP or β-galactosidase, which can convert a colorless substrate to a colored product). As used herein, the term "fluorophore" (also referred to as "fluorescent label" or "fluorescent dye") refers to moieties that absorb light energy at a defined excitation wavelength and emit light energy at a different wavelength.

In other embodiments, the label can be a member of a receptor-ligand pair. As used herein, a "ligand-receptor pair" refers to a pair of molecules (e.g., biological molecules) that have a specific affinity for each other, e.g., biotin-streptavidin. In this case, the support member carrying the first agent-cleaved HMWK-second agent may be further incubated with the other member of the ligand-receptor pair for a suitable period such that the two members of the receptor-ligand pair interact. The other member of the receptor-ligand pair is conjugated with a signal releasing agent as described herein. In one example, the second agent is conjugated to biotin and HRP-conjugated streptavidin is used for detection.

After washing away any unbound conjugate, a substrate solution may be added to aid in detection. For example, after a set interval, the reaction may be stopped (e.g., by adding 1 N NaOH) and the concentration of colored product formed may be measured in a spectrophotometer. The intensity of color is proportional to the concentration of bound antigen.

Next, the signal released from the label as described herein can be detected/measured by routine methodology, which would depend on the specific format of an immunoassay and the signal releasing agent used therein. As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject.

Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

Any of the immunoassays described herein, e.g., one or more steps of the immunoassays, may be carried out in a suitable assay buffer, which will be evident to one of skill in the art. In some embodiments, the assay buffer contains or has been supplemented with $ZnCl_2$. In some embodiments, the assay buffer contains at least about 10 µM, 20 µM, 30 µM, 40 µM, 50 µM, 60 µM, 70 µM, 80 µM, 90 µM, 100 µM, 150 µM, 200 µM, 250 µM, 300 µM, 350 µM, 400 µM, 450 µM, 500 µM or more $ZnCl_2$. In some embodiments, such a $ZnCl_2$-containing assay buffer is used in the step in which the agent specific to cleaved HMWK (e.g., an antibody specific to cleaved HMWK) binds a cleaved HMWK. $ZnCl_2$ enhances the binding activity of the agent (e.g., antibody) to the cleaved HMWK.

In some embodiments, the assay buffer contains serum albumin, such as bovine serum albumin or human serum albumin. In some embodiments, the assay buffer contains at least about 0.01%. 0.02%, 0.03%, 0.04%. 0.05%, 0.06%, 0.07%, 0.08%, 0.09%, 0.1%, 0.12%, 0.014%, 0.16%, 0.18%, 0.2%, 0.25%, 0.3%, 0.4%, or more BSA. In some embodiments, the assay buffer contains a surfactant, such as Tween-20. In some embodiments, the assay buffer contains 0.01%. 0.02%, 0.03%, 0.04%. 0.05%, 0.06%, 0.07%, 0.08%, 0.09%, 0.1% or more of a surfactant. In one example, the assay buffer contains 0.1% BSA and 0.05% Tween-20 in PBS.

(iv) Diagnostic and Prognostic Applications

The assay methods and kits described herein can be applied for evaluation of a disease or disorder associated with plasma kallikrein, such as those described herein (e.g., HAE), given the correlation between the level of cleaved HMWK and such diseases or disorders (e.g. as a biomarker). Alternatively or in addition, the assay methods and kits described herein may be used to monitor the progress of such a disease, assess the efficacy of a treatment for the disease, identify patients suitable for a particular treatment, and/or predict disease status (e.g., attack versus quiescence) in a subject.

In some embodiments, the level of cleaved HMWK determined by the immunoassay described herein can be relied on to evaluate whether a subject (e.g., a human patient) from whom the biological sample is obtained, has or is at risk for a disease or disorder associated with plasma kallikrein, such as HAE or autoimmune disease such as RA, UC, and Crohn's disease). The level of cleaved kininogen can then be compared with either the intact kininogen or the total amount of kininogen in the sample to determine a value (e.g., percentage) of cleaved kininogen, a value of intact kininogen, or both, in the sample. The value of cleaved kininogen and/or intact kininogen can be compared to a reference value to determine whether the subject has or is at risk for the PKal-mediated disorder, e.g., HAE or an autoimmune disease, such as RA, UC, and Crohn's disease. For example, if the percentage of cleaved kininogen is at or higher than a reference number, the subject can be identified as having or at risk for a pKal-mediated disorder such as HAE, RA, UC, and Crohn's disease. Alternatively, if the percentage of intact kininogen is at or lower than a reference number, the subject can be identified as having or at risk for a pKal-mediated disorder such as HAE, RA, UC, and Crohn's disease.

In some embodiments, the sample for analysis of the methods described herein is derived from a human subject who has or is at risk of having hereditary angioedema (HAE). HAE is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema marginatum during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When HAE is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., *J Allergy Clin Immunol*, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. CINRYZE®, which is nanofiltered, was approved by the F.D.A. in 2008 for prophylaxis. Rhucin/Ruconest (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol*, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal. The present disclosure is based, at least in part, on the identification of additional proteins that have differential levels in samples from HAE patients as compared to healthy individuals (Table 1). Measuring the level or presence of 2-HMWK can be used to identify whether a subject has a disease, such as HAE. In some embodiments, the methods may be used to determine whether a patient has had or is having an HAE attack.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient.* 2012; 5(2):113-26.

The value of cleaved kininogen and/or intact kininogen detected in a sample from a subject can be compared to a reference value to determine whether the subject has or is at risk for the PKal-mediated disorder (e.g., HAE). Alternatively or in addition, the level of the cleaved kininogen and/or intact kininogen detected in a sample from the subject can be compared to a reference value to assess the efficacy of a treatment for the disorder, the prognosis or severity of the disorder, and/or identifying a subject as a candidate for treatment.

The reference value can be a control level of cleaved kininogen percentage. In some embodiments, the control level is the percentage of cleaved kininogen in a control sample, such as a sample (e.g., blood or plasma sample) obtained from a healthy subject or population of healthy subjects, which preferably are of the same species as the candidate subject. As used herein, a healthy subject is a subject that is apparently free of the target disease (e.g., a PKal-mediated disorder such as HAE or autoimmune diseases such as RA, US, and Crohn's disease) at the time the level of cleaved and/or intact kininogen is measured or has no history of the disease.

The control level can also be a predetermined level or threshold. Such a predetermined level can represent the percentage of cleaved kininogen in a population of subjects that do not have or are not at risk for the target disease. It can also represent the percentage of cleaved kininogen in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the percentages of cleaved kininogen in a control population within a predetermined percentile.

The control level as described herein can be determined by routine technology. In some examples, the control level can be obtained by performing a conventional method (e.g., the same assay for obtaining the level of cleaved and/or intact kininogen in a test sample as described herein) on a control sample as also described herein. In other examples, levels of cleaved and/or intact kininogen can be obtained from members of a control population and the results can be analyzed by, e.g., a computational program, to obtain the control level (a predetermined level) that represents the level of cleaved and/or intact kininogen in the control population.

By comparing the percentage of cleaved kininogen in a sample obtained from a candidate subject to the reference value as described herein, it can be determined as to whether the candidate subject has or is at risk for the PKal-mediated disease (e.g., HAE or an autoimmune disease such as RA, UC, and Crohn's disease). For example, if the percentage of cleaved kininogen in a sample of the candidate subject deviates from the reference value (e.g., increased as compared to the reference value or decreased as compared to the reference value), the candidate subject might be identified as having or at risk for the disease. When the reference value represents represent the percentage range of cleaved kininogen in a population of subjects that have the target disease, the percentage of cleaved kininogen in a sample of a candidate falling in the range indicates that the candidate subject has or is at risk for the target disease. In some instances, a reference value may represent a background level indicating absence of cleaved kininogen. Presence of cleaved kininogen is deemed as a deviation from such a background reference value. As used herein, a "deviation from" a control sample or reference value encompasses levels of cleaved HMWK as well as the presence or absence of cleaved HMWK in the sample.

As used herein, "an elevated level or a level above a reference value" means that the level/percentage of cleaved kininogen is higher than a reference value, such as a pre-determined threshold of a level/percentage of cleaved kininogen in a control sample. Control levels are described in detail herein.

An elevated percentage of cleaved kininogen includes a cleaved kininogen percentag that is, for example, 1%, 5%, 10%, 20%, 30%, 40%, 50%, 60%, 70%, 80%, 90%, 100%, 150%, 200%, 300%, 400%, 500% or more above a reference value. An elevated percentage of cleaved kininogen also includes increasing a phenomenon from a zero state (e.g., no or undetectable cleaved kininogen and/or intact kininogen that binds to a capture reagent in a sample) to a non-zero state (e.g., some or detectable cleaved kininogen and/or intact kininogen).

As used herein, "a decreased percentage/level or a percentage/level below a reference value" means that the percentage/level of cleaved is lower than a reference value, such as a pre-determined threshold of cleaved kininogen in a control sample. Control levels are described in detail herein.

An decreased level of cleaved kininogen includes a cleaved kininogen that is, for example, 1%, 5%, 10%, 20%, 30%, 40%, 50%, 60%, 70%, 80%, 90%, 100%, 150%, 200%, 300%, 400%, 500% or more lower than a reference value. A decreased level of cleaved kininogen that binds to a capture reagent also includes decreasing a phenomenon from a non-zero state (e.g., some or detectable cleaved kininogen in a sample) to a zero state (e.g., no or undetectable cleaved kininogen in a sample).

In some embodiments, the candidate subject is a human patient having a symptom of a pKal-mediated disorder, e.g., such as HAE or an autoimmune disease such as RA, UC, and Crohn's disease. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an antihistamine therapy, a corticosteroid therapy, or both.

A subject identified in the methods described herein may be subject to a suitable treatment.

The assay methods and kits described herein can be applied for evaluation of the efficacy of a treatment for a disease associated with plasma kallikrein, such as those described herein, given the correlation between the level of cleaved HMWK and such diseases. For examples, multiple biological samples (e.g., blood or plasma samples) can be collected from a subject to whom a treatment is performed either before and after the treatment or during the course of the treatment. The levels of cleaved and/or intact kininogen can be measured by any of the assay methods as described herein and values (e.g., percentages) of cleaved and/or intact kininogen can be determined accordingly. If the percentage of the cleaved kininogen decreases after the treatment or over the course of the treatment (the cleaved kininogen percentage in a later collected sample as compared to that in an earlier collected sample) or the percentage of intact kininogen increases after the treatment or over the course of the treatment, it indicates that the treatment is effective. In some examples, the treatment involves a therapeutic agent, such as a kallikrein inhibitor, a bradykinin B2 receptor antagonist, or a C1-INH replacement agent. Examples of the therapeutic agents include, but not limited to, landadelumab (DX-2930), ecallantide (DX-88), icantibant, and human plasma-derived C1-INH.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of cleaved kininogen, either alone or in combination with that of intact kininogen, can also be relied on to identify a disorder that may be treatable by a pKal inhibitor. To practice this method, the level of cleaved kiniogen and/or the level of intact kininogen in a sample collected from a subject (e.g., a blood sample or a plasma sample) having a target disease can be measured by a suitable assay, e.g., those described herein such as a Western blot or ELISA assay. Values such as percentages of the cleaved and/or intact kininogen can be determined as described herein. The values of cleaved kininogen and/or intact kininogen can be compared with a reference value as described herein. If the value of cleaved kininogen/intact kininogen deviates from the reference value (e.g., elevated or decreased), it indicates that a pKal inhibitor may be effective in treating the disease. For example, if the percentages of cleaved kininogen are decreasing after the treatment or over the course of the treatment, the treatment can be identified as being effective. Alternatively, if the percentages of intact kininogen are increasing after the treatment or over the course of the treatment, the treatment is identified as being effective.

If the disease is identified as being susceptible (can be treated by) to a pKal inhibitor, the method can further comprise administering to the subject having the disease an effective amount of a pKal inhibitor, e.g., ecallantide (DX-88), EPIKAL-2, or landadelumab (DX-2930).

Also within the scope of the present disclosure are methods of evaluating the severity of a disease or disorder associated with plasma kallikrein or the disease state. For example, as described herein, HAE may be in the quiescent state (basal state), during which the subject does not experience symptoms of the disease. HAE attacks are typically recurrent episodes in which the subject may experience pain and swelling, for example in the hands, feet, face, gastrointestinal tract, genitals, and larynx (throat) that can last from two to five days. In some embodiments, the level of 2-HMWK is indicative of whether the subject will experience, is experiencing, or will soon experience an HAE attack. In some embodiments, the methods involve comparing the level of 2-HMWK in a sample obtained from a subjecting having HAE to the level of 2-HMWK in a sample from the same subject, for example a sample obtained from the same subject at basal state or a sample obtained from the same subject during a HAE attack.

(v) Non-Clinical Applications

Further, assays for detecting the levels of cleaved 2-HMWK described herein may be used for research purposes. Although many diseases and disorders associated with or mediated by plasma kallikrein have been identified, it is possible that other diseases are mediated by similar mechanisms or involve similar components. In some embodiments, the methods described herein may be used to identify a disease as being associated with or mediated by plasma kallikrein or with components of the contact activation system. In some embodiments, the methods described herein may be used to study mechanisms (e.g., the discovery of novel biological pathways or processes involved in disease development) or progression of a disease.

In some embodiments, the levels of cleaved 2-HMWK as measured using the assays described herein, may be relied on in the development of new therapeutics for a disease associated with the contact activation system. For example, the levels of cleaved 2-HMWK may be measured in samples obtained from a subject having been administered a new therapy (e.g., a clinical trial). In some embodiments, the levels of cleaved 2-HMWK may indicate the efficacy of the new therapeutic or the progression of the disease in the subject prior to, during, or after the new therapy.

II. Treatment of Diseases Associated with Plasma Kallikrein

A subject at risk for or suffering from a disease associated with plasma kallikrein, as identified using the methods and assays described herein, may be treated with any appropriate therapeutic agent. In some embodiments, provided methods include selecting a treatment for a subject based on the output of the described method, e.g., measuring the level of cleaved 2-HMWK.

In some embodiments, the method comprises one or both of selecting or administering a therapeutic agent, e.g., a kallikrein inhibitor, a bradykinin B2 receptor inhibitor, and/or a C1 esterase inhibitor, for administration to the subject based on the output of the assay, e.g., 2-HMWK detection.

In some embodiments, the therapeutic agent is administered one or more times to the subject. In some embodiments, a plasma kallikrein inhibitor is administered to a subject. In some embodiments, kallikrein inhibitor is a peptide, a small molecule inhibitor, a kallikrein antibody, or a fragment thereof. In some embodiments, an antagonist of bradykinin B2 receptor is administered to a subject. In some embodiments, a C1-INH is administered to a subject.

The therapeutic agent, e.g., kallikrein inhibitor, bradykinin B2 receptor inhibitor, and/or C1-INH, may be administered along with another therapy as part of a combination therapy for treatment of the disease or condition that involves the contact activation system. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding agent such as a plasma kallikrein inhibitor is administered to a subject at risk or suffering from a disease associated with the contact activation system.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., *Protein Engineering* (1990) 3(7):591-598; Hynes et al., *Biochemistry* (1990) 29:10018-10022) are known. At least eighty one Kunitz domain sequences are known. Known human homologues include three Kunitz domains of LACI also known as tissue factor pathway inhibitor (TFPI) (Wun et al., *J. Biol. Chem.* (1988) 263(13):6001-6004; Girard et al., *Nature* (1989) 338:518-20; Novotny et al, *J. Biol. Chem.* (1989) 264(31):18832-18837) two Kunitz domains of Inter-α-Trypsin Inhibitor, APP-I (Kido et al. *J. Biol. Chem.* (1988) 263(34):18104-18107), a Kunitz domain from collagen, three Kunitz domains of TFPI-2 (Sprecher et al., *PNAS USA* (1994) 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 1) containing three Kunitz domains.

TABLE 1

Exemplary Natural Kunitz Domains

```
LACI        1 MIYTMKKVHA LWASVCLLLN LAPAPLNAds eedeehtiit
(SEQ ID  dtelpplklM
NO: 78)    51 HSFCAFKADD GPCKAIMKRF FFNIFTRQCE EFIYGGCEGN
           QNRFESLEEC
          101 KKMCTRDnan riikttlqqe kpdfCfleed pgiCrgyitr
           yfynnqtkqC
          151 erfkyggClg nmnnfetlee CkniCedgpn gfqvdnygtq
           lnavnnsltp
          201 qstkvpslfe fhgpswCltp adrglCrane nrfyynsvig
           kCrpfkysgC
          251 ggnennftsk qeClraCkkg fiqriskggl iktkrkrkkci
           rvkiayeeif
          301 vknm The signal sequence (1-28) is uppercase and
           underscored
           LACI-K1 (50-107) is uppercase
           LACI-K2 (121-178) is underscored
           LACI-K3 (211-270) is bold BPTI                 1         2         3         4         5
(SEQ ID  12345678901234567890123456789012345678901234567890123456789012345678
NO: 79)  RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (*J. Biol. Chem.* (1988) 263(13):6001-6004). Girard et al. (*Nature* (1989) 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. *Proteins* (1997) 28(3):405-420 and a detailed description of HMMs can be found, for example, in Gribskov et al. *Meth. Enzymol.* (1990) 183:146-159; Gribskov et al. *Proc. Natl. Acad. Sci. USA* (1987) 84:4355-4358; Krogh et al. *J. Mol. Biol.* (1994) 235:1501-1531; and Stultz et al. *Protein Sci.* (1993) 2:305-314. The SMART database (Simple Modular Architecture Research Tool, EMBL, Heidelberg, Del.) of HMMs as described in Schultz et al. *Proc. Natl. Acad. Sci. USA* (1998) 95:5857 and Schultz et al. *Nucl. Acids Res* (2000) 28:231. The SMART database contains domains identified by profiling with the hidden Markov models of the HMMer2 search program (R. Durbin et al. (1998) *Biological sequence analysis: probabilistic models of proteins and nucleic acids*. Cambridge University Press). The database also is annotated and monitored. The ProDom protein domain database consists of an automatic compilation of homologous domains (Corpet et al. *Nucl. Acids Res*. (1999) 27:263-267). Current versions of ProDom are built using recursive PSI-BLAST searches (Altschul et al. *Nucleic Acids Res*. (1997) 25:3389-3402; Gouzy et al. *Computers and Chemistry* (1999) 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. (2002) 30:235-238.

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., *Nature* (1989) 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, the plasma kallikrein inhibitor binds to the active form of plasma kallikrein. In some embodiments, the plasma kallikrein inhibitor, binds to and inhibits plasma kallikrein, e.g., human plasma kallikrein and/or murine kallikrein. Exemplary polypeptide plasma kallikrein agents are disclosed in U.S. Pat. Nos. 5,795,865, 5,994,125, 6,057,287, 6,333,402, 7,628,983, and 8,283,321, 7,064,107, 7,276,480, 7,851,442, 8,124,586, 7,811,991, and U.S. Publication No. 20110086801, the entire contents of each of which is incorporated herein by reference. In some embodiments, the plasma kallikrein inhibitor is an inhibitory polypeptide or peptide. In some embodiments, the inhibitory peptide is ecallantide (also referred to as DX-88 or KALBITOR®; SEQ ID NO:80). In some embodiments, the kallikrein inhibitor comprises or consists of an about 58-amino acid sequence of amino acids 3-60 of SEQ ID NO: 80 or the DX-88 polypeptide having the 60-amino acid sequence of SEQ ID NO: 80.

Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO: 80).

The plasma kallikrein inhibitor can be full-length antibodies (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. The plasma kallikrein inhibitor can be recombinant proteins such as humanized, CDR grafted, chimeric, deimmunized, or in vitro generated antibodies, and may optionally include constant regions derived from human germline immunoglobulin sequences. In one embodiment, the plasma kallikrein inhibitor is a monoclonal antibody.

Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930 or lanadelumab), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04. In some embodiments, the plasma kallikrein binding protein is lanadelumab. See US 20110200611 and US 20120201756, which are incorporated by reference herein.

An example of a plasma kallikrein inhibitory antibody is lanadelumab. The amino acid sequences of the heavy chain and light chain variable regions of lanadelumab are provided below with the CDR regions identified in boldface and underlined.

Lanadelumab heavy chain variable region sequence
(SEQ ID NO: 81)
EVQLLESGGG LVQPGGSLRL SCAASGFTFS HYIMMWVRQA

PGKGLEWVSG IYSSGGITVY ADSVKGRFTI SRDNSKNTLY

LQMNSLRAED TAVYYCAYRR IGVPRRDEFD IWGQGTMVTV

SS

Lanadelumab light chain variable region sequence
(SEQ ID NO: 82)
DIQMTQSPS TLSASVGDRV TITCRASQSI SSWLAWYQQK

PGKAPKLLIY KASTLESGVP SRFSGSGSGT EFTLTISSLQ

PDDFATYYCQ QYNTYWTFGQ GTKVEI

In some embodiments, a plasma kallikrein inhibitor can have about 85%, 90%, 91%, 92%, 93%, 94%, 95%, 96%, 97%, 98%, 99% or higher sequence identity to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the constant region (e.g., CH1, CH2, CH3, and/or CL1) to a plasma kallikrein inhibitor described herein.

In some aspects, a small molecule binds and inhibits the active form of plasma kallikrein.

Bradykinin B2 Receptor Inhibitors

In some embodiments, a bradykinin B2 receptor inhibitor (e.g., antagonist) is administered to a subject. Exemplary bradykinin B2 receptor antagonists include icatibant (Firazyr®), which is a peptidomimetic drug containing 10 amino acids which block binding of native bradykinin to the bradykinin B2 receptor.

C1-INH Replacement Agents

In some embodiment, a C1 esterase inhibitor (C1-INH), such as a replacement C1-INH agent is administered to a subject. Exemplary C1-INH replacement agents are publicly available and include, for example, human plasma-derived C1-INH, e.g. Berinert® and CINRYZE®.

III. Kits for Detection of Cleaved HMWK

The present disclosure also provides kits for use in evaluating cleaved HMWK in samples suspected of containing a cleaved HWMK, e.g., biological samples from human patients. Such kits can comprise a first agent that specifically binds to cleaved HMWK as compared to intact HMWK or LMWK. In some embodiments, the first agent is an antibody, such as any of the antibodies described herein that specifically bind cleaved HMWK (e.g., 559B-M004 or functional variants thereof as described herein). In some embodiments, the kits further comprise a second agent (e.g., an antibody binding to HMWK) for detecting binding of the first agent to the cleaved HMWK. The second agent can be conjugated to a label. In some embodiments, the second agent is an antibody that specifically binds cleaved HMWK. In other embodiments, the second agent is an antibody that cross reacts with both cleaved and intact HMWK.

The kit may further comprise a support member for performing the immunoassay and immobilizing the first agent. In some embodiments, the support member is a 96-well plate, such as a 96-well ELISA plate. The kit can also comprise one or more buffers as described herein but not limited to a coating buffer; an assay buffer, such as an assay buffer containing $ZnCl_2$; a blocking buffer; a wash buffer; and/or a stopping buffer.

In some embodiments, the kit can comprise instructions for use in accordance with any of the methods described herein. The included instructions can comprise a description of how to use the components contained in the kit for measuring the level of cleaved and/or intact HMWK in a sample, which can be a biological sample collected from a human patient. Alternatively or in addition, the kit may comprise may comprise a description of how to use components contained in the kit for measuring the level of LMWK.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of cleaved and/or intact HMWK. In some embodiments, the kit is used for evaluating the level of LWMK. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

IV. Other Antibodies Binding to Cleaved HMWK

Also provided herein are isolated antibodies that bind both cleaved HMWK and intact HMWK. In some embodiments, such antibodies do not bind LMWK or bind to LMWK with a low affinity. In other embodiments, such antibodies also bind to LMWK.

In some embodiments, the antibodies that specifically binds a cleaved HMWK and intact HMWK (or additionally LMWK) described herein have a suitable binding affinity to one or more of the target antigens. The antibody described herein may have a binding affinity ($K_D$) of at least $10^{-5}$, $10^{-6}$, $10^{-7}$, $10^{-8}$, $10^{-9}$, $10^{-10}$ M, or lower.

Examples of the antibodies noted above and their binding specificities are provided in Table 2 in Example 2 below. The amino acid sequences of the heavy chain and light chain variable regions are provided below with the CDR regions identified in boldface and underlined (determined by one scheme as an example):

```
>559B-R0049-A01 (559B-M0067-E02) Heavy Chain Amino Acid Sequence
                                                    (SEQ ID NO: 6)
EVQLLESGGGLVQPGGSLRLSCAASGFTFSLYPMVWVRQAPGKGLEWVSSIYPSGGFTTYADSV

KGRFTISRDNSKNTLYLQMNSLRAEDTAVYYCARSSRYYYGMDVWGQGTTVTVSS

>559B-R0049-A01 (559B-M0067-E02) Light Chain Amino Acid Sequence
                                                    (SEQ ID NO: 7)
QYELTQPPSMSGTPGQRVTISCSGSSSNIGSEYVYWFQQLPGTAPKLLIYRNDQRPSGVPDRFS

GSKSGTSASLAISGLRSEDETDYYCSTWDDTLRTGVFGGGTKVTVL

>559B-R0049-G05 (559B-M0039-G07) Heavy Chain Amino Acid Sequence
                                                    (SEQ ID NO: 8)
EVQLLESGGGLVQPGGSLRLSCAASGFTFSRYRMRWVRQAPGKGLEWVSGISPSGGWTYYADSV

KGRFTISRDNSKNTLYLQMNSLRAEDTAVYYCTTDNGDYALAHWGQGTLVTVSS

>559B-R0049-G05 (559B-M0039-G07) Light Chain Amino Acid Sequence
                                                    (SEQ ID NO: 9)
QDIQMTQSPSSLSASVGDRVTITCRASQRIINYLNWYQQKPGKAPKLLIYAASSLQSGVPSRFS

GSGSGTDFTLTISSLQPEDFATYYCQQSYSAPLTFGGGTRVEIK

>559B-R0048-A09 (559B-M0044-E09) Heavy Chain Amino Acid Sequence
                                                    (SEQ ID NO: 10)
EVQLLESGGGLVQPGGSLRLSCAASGFTFSQYSMGWVRQAPGKGLEWVSSIYSSGGSTQYADSV

KGRFTISRDNSKNTLYLQMNSLRAEDTATYYCARTFRRGWFGEDYYYMDVWGKGTTVTVSS
```

```
>559B-R0048-A09 (559B-M0044-E09) Light Chain Amino Acid Sequence
                                               (SEQ ID NO: 11)
QDIQMTQSPSSLSASVGDRITITCRASQGIRNDVGWYQQKPGKAPQRLIYAASSLQSGVPSRFS

GSGSGTEFTLTISSLQPEDFATYYCLQHNSYPLTFGGGTKVEIK

>559B-R0048-E01 (559B-M0003-008) Heavy Chain Amino Acid Sequence
                                               (SEQ ID NO: 12)
EVQLLESGGGLVQPGGSLRLSCAASGFTFSPYMMYWVRQAPGKGLEWVSSISPSGGKTWYADSV

KGRFTISRDNSKNTLYLQMNSLRAEDTAVYYCARLGGSSSYYYYYYYGMDVWGQGTTVTVSS

>559B-R0048-E01 (559B-M0003-008) Light Chain Amino Acid Sequence
                                               (SEQ ID NO: 13)
QSALTQSPSASGTPGQRVTISCSGSSSNIGGNTVNWYQQFPGTAPKLLIYSNNQRPSGVPDRFS

GSKSGTSASLAISGLQSEDEAIYYCASWDDRLNGHWVFGGGTRLTVL

>559B-R0049-G01 (559B-M0039-H06) Heavy Chain Amino Acid Sequence
                                               (SEQ ID NO: 14)
EVQLLESGGGLVQPGGSLRLSCAASGFTFSAYDMHWVRQAPGKGLEWVSSIWPSGGGTYYADSV

KGRFTISRDNSKNTLYLQMNSLRAEDTAVYYCARGDYDYGDFTDAFDIWGQGTMVTVSS

>559B-R0049-G01 (559B-M0039-H06) Light Chain Amino Acid Sequence
                                               (SEQ ID NO: 15)
QSALTQPASVSGSPGQSITISCTGTSSDVGSYNLVSWYQQHPGKAPKLMIYEGSKRPSGVPDRF

SGSKSGNTASLIISGLQAEDEADYYCCSYAGSYSYVFGTGTRVTVL

>559B-R0049-E05 (559B-M0039-D08) Heavy Chain Amino Acid Sequence
                                               (SEQ ID NO: 16)
EVQLLESGGGLVQPGGSLRLSCAASGFTFSNYAMQWVRQAPGKGLEWVSWIYSSGGPTYYADSV

KGRFTISRDNSKNTLYLQMNSLRAEDTAVYYCARGLPGQPFDYWGQGTLVTVSS

>559B-R0049-E05 (559B-M0039-D08) Light Chain Amino Acid Sequence
                                               (SEQ ID NO: 17)
QSELTQPPSASGTPGQRVTISCSGSSSNIGNNYVYWYQQFPGTAPKLLIYRNNQRPSGVPDRFS

GSKSGTSASLAISGLRSEDEADYYCATWDDRLSGWVFGGGTKLTVL

>559B-R0048-A11 (559B-M0068-007) Heavy Chain Amino Acid Sequence
                                               (SEQ ID NO: 18)
EVQLLESGGGLVQPGGSLRLSCAASGFTFSSYQMHWVRQAPGKGLEWVSGIYSSGGSTPYADSV

KGRFTISRDNSKNTLYLQMNSLRAEDTAVYYCARGHHGMDVWGQGT TVTVSS

>559B-R0048-A11 (559B-M0068-007) Light Chain Amino Acid Sequence
                                               (SEQ ID NO: 19)
QDIQMTQSPSSVSASVGDRVTITCRASQGISSWLAWYQQKPGKAPKLLIYAASNLQSGVPSRFS

GSGSGTDFTLTISSLQPEDFATYYCQKYNIAPYTFGQGTKLEIK

>559B-R0048-A03 (559B-M0021-G11) Heavy Chain Amino Acid Sequence
                                               (SEQ ID NO: 20)
EVQLLESGGGLVQPGGSLRLSCAASGFTFSPYPMTWVRQAPGKGLEWVSGISSSGGFTPYADSV

KGRFTISRDNSKNTLYLQMNSLRAEDTAVYYCARMVRGVIKAFDIWGQGTMVTVSS

>559B-R0048-A03 (559B-M0021-G11) Light Chain Amino Acid Sequence
                                               (SEQ ID NO: 21)
QYELTQPPSASGTPGQRVTISCSGSSSNIGSHYVFWYQQLPGAAPKLLIYRNNQRPSGVPDRFS

GSKSGTSASLAISGLRSEDEADYYCATWDNSLSAWVFGGGTKLTVL

>559B-R0048-005 (559B-M0061-G06) Heavy Chain Amino Acid Sequence
                                               (SEQ ID NO: 22)
EVQLLESGGGLVQPGGSLRLSCAASGFTFSKYTMWWVRQAPGKGLEWVSVISSSGGKTYYADSV

KGRFTISRDNSKNTLYLQMNSLRAEDTAVYYCARTANRAFDIWGQGTMVTVSS

>559B-R0048-005 (559B-M0061-G06) Light Chain Amino Acid Sequence
                                               (SEQ ID NO: 23)
QDIQMTQSPAALSVSPGERATLSCRASQSVSSDLAWYQQKPGQAPRLLIHGASTRATGIPARFS

GSGSGREFTLTISSLQSEDFAVYYCQQYNDWPPLFGPGTKVNIK
```

-continued

>559B-R0049-A03 (559B-M0036-G12) Heavy Chain Amino Acid Sequence
(SEQ ID NO: 24)
EVQLLESGGGLVQPGGSLRLSCAASGFTFSRYYMAWVRQAPGKGLEWVSGIVPSGGQTGYADSV
KGRFTISRDNSKNTLYLQMNSLRAEDTAVYYCARTRRGWFGEDYYYYMDVWGKGTLVTVSS >559B-R0049-A03 (559B-M0036-G12) Light Chain Amino Acid Sequence
(SEQ ID NO: 25)
QDIQMTQSPGILSLSPGERATVSCRASQSVGSTYLAWYQHKPGQAPRLLIYGASSRATGIPDRF
SGSGSGTDFTLTISSLEPEDFAIYYCQHFHTSPPGITFGQGTRLEIK >559B-R0048-009 (559B-M0042-E06) Heavy Chain Amino Acid Sequence
(SEQ ID NO: 26)
EVQLLESGGGLVQPGGSLRLSCAASGFTFSMYKMSWVRQAPGKGLEWVSVISPSGGRTYYADSV
KGRFTISRDNSKNTLYLQMNSLRAEDTAVYYCARGTRTSGLDYWGQGTLVTVSS >559B-R0048-009 (559B-M0042-E06) Light Chain Amino Acid Sequence
(SEQ ID NO: 27)
QSALTQPASVSGSPGQSITISCTGTSSDVGGYKYVSWYQQHPGKAPKLVIYEVSNRPSGVSNRF
SGSKSGNTASLTISGLQAEDEADYYCSSYTSSTTVVFGGGTKLTVL >559B-R0048-E09 (559B-M0070-H10) Heavy Chain Amino Acid Sequence
(SEQ ID NO: 28)
EVQLLESGGGLVQPGGSLRLSCAASGFTFSTYGMRWVRQAPGKGLEWVSVISPSGGKTNYADSV
KGRFTISRDNSKNTLYLQMNSLRAEDTAVYYCARGRPDYYAMDVWGQGTTVTVSS >559B-R0048-E09 (559B-M0070-H10) Light Chain Amino Acid Sequence
(SEQ ID NO: 29)
QSALTQPPSASGAPGQRVTISCSGSSSNIGSNTVNWYQKLPGTAPKLLIYYNDRRPSGVPDRFS
GSKSGNTASLIISGLQAEDEADYYCAAWDDSLSGPVFGGGTKLTVL >559B-R0048-E05 (559B-M0068-D01) Heavy Chain Amino Acid Sequence
(SEQ ID NO: 30)
EVQLLESGGGLVQPGGSLRLSCAASGFTFSIYPMSWVRQAPGKGLEWVSGISPSGGKTAYADSV
KGRFTISRDNSKNTLYLQMNSLRAEDTAVYYCARGQGRAVRGKLYYYGMDVWGQGTTVTVSS >559B-R0048-E05 (559B-M0068-D01) Light Chain Amino Acid Sequence
(SEQ ID NO: 31)
QSALTQPPSASQTPGQTVTISCSGSSSNIGTNNVNWYQQLPGTAPKLLISSHHRRPSGVPDRFS
ASKSGTSASLAISGLQSEDEADYYCAAWDDSLNGPVFGGGTKLTVL >559B-R0048-001 (559B-M0004-E08) Heavy Chain Amino Acid Sequence
(SEQ ID NO: 32)
EVQLLESGGGLVQPGGSLRLSCAASGFTFSMYHMNWVRQAPGKGLEWVSSIYSSGGSTRYADSV
KGRFTISRDNSKNTLYLQMNSLRAEDTAVYYCARGVRYGMDVWGQGTTVTVSS >559B-R0048-001 (559B-M0004-E08) Light Chain Amino Acid Sequence
(SEQ ID NO: 33)
QDIQMTQSPSSVSASVGDRVTITCRASQGISSWLAWYQQKPGKAPKLLIYAASSLQSGVPSRFS
GSGSGTDFTLTISSLQPEDFATYYCQQANSFPITFGQGTRLEIK >559B-R0049-001 (559B-M0069-009) Heavy Chain Amino Acid Sequence
(SEQ ID NO: 34)
EVQLLESGGGLVQPGGSLRLSCAASGFTFSMYDMHWVRQAPGKGLEWVSSISSSGGYTQYADSV
KGRFTISRDNSKNTLYLQMNSLRAEDTAMYYCARDRGLIAAAGGFDPWGQGTLVTVSS >559B-R0049-001 (559B-M0069-009) Light Chain Amino Acid Sequence
(SEQ ID NO: 35)
QDIQMTQSPSSLSASVGDRVTITCRASQSIGIYLNWYQQKPGTAPKLLIYAASSLQSGVPSRFT
GSGSGTDFTLTISSLQPDDFATYYCQRTYGRPLTFGGGTKVEIK >559B-R0049-A05 (559B-M0038-F04) Heavy Chain Amino Acid Sequence
(SEQ ID NO: 36)
EVQLLESGGGLVQPGGSLRLSCAASGFTFSKYEMMWVRQAPGKGLEWVSSISPSGGYTMYADSV
KGRFTISRDNSKNTLYLQMNSLRAEDTAVYYCARHRSKWNDAPFDSWGQGTLVTVSS -continued >559B-R0049-A05 (559B-M0038-F04) Light Chain Amino Acid Sequence
(SEQ ID NO: 37)
QDIQMTQSPSSLSASVGDRVAITCRASQSIDTYLNWYQQKPGKAPKLLIYAASKLEDGVPSRFS

GSGTGTDFTLTIRSLQPEDFASYFCQQSYSSPGITFGPGTKVEIK

>559B-R0048-G05 (559B-M0044-O05) Heavy Chain Amino Acid Sequence
(SEQ ID NO: 38)
EVQLLESGGGLVQPGGSLRLSCAASGFTFSIYQMYWVRQAPGKGLEWVSSIYSSGGRTFYADSV

KGRFTISRDNSKNTLYLQMNSLRAEDTAVYYCATRGSWYVGGNEYFQHWGQGTLVTVSS

>559B-R0048-G05 (559B-M0044-O05) Light Chain Amino Acid Sequence
(SEQ ID NO: 39)
QSVLTQSPSLSLSPGQTASIPCSGDTLGNKFVSWYQQKPGQSPVLVIYQDTKRPSGIPERFSGS

NSGNTATLTITGTQAMDEADYYCQVWDSNSYAFGPGTKVTVL

>559B-R0048-C11 (559B-M0047-H01) Heavy Chain Amino Acid Sequence
(SEQ ID NO: 40)
EVQLLESGGGLVQPGGSLRLSCAASGFTFSFYMMYWVRQAPGKGLEWVSSISSSGGFTRYADSV

KGRFTISRDNSKNTLYLQMNSLRAEDTAVYYCARVRGLAVAAPDYWGQGTLVTVSS

>559B-R0048-C11 (559B-M0047-H01) Light Chain Amino Acid Sequence
(SEQ ID NO: 41)
QSELTQPASVSGSPGQSITISCIGTSSDIGTYNYVSWYQQHPGKAPKLMIYDVNTRPSGVSDRF

SGSKSGNTASLTISGLQAEDEADYYCSSYTTSVTWVFGGGTTLTVL

>559B-R0048-0O3 (559B-M0019-E12) Heavy Chain Amino Acid Sequence
(SEQ ID NO: 42)
EVQLLESGGGLVQPGGSLRLSCAASGFTFSGYNMYWVRQAPGKGLEWVSRISPSGGWTSYADSV

KGRFTISRDNSKNTLYLQMNSLRAEDTAVYYCTRGQWMDWWGQGTMVIVSS

>559B-R0048-0O3 (559B-M0019-E12) Light Chain Amino Acid Sequence
(SEQ ID NO: 43)
QDIQMTQSPSSLSASVGDRVIITCRASQNITGYLNWYQQKPGKAPNLLIYDASRMNTGVPSRFR

GSGSGTDYILTIYKLEPEDIGTYFCQHTDDFSVTFGGGTKVDLK

>559B-R0048-A05 (559B-X0004-B05) Heavy Chain Amino Acid Sequence
(SEQ ID NO: 44)
EVQLLESGGGLVQPGGSLRLSCAASGFTFHYRMMWVRQAPGKGLEWVSYISSSGGYTAYADSVK

GRFTISRDNSKNTLYLQMNSLRAEDTAVYYCAAKRNRAFDIWGQGTMVIVSS

>559B-R0048-A05 (559B-X0004-B05) Light Chain Amino Acid Sequence
(SEQ ID NO: 45)
QDIQMTQSPDSLAVSLGERATINCKSSQSVLYSSNNKNYLAWYQQKPGQPPKLLIYWASTRESG

VPDRFSGSGSGTDFTLTISSLQAEDVAVYYCQQYYSTPLGFGQGTKLEIK

>559B-R0048-E11 (559B-M0048-D12) Heavy Chain Amino Acid Sequence
(SEQ ID NO: 46)
EVQLLESGGGLVQPGGSLRLSCAASGFTFSRYQMTWVRQAPGKGLEWVSIGSSGGFTNYADSV

KGRFTISRDNSKNTLYLQMNSLRAEDTAVYYCARLPANFYYYMDVWGKGTTVTVSS

>559B-R0048-E11 (559B-M0048-D12) Light Chain Amino Acid Sequence
(SEQ ID NO: 47)
QDIQMTQSPSSLSASVGDRVTITCRASQNIYSFLNWYQQKPGKAPKLLIYATSSLQSGVPSRFS

GSGSGTDFTLTISSLQPEDFASYYCQQNYNIPWTFGQGTKVEIK

>559B-R0048-G11 (559B-M0053-G01) Heavy Chain Amino Acid Sequence
(SEQ ID NO: 48)
EVQLLESGGGLVQPGGSLRLSCAASGFTFSWYMMKWVRQAPGKGLEWVSSIVPSGGWTTYADSV

KGRFTISRDNSKNTLYLQMNSLRAEDTAVYYCATEGNLWFGEGRAFDIWGQGTMVTVSS

>559B-R0048-G11 (559B-M0053-G01) Light Chain Amino Acid Sequence
(SEQ ID NO: 49)
QDIQMTQSPGILSLSPGERATLSCRASQSVSSSYLAWYQQKPGQAPRLLIYGASSRATGIPDRF

SGSGSGTDFTLTISRLEPEDFAVYYCQQRSNWPPSFGQGTRLDIK

-continued

>559B-R0049-005 (559B-M0038-H03) Heavy Chain Amino Acid Sequence
(SEQ ID NO: 50)
EVQLLESGGGLVQPGGSLRLSCAASGFTFSKYDMHWVRQAPGKGLEWVSRISSSGGKTEYADSV
KGRFTISRDNSKNTLYLQMNSLRAEDTAVYYCAREYRYCTANTCSLYGMDVWGRGTTVTVSS >559B-R0049-005 (559B-M0038-H03) Light Chain Amino Acid Sequence
(SEQ ID NO: 51)
QDIQMTQSPSSLSASVGDRVAITCRTSQGVRSDFAWYQQTPGKAPRRLIYAAFILDNGVPSRFS
GSGSGTEFTLTISSLQPEDFATYYCQQSYSTPLTFGGGTKVEMK >559B-R0048-E03 (559B-M0017-H08) Heavy Chain Amino Acid Sequence
(SEQ ID NO: 52)
EVQLLESGGGLVQPGGSLRLSCAASGFTFSPYWMHWVRQAPGKGLEWVSVISPSGGGTGYADSV
KGRFTISRDNSKNTLYLQMNSLRAEDTAVYYCARESRGSGSHEDYWGQGTLVTVSS >559B-R0048-E03 (559B-M0017-H08) Light Chain Amino Acid Sequence
(SEQ ID NO: 53)
QDIQMTQSPATLSLSPGERATLSCRASQSVSSYLAWYQQKPGQAPRLLIYGASNRGTGIPARFS
GSGSGTEFTLTISSLQSEDFAVYFCQQYKNWPNLTFGGGTKVDIK >559B-R0049-E03 (559B-M0035-F05) Heavy Chain Amino Acid Sequence
(SEQ ID NO: 54)
EVQLLESGGGLVQPGGSLRLSCAASGFTFSHYPMAWVRQAPGKGLEWVSGIVSSGGRTVYADSV
KGRFTISRDNSKNTLYLQMNSLRAEDTAVYYCARDPYDFWSEGAFDIWGQGTMVTVSS >559B-R0049-E03 (559B-M0035-F05) Light Chain Amino Acid Sequence
(SEQ ID NO: 55)
QSVLTQPPSASGTPGQRVTISCSGSSSNIGNNFVYWYHQVPGTAPKLLIYKNNQRPSGVPDRFS
GSKSAASASLAISGLRSEDEADYYCAAWDNSLSGFYVFGAGTKVTVL >559B-R0049-G03 (559B-M0035-H09) Heavy Chain Amino Acid Sequence
(SEQ ID NO: 56)
EVQLLESGGGLVQPGGSLRLSCAASGFTFSWYGMHWVRQAPGKGLEWVSRIGPSGGPTSYADSV
KGRFTISRDNSKNTLYLQMNSLRAEDTAVYYCARGYYGTGRYFQHWGQGTLVTVSS >559B-R0049-G03 (559B-M0035-H09) Light Chain Amino Acid Sequence
(SEQ ID NO: 57)
QDIQMTQSPDSLSLSPGDRATLSCRASQSVGSDYLAWYQQKPGQAPRLLIYDASNRATGIPARF
SGSGSGTDFTLTISSLEPEDFAVYYCQQRSNWPPTFGGGTKVEIK >559B-R0048-A07 (559B-M0043-006) Heavy Chain Amino Acid Sequence
(SEQ ID NO: 58)
EVQLLESGGGLVQPGGSLRLSCAASGFTFSAYAMRWVRQAPGKGLEWVSYISSSGGETMYADSV
KGRFTISRDNSKNTLYLQMNSLRAEDTAVYYCANGYGRIDYWGQGTLVTVSS >559B-R0048-A07 (559B-M0043-006) Light Chain Amino Acid Sequence
(SEQ ID NO: 59)
QSVLTQPASVSGSPGQSITISCTGTSSDIGGYNYVSWYQQHPGKAPKLMIYEVSNRPSGVSNRF
SGSKSGNTASLTISGLQAEDEADYYCSSYTSGSTRVFGIGTRVTVL >559B-R0048-G01 (559B-M0003-A08) Heavy Chain Amino Acid Sequence
(SEQ ID NO: 60)
EVQLLESGGGLVQPGGSLRLSCAASGFTFSAYVMRWVRQAPGKGLEWVSSIGSSGGPTYYADSV
KGRFTISRDNSKNTLYLQMNSLRAEDTAVYYCARRGSGSSHAFDIWGQGTMVTVSS >559B-R0048-G01 (559B-M0003-A08) Light Chain Amino Acid Sequence
(SEQ ID NO: 61)
QDIQMTQSPSSLSASVGDRVTITCRASQSISSYLNWYQQKPGKAPKLLIYAASSLQSGVPSRFS
GSGSGTDFTLTISSLQPEDSGTYYCQQYNSFPLTFGGGTKVEIK >559B-R0048-G09 (559B-M0054-B11) Heavy Chain Amino Acid Sequence
(SEQ ID NO: 62)
EVQLLESGGGLVQPGGSLRLSCAASGFTFSYYGMNWVRQAPGKGLEWVSVISPSGGLTVYADSV
KGRFTISRDNSKNTLYLQMNSLRAEDTAMYYCATGFAVQHGGGAFDIWGQGTMVTVSS

```
>559B-R0048-G09 (559B-M0054-B11) Light Chain Amino Acid Sequence
                                                    (SEQ ID NO: 63)
QDIQMTQSPATLSMSPGERATLSCRASQSVTTYLAWYQQKPGQAPRLLIYDASIRATGVPARFS

GSGSGTDFTLTISRLEPEDFAVYYCQQRTIWPLTFGGGTKVEIK

>559B-R0048-E07 (559B-M0067-G11) Heavy Chain Amino Acid Sequence
                                                    (SEQ ID NO: 64)
EVQLLESGGGLVQPGGSLRLSCAASGFTFSPYEMVWVRQAPGKGLEWVSSIVPSGGWTVYADSV

KGRFTISRDNSKNTLYLQMNSLRAEDTAVYYCASPSGRGLAFDIWGQGTMVTVSS

>559B-R0048-E07 (559B-M0067-G11) Light Chain Amino Acid Sequence
                                                    (SEQ ID NO: 65)
QDIQMTQSPGILSLSPGERATLSCRASQSISSSYLAWYQQKPGQAPRLLIYGASSRATGVPDRF

SGSGSGTEFTLTISSLQPEDFATYYCLQQKSYPYTFGQGTKVEIK

>559B-R0048-007 (559B-M0065-B10) Heavy Chain Amino Acid Sequence
                                                    (SEQ ID NO: 66)
EVQLLESGGGLVQPGGSLRLSCAASGFTFSKYFMTWVRQAPGKGLEWVSWISSSGGYTNYADSV

KGRFTISRDNSKNTLYLQMNSLRAEDTAVYYCARGAYYYDAFDIWGQGTMVTVSS

>559B-R0048-007 (559B-M0065-B10) Light Chain Amino Acid Sequence
                                                    (SEQ ID NO: 67)
QDIQMTQSPSSLSASVGDRVTITCRASQSIAIFLNWYQQTPGKPPKLLIYGASTLQSGVPSRFS

GSGSGADFTLTISNLQLEDFTTYYCQQSYSTLYTFGQGTKLEIK

>559B-R0049-O03 (559B-M0037-E08) Heavy Chain Amino Acid Sequence
                                                    (SEQ ID NO: 68)
EVQLLESGGGLVQPGGSLRLSCAASGFTFSRYSMSWVRQAPGKGLEWVSVISSSGGMTYYADSV

KGRFTISRDNSKNTLYLQMNSLRAEDTAMYYCARDYYGNMDVWGKGTTVTVSS

>559B-R0049-O03 (559B-M0037-E08) Light Chain Amino Acid Sequence
                                                    (SEQ ID NO: 69)
QDIQMTQSPSSLSTSVGDRVTITCRTSQDISGALAWYQQKPGKAPRLLIFGASSLESGVPSRFS

GSGSGTDFTLTISSLQPEDFATYYCQQFNKYPLTFGGGTKVEIK

>559B-R0049-E01 (559B-M0035-A01) Heavy Chain Amino Acid Sequence
                                                    (SEQ ID NO: 70)
EVQLLESGGGLVQPGGSLRLSCAASGFTFSWYTMGWVRQAPGKGLEWVSYIYPSGGYTMYADSV

KGRFTISRDNSKNTLYLQMNSLRAEDTAVYYCANPYSSGGYWGQGTLVTVSS

>559B-R0049-E01 (559B-M0035-A01) Light Chain Amino Acid Sequence
                                                    (SEQ ID NO: 71)
QDIQMTQSPLSLPVTPGEPASISCRSSQSLLDSNGYNYLDWFLQKPGQSPQLLIYLGFNRASGV

PDRFSGSGSGTDFTLKISRVEAEDVGVYYCMQALQTPYTFGQGTKLEIT

>559B-R0048-G03 (559B-M0003-E08) Heavy Chain Amino Acid Sequence
                                                    (SEQ ID NO: 72)
EVQLLESGGGLVQPGGSLRLSCAASGFTFSAYLMTWVRQAPGKGLEWVSGISPSGGITKYADSV

KGRFTISRDNSKNTLYLQMNSLRAEDTAVYYCARDIPNWIYGMDVWGQGTTVTVSS

>559B-R0048-G03 (559B-M0003-E08) Light Chain Amino Acid Sequence
                                                    (SEQ ID NO: 73)
QSALTQPPSVSVSPGQTASITCSGDKLGNKYASWYQQKPGQSPVLVIYQDRRRPSGIPERFSGS

NSGNTATLTISGTQAMDEADYYCQAWDSGVVFGGGTKLTVL

>559B-R0048-G07 (559B-M0052-E02) Heavy Chain Amino Acid Sequence
                                                    (SEQ ID NO: 74)
EVQLLESGGGLVQPGGSLRLSCAASGFTFSNYLMLWVRQAPGKGLEWVSGISPSGGGTAYADSV

KGRFTISRDNSKNTLYLQMNSLRAEDMAVYYCAKVAYSGSYYYYYMDVWGKGTTVTVSS

>559B-R0048-G07 (559B-M0052-E02) Light Chain Amino Acid Sequence
                                                    (SEQ ID NO: 75)
QDIQMTQSPSSLSASVGDRVTITCRASQSISSYLNWYQQKPGKAPKLLIYAASSLQSGVPSRFS

GSGSGTDFTLTISSLQPEDFATYYCQQSYSTHSITFGQGTRLEIK
```

-continued

>559B-M0064-H02 Heavy Chain Amino Acid Sequence
(SEQ ID NO: 76)
EVQLLESGGGLVQPGGSLRLSCAASGFTFSQYIMGWVRQAPGKGLEWVSSIGSSGVTVYADSVK

GRFTISRDNSKNTLYLQMNSLRAEDTAVYYCARGGGVTVLHAFDIWGQGTMVTVSSASTKGPSV

FPLAPSSKS

>559B-M0064-H02 Light Chain Amino Acid Sequence
(SEQ ID NO: 77)
QSALTQPASVSGSPGQSITISCTGTSSDVGGYNYVSWYQQHPGKVPKLIIYEGNKRPSGVPDRF

SGSKAGNTASLTVSGLQAEDEADYYCTAYGGHSRFYVFGTGTKVTVLGQPKANP

Also within the scope of this disclosure are functional equivalents of any of the exemplary antibodies listed above. Such a functional equivalent may bind to the same epitope of a cleaved HMWK and/or intact HMWK, or the sample epitope of LMWK as one of the above listed exemplary antibodies. In some embodiments, the functional equivalent competes against one of the above-listed exemplary antibodies for binding to a target antigen.

In some embodiments, the functional equivalent comprises a $V_H$ chain that includes a $V_H$ CDR1, a $V_H$ CDR2, and/or a $V_H$ CDR3 at least 75% (e.g., 80%, 85%, 90%, 95%, 96%, 97%, 98%, or 99%) identical to the corresponding $V_H$ CDRs of one of the above-listed exemplary antibodies. Alternatively or in addition, the functional equivalent comprises a $V_L$ CDR1, a $V_L$ CDR2, and/or a $V_L$ CDR3 at least 75% (e.g., 80%, 85%, 90%, 95%, 96%, 97%, 98%, or 99%) identical to the exemplary antibody as listed above. In some embodiments, the functional equivalent has the same heavy chain and/or light chain complementarity determining regions (CDRs) as one of the above-listed exemplary antibodies.

Alternatively or in addition, the functional equivalent comprises a $V_H$ chain at least 75% (e.g., 80%, 85%, 90%, 95%, 96%, 97%, 98%, or 99%) identical to the $V_H$ chain of an exemplary antibody and/or a $V_L$ chain at least 75% (e.g., 80%, 85%, 90%, 95%, 96%, 97%, 98%, or 99%) identical to the $V_L$ chain of the exemplary antibody.

In some instances, the functional equivalent may contain one or more (e.g., up to 5, up to 3, or up to 1) conservative mutations in one or more of the heavy chain CDRs, or one or more of the light chain CDRs in an exemplary antibody, e.g., at positions where the residues are not likely to be involved in interacting with a target antigen.

Without further elaboration, it is believed that one skilled in the art can, based on the above description, utilize the present present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Development of Immunoassays for Specific Detection of Cleaved HMWK

An ELISA-based immunoassay screen was initially developed to identify Fab fragments in a phage display library that bound to cleaved or intact HMWK. In general, the assay conditions relied on biotinylated intact or cleaved HMWK immobilized on streptavidin coated 384-well assay plates, blocking using a bovine serum albumin (BSA) blocking buffer, and contacting the immobilized HMWK with Fab displayed on phage from an overnight culture in *E. coli* (detected with anti-M13-HRP antibody).

Figure 12:
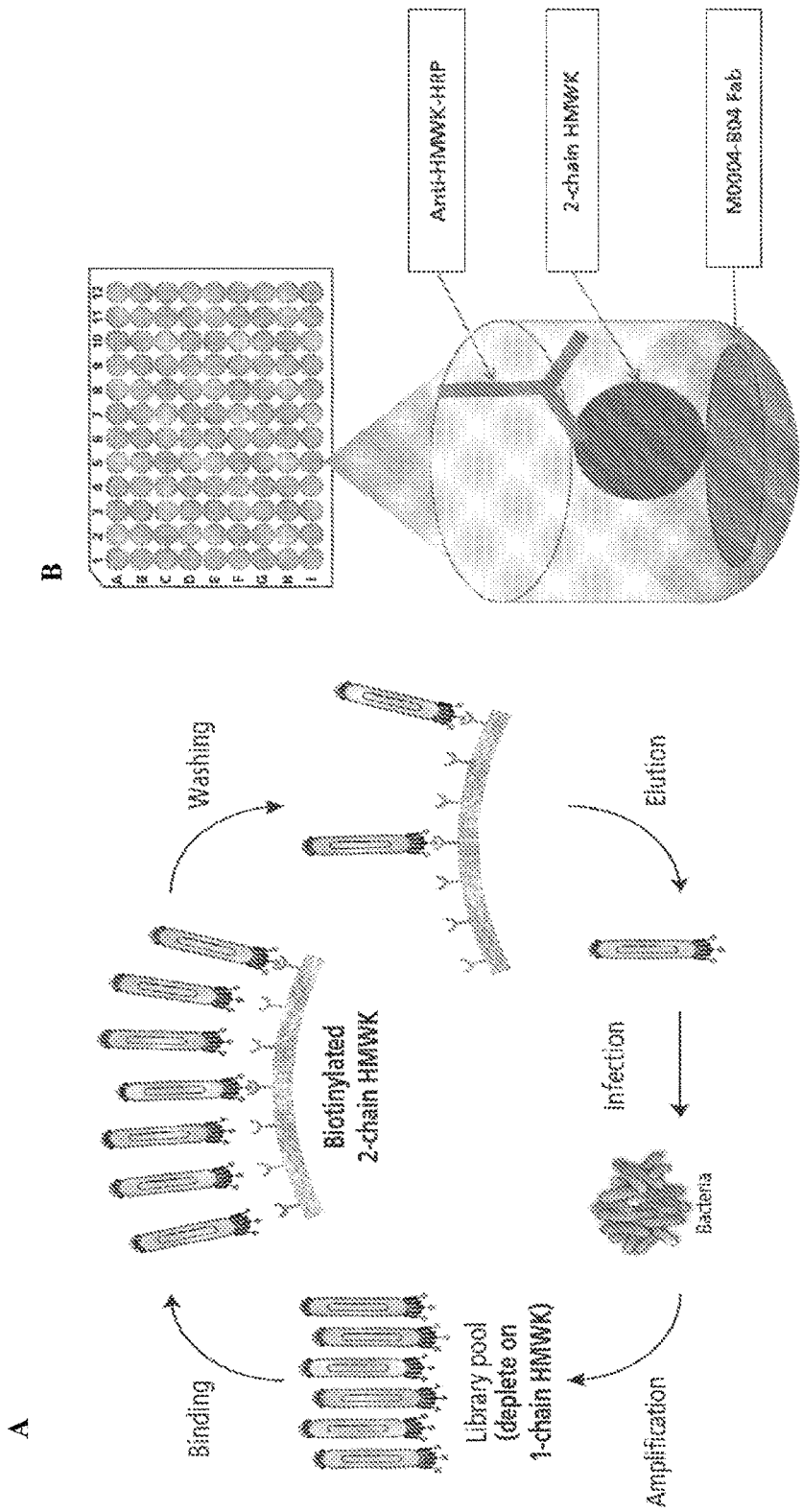
FIG. 12 presents schematics of the discovery and development of assays using the antibodies described herein. A: schematic of the phage display methods used to discover 2-chain HMWK binding antibodies. B: an example sandwich ELISA assay in which the 2-chain HMWK specific antibody/Fab (e.g., 559B-M0004-B04) is immobilized in 96-well plates to capture 2-chain HMWK in citrated plasma, followed by washing and detection with an anti-HMWK antibody conjugated to a label (anti-HMWK-HRP).
Figure 13:
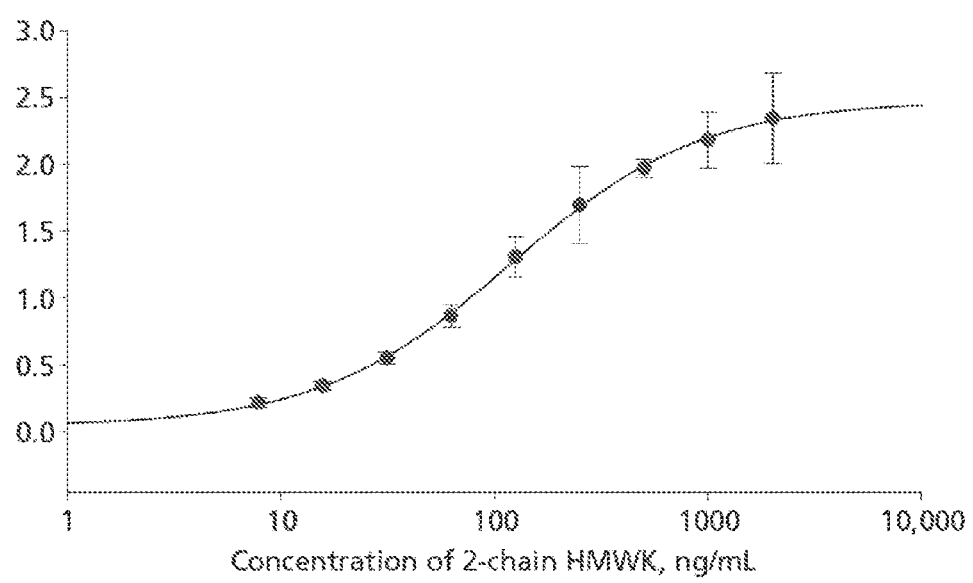
FIG. 13 is a graph showing results from a 2-chain HMWK sandwich ELISA standard curve, in which citrated plasma samples were spiked with 2-chain HMWK (10% final dilution).

As shown in FIG. 12, panel A, the selection was directed towards obtaining 2-chain HMWK specific antibodies by first preforming a negative selection of the library with an input of approximately $1 \times 10^{12}$ phage against biotinylated 1-chain HMWK immobilized streptavidin coated magnetic beads (Dynabeads M280, Thermo Fisher). The depleted library was then contacted with biotinylated 2-chain HMWK immobilized on streptavidin coated magnetic beads. The beads were extensively washed with PBS buffer and used to infect *E. coli* for phage output amplification to complete a round of selection. Three rounds of selection were performed prior to screening individual phage colonies by ELISA with biotinylated 1-chain and 2-chain HMWK immobilized on streptavidin coated plates followed by detection with horse radish peroxidase (HRP) conjugated anti-M13 antibody and absorbance detection due to substrate hydrolysis for 3,3',5,5'-Tetramethylbenzidine (TMB). Recombinant Fab fragments were expressed in *E. coli* and purified by protein A sepharose chromatography (Wassaf et al. *Anal. Biochem.* (2006) 351: 241-253). The specificity of each purified Fab was determined by coating 384 well plates and measuring binding to biotinylated 1-chain HMWK, to biotinylated 2-chain HMWK, or to biotinylated LMWK, followed by detection with streptavidin conjugated to HRP and TMB detection. These assay conditions led to the identification of the 559B-M004-B04 isolate, which specifically binds cleaved HMWK over intact HMWK (FIG. 1).

The immobilized HMWK was also contacted with a crude (unpurified) 559B-M004-B04 Fab preparation from an overnight culture in *E. coli*. Fab bound to the HMWK was detected using an anti-human Fab-HRP antibody, but did not result in specific binding to cleaved HMWK (FIG. 1).

The configuration of the immunoassay was reversed by passively immobilizing the purified Fab fragment of 559B-M004-B04 on polystyrene 384-well assay plate. The Fab was contacted with biotinylated HMWK, and the bound HMWK were detected with streptavidin-HRP. (FIG. 1).

Figure 1:
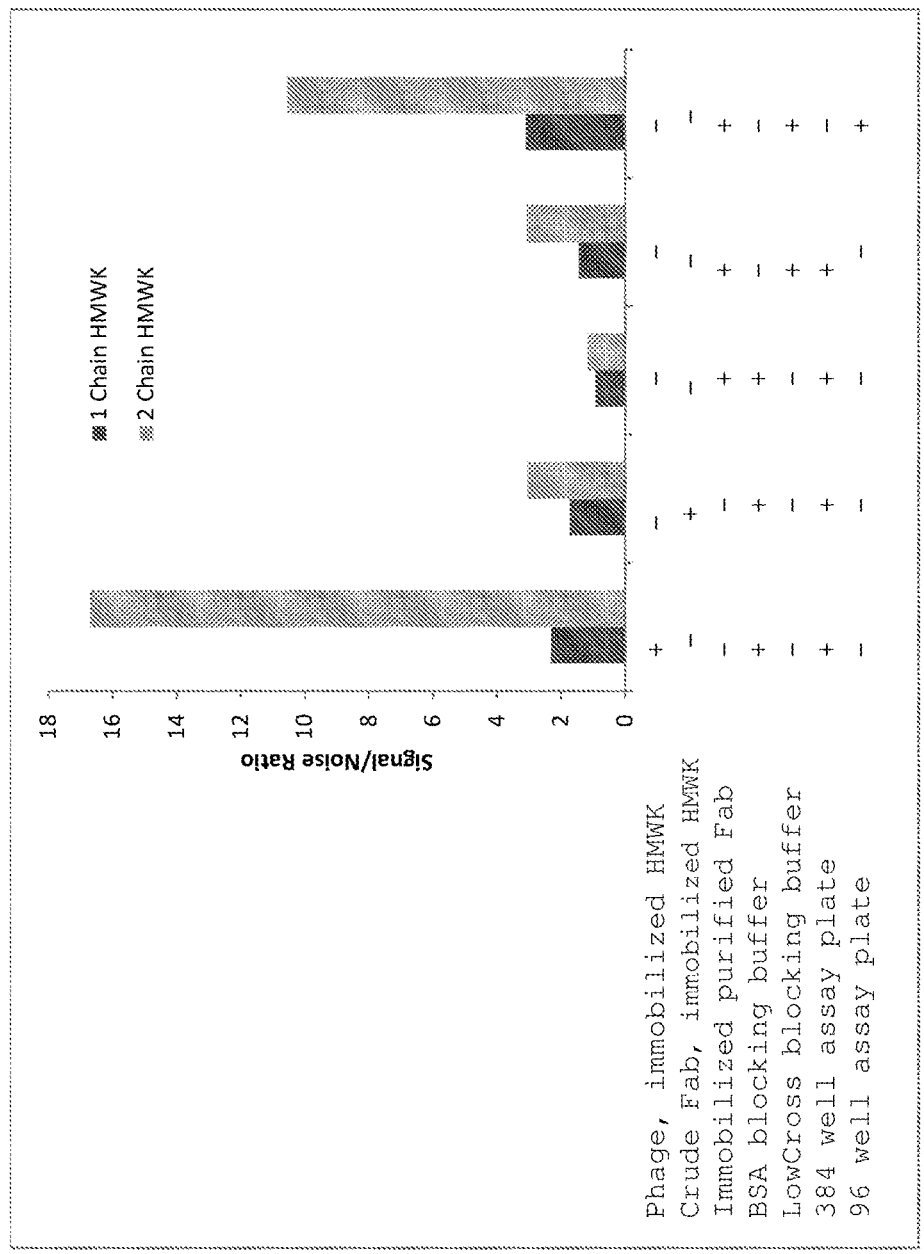
FIG. 1 is a graph showing binding of 559B-M0004-B04 to intact HMWK (dark gray bars) or cleaved HMWK (light gray bars) under the indicated ELISA conditions.

Unexpectedly, the specificity of the 559B-M004-B04 Fab to cleaved HMWK was enhanced when the BSA blocking buffer was replaced with a commercially available blocking buffer, the LowCross Blocking Solution from Candor Biosciences during the initial screening analyses (FIG. 1). Further, performing the immunoassay using 96-well assay plates rather than 384-well plates further increased the observed specificity of 559B-M004-B04 to cleaved HMWK (FIG. 1).

The results obtained using the 559B-M004-B04 isolate led to the development of an immunoassay (ELISA) for the detection of 2-HMWK in samples (FIG. 12, panel B). This assay can also be used to further evaluate binding characteristics of other Fab fragments and antibodies. Briefly, a Fab is coated on to a multiwell plate overnight. The following day the plate is washed then blocked with BSA Buffer. Following a wash samples, standards, and QCs diluted in LowCross Buffer are added to the plate and after a subsequent incubation and then wash, any bound 2-Chain HMWK is detected by adding HRP-labeled sheep anti-HMWK polyclonal detection antibody. Following incubation with the detection antibody, the plate is washed and TMB substrate is added to the plate. After a short incubation the reaction is stopped with phosphoric acid. The optical density is then measured at 450 nm-630 nm.

Figure 2:
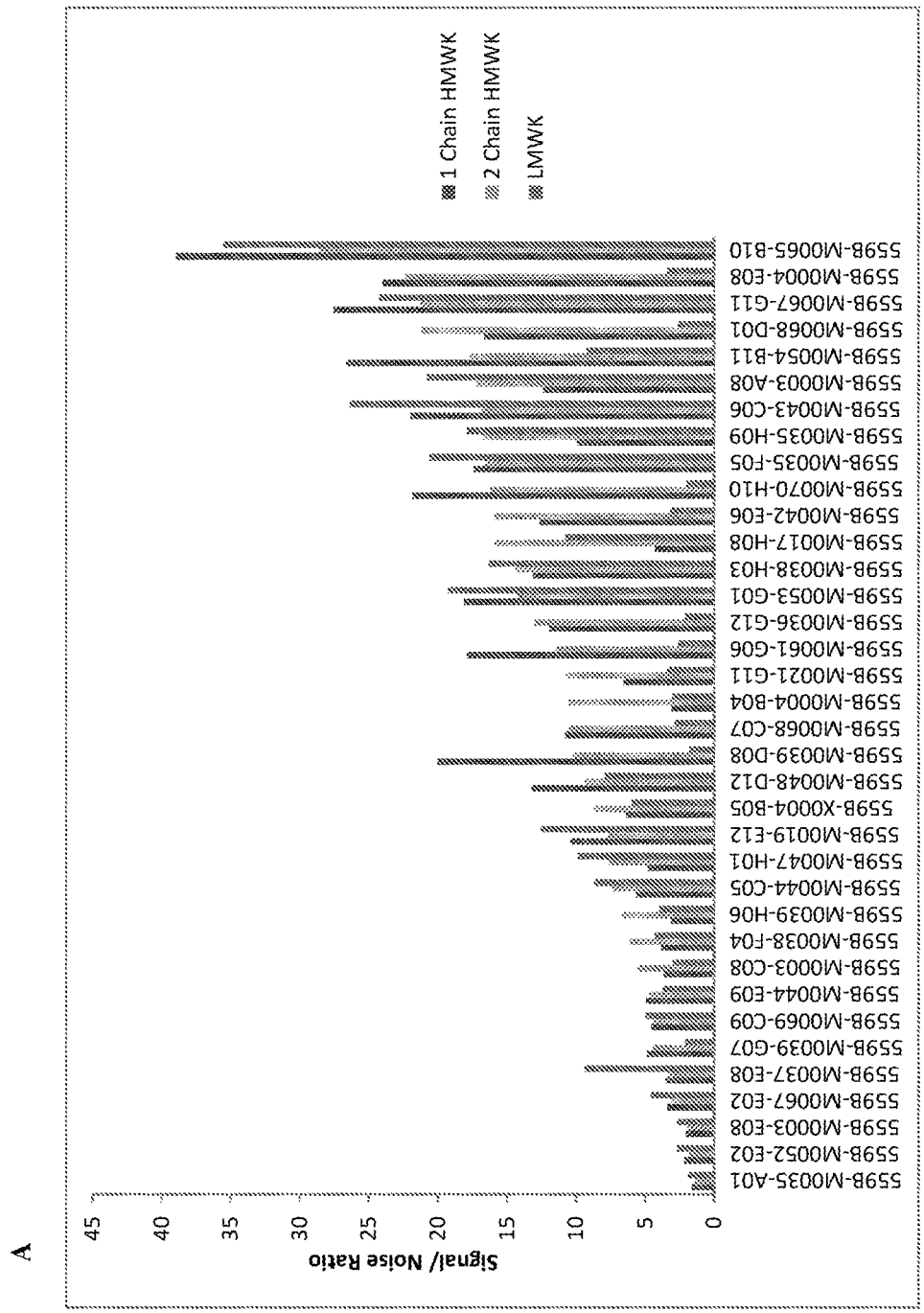
FIG. 2 presents graphs showing binding of various Fab clones to intact 1-chain (intact) HMWK, 2-chain (cleaved) HMWK, or LMWK. A: Fab clones identified using the phage display screening methods described herein. Intact HWMK is shown in dark gray bars, cleaved HMWK in light gray bars, and LMWK in medium gray bars. B: binding for several example Fab clones. LWMK is shown in dark gray bars, intact HMWK in light gray bars, and cleaved HWMK in medium gray bars.
Figure 2:
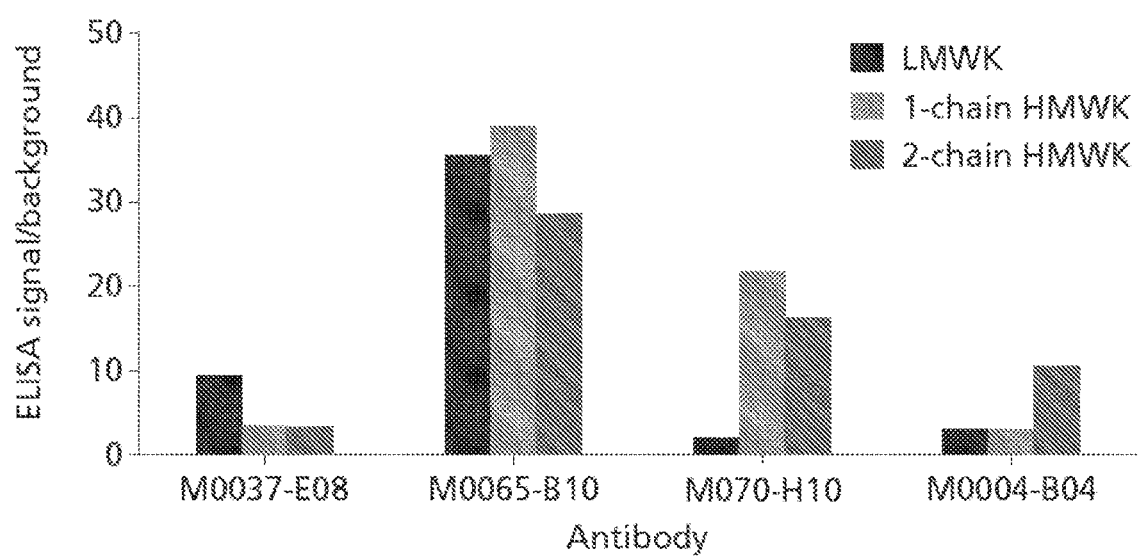

Example 2: Evaluation of Binding Specificity of Fab Clones Using Immunoassays Described Herein Thirty-six purified Fab clones (see Table 2 below) were assessed for binding to cleaved HWMK, intact HMWK, and LWMK using the immunoassay described in Example 1. Specifically, each of the purified Fab clones was immobilized on 96-well assay plates at a concentration of 1 μg/L) in a total volume of 100 μL in PBS and incubated overnight at 2-8° C. The assay plates were blocked using LowCross blocking buffer. Biotinylated intact HMWK, biotinylated cleaved HMWK or biotinylated LMWK (1 μg/L each) was added to each well in a total volume of 100 μL and incubated for 2 hours prior to washing with a wash buffer. HRP-labeled streptavidin was added to each well at a concentration of 100 ng/mL, and the signal was developed using Ultra TMB Substrate. The signal to noise ratio was calculated using the signal observed upon the addition of the biotinylated protein to an uncoated well. (FIG. 2, panels A and B). Based on the ELISA results, the antibodies can be divided among 5 categories (Table 2).

TABLE 2

Binding characteristics of Fab fragments

| ELISA Binding | Fab Fragment |
|---|---|
| Low affinity binder | 559B-M0035-A01, 559B-M0052-E02, 559B-M0003-E08 |
| Bind to cleaved and intact HMWK, not LMWK | 559B-M0067-E02, 559B-M0039-G07, 559B-M0044-E09, 559B-M0003-C08, 559B-M0039-H06, 559B-M0039-D08, 559B-M0068-C07, 559B-M0021-G11, 559B-M0061-G06, 559B-M0036-G12, 559B-M0042-E06, 559B-M0070-H10, 559B-M0068-D01, 559B-M0004-E08 |
| Bind to cleaved and intact HMWK and LMWK | 559B-M0069-C09, 559B-M0038-F04, 559B-M0044-C05, 559B-M0047-H01, 559B-M0019-E12, 559B-X0004-B05, 559B-M0048-D12, 559B-M0053-G01, 559B-M0038-H03, 559B-M0017-H08, 559B-M0035-F05, 559B-M0035-H09, 559B-M0043-C06, 559B-M0003-A08, 559B-M0054-B11, 559B-M0067-G11, 559B-M0065-B10, 559B-M0064-H02 |
| Mainly bind to LMWK | 559B-M0037-E08 |
| Specifically Bind to cleaved HMWK | 559B-M0004-B04 |

Several antibodies were obtained that bound to both 1-chain, 2-chain HMWK and LMWK, such as 559B-M0064-H02. These antibodies are likely to bind an epitope in domains 1 through 4, which are shared between HMWK and LMWK. M070-H10 is an example of an antibody presumed to bind an epitope shared between 1-chain and 2-chain HMWK but not on LMWK. LMWK is a kininogen splice variant leads to a truncated protein composed of domains 1 through 4 and part of domain 5 (Colman et al. *Blood* (1997) 90: 3819-3843). Consequently, antibodies such as M070-H10 are likely to bind domain 5 or domain 6.

Figure 3:
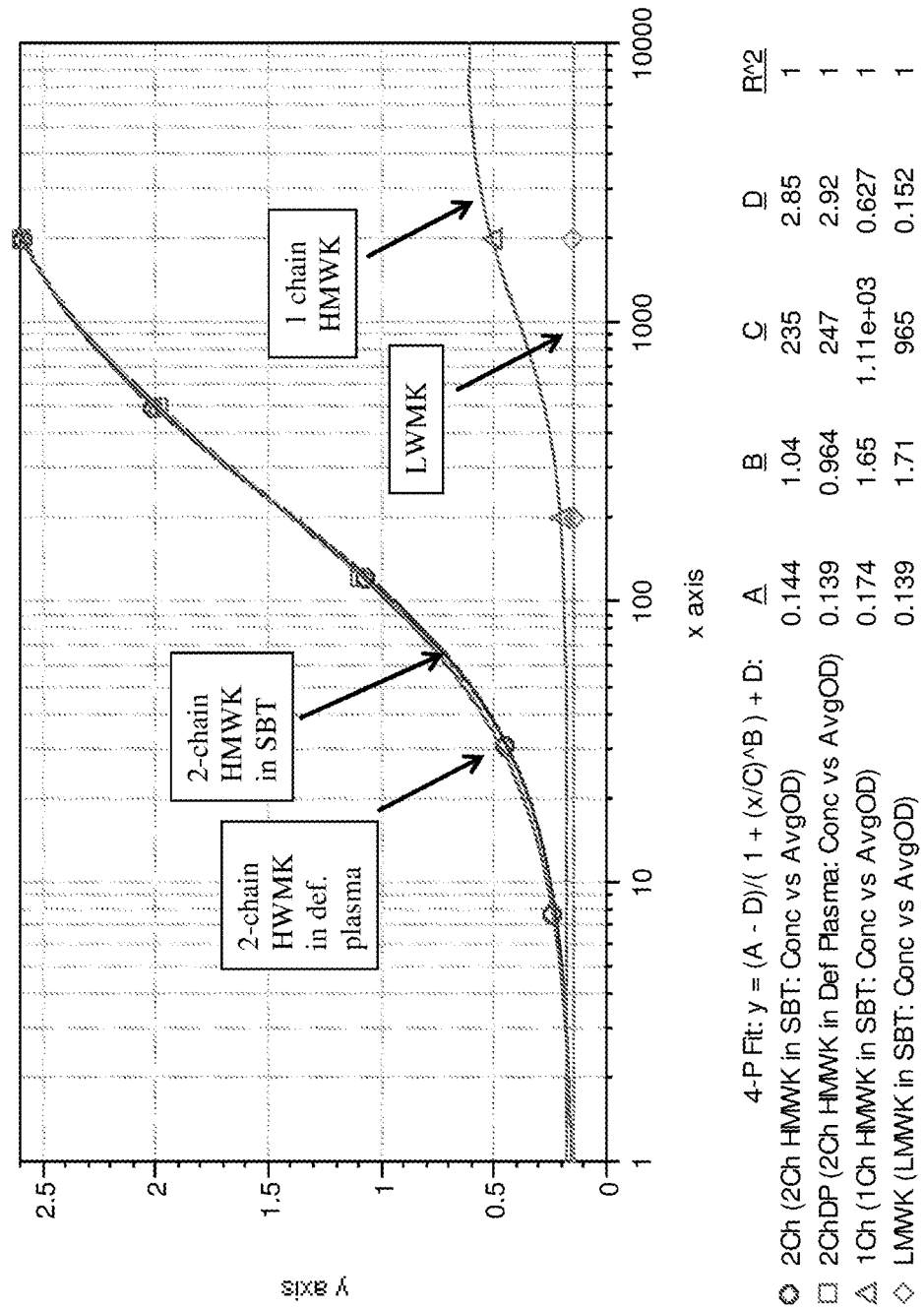
FIG. 3 is a graph showing specificity of 559B-M0004-B04 towards intact HMWK, cleaved HMWK, or LMWK. Purified cleaved HMWK was spiked into SBT assay buffer (circles) or HMWK-deficient plasma (squares). Purified intact HMWK was spiked into SBT assay buffer (triangles). Purified LMWK was spiked into SBT assay buffer (diamonds). The y-axis presents the ELISA signal in absorbance units, and the x-axis presents the concentration of kininogen in µg/mL.
Figure 4:
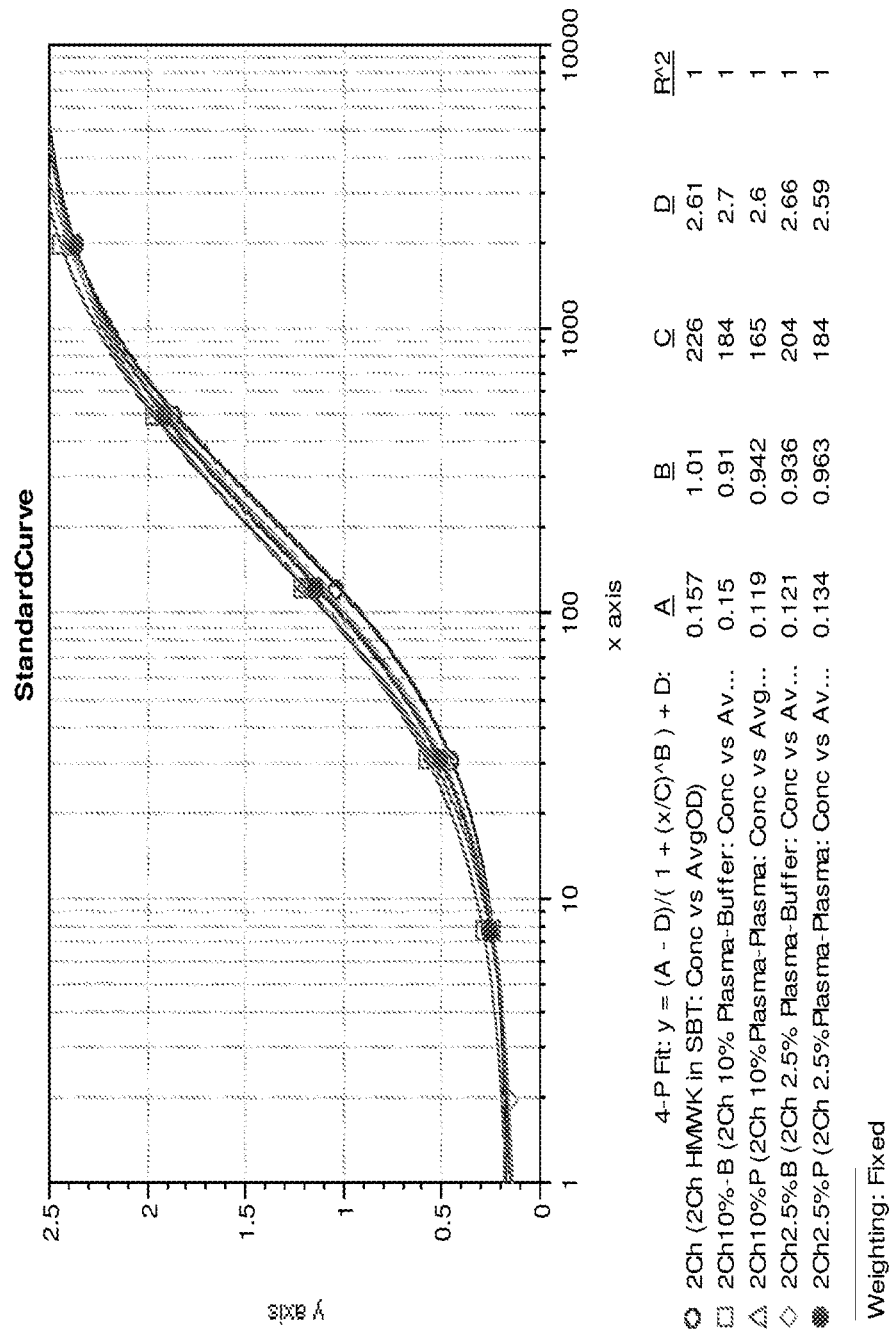
FIG. 4 is a graph showing detection of 2-Chain HMWK (cleaved HMWK) in plasma or assay buffer. Purified cleaved HMWK was spiked into SBT assay buffer (open circles), SBT assay buffer and analyzed in the presence of 10% plasma (squares), or HMWK-deficient plasma and analyzed in the presence of 10% plasma (triangles). Purified cleaved HMWK was also spiked into assay buffer and analyzed in the presence of 2.5% plasma (diamonds) or HMWK deficient plasma and analyzed in the presence of 2.5% plasma (closed circles). The y-axis presents the ELISA signal in absorbance units, and the x-axis presents the concentration of kininogen in µg/mL.
Figure 14:
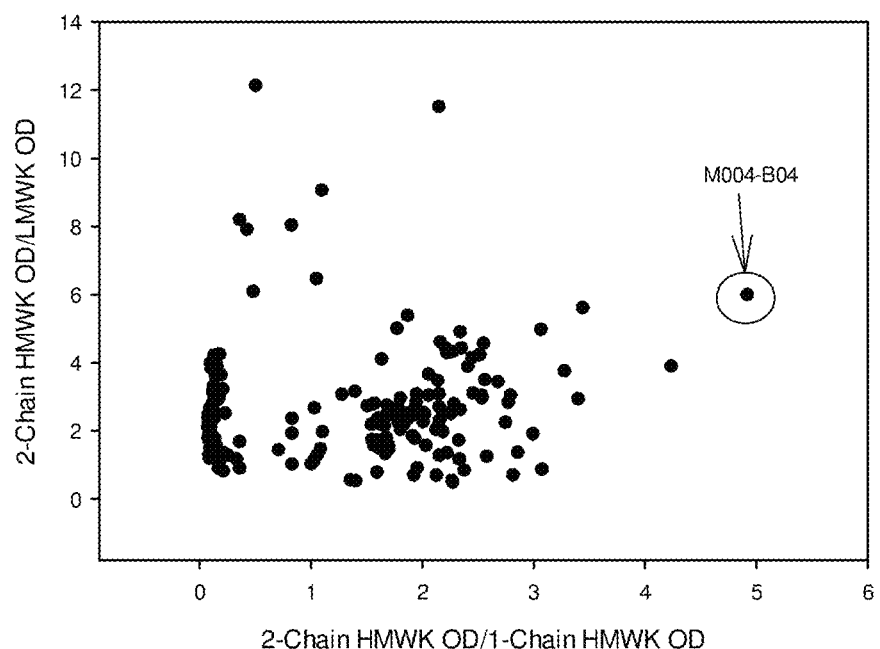
FIG. 14 shows the identification of 2-chain HMWK-specific antibodies by phage display selection and screening.
Figure 14:
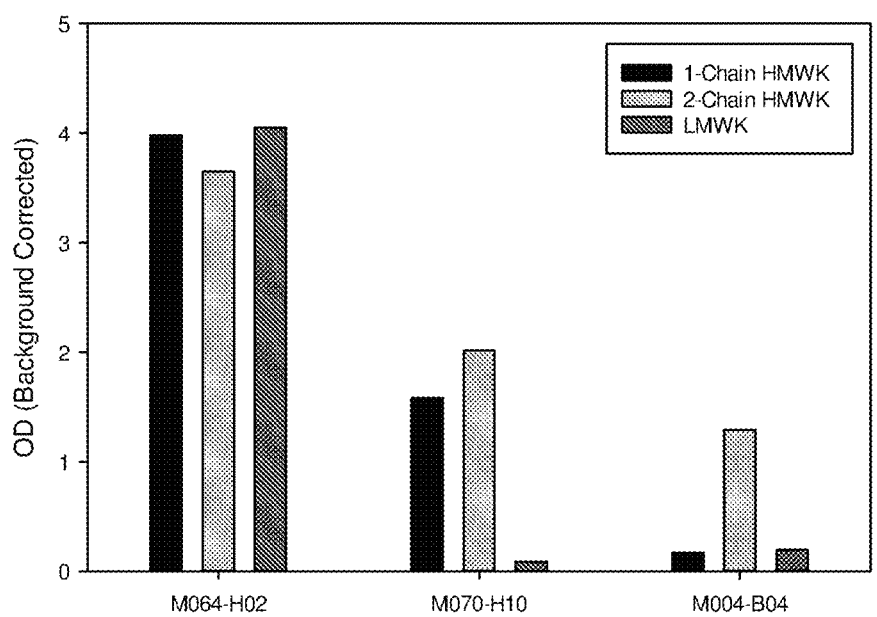

As shown in FIG. 14, panel A, 559B-M0004-B04 exhibited selectivity for 2-chain over both 1-chain HMWK and LMWK and was selected for further assay optimization. A sandwich ELISA was developed to detect cleaved HMWK in human plasma samples in which 559B-M0004-B04 (100 μL of 2 μg/mL) was passively immobilized on a 96 well plate (Nunc Maxisorp plate) (FIG. 12, panel B). The following day, the plate was washed and then blocked with 2% BSA (Protease/IgG free) in PBS buffer. Following a wash, samples containing cleaved HMWK in 0.1% BSA buffer in PBS with 0.05% Tween-20 (2-Chain HMWK assay buffer). Purified protein standards (e.g., 2-chain HMWK, intact HMWK or LMWK) were spiked into HNKW HMWK-deficient plasma and diluted 1:320 in 2-chain HMWK assay buffer. Following plate washing with PBST, a mixture of 2 mouse monoclonal antibodies (11H05 and 13B12) at 1 μg/mL in 2-chain HMWK assay buffer were added for 1 hour at room temperature. Unbound detection antibodies were washed and a 1:2000 dilution of goat anti-mouse secondary antibody conjugated to horseradish peroxidase (HRP) was added. The assay containing the secondary antibody was incubated for 1 hour at room temperature, and unbound secondary antibody was removed by washing with 2-chain HMWK assay buffer. Signal was detected by the addition of 3, 3',5,5'-tetramethylbenzidine (TMB), an HRP substrate. The reaction was stopped with phosphoric acid. Hydrolysis of a TMB substrate was detected using a microplate reader at 450 nm-630 nm (FIG. 3). Additionally, performing the ELISA assay using samples containing cleaved HMWK in 2-chain HMWK assay buffer buffer or HMWK-deficient plasma and analyzed in the presence of either 2.5% or 10% plasma resulted in similar binding (FIG. 4). Using these immunoassay conditions, specifically binding to cleaved HMWK was detected. The assay resulted in comparable performance when HMWK was provided in either 2-chaim HMWK assay buffer or HMWK-deficient plasma (FIGS. 3 and 4). Furthermore, there was no binding of 559B-M0004-B04 to LMWK.

Figure 5:
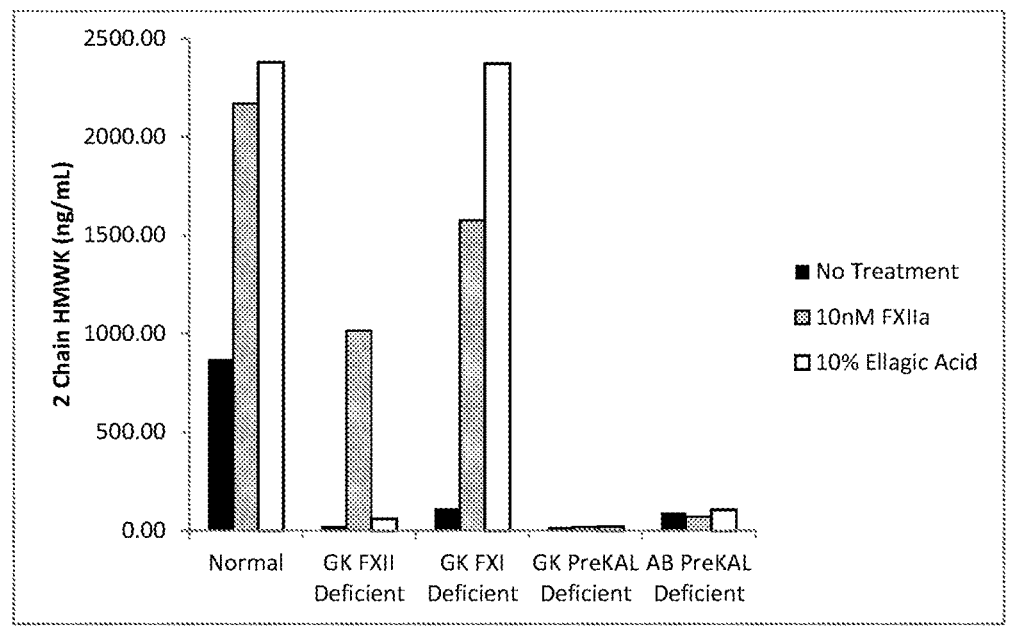
FIG. 5 is a graph showing levels of cleaved HMWK in the indicated human plasma samples prior to and after contact system activation. A: prior to and after contact system activation with FXIIa or ellagic acid. B: prior to and after contact system activation with FXIIa, pKal, or ellagic acid.
Figure 5:
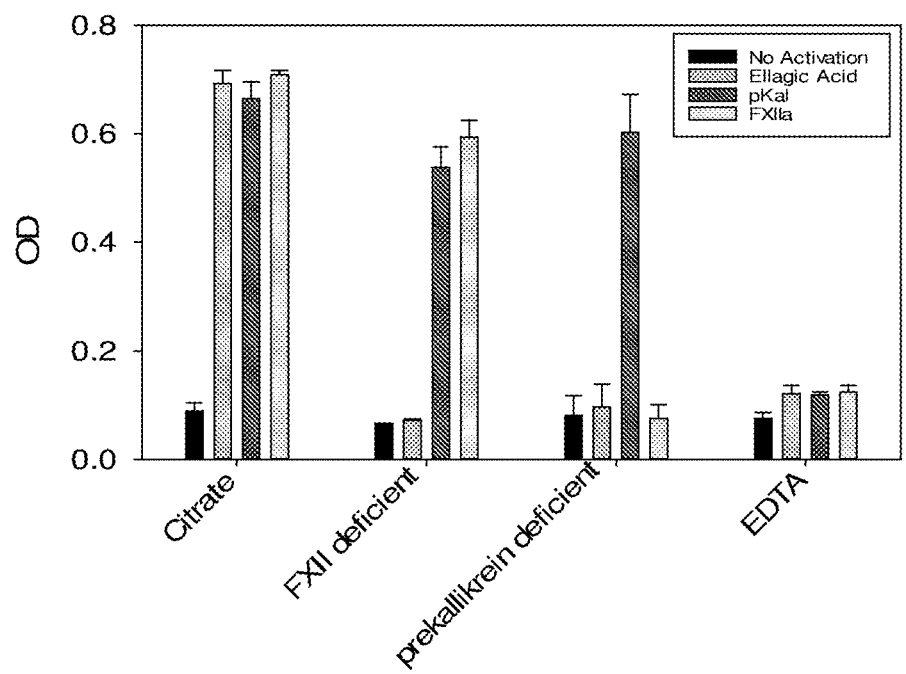

The ELISA assay was evaluated for detection of cleaved HMWK generated upon contact activation in human plasma (FIGS. 5A and 5B). The amount of cleaved HMWK in normal human plasma was measured in the absence or presence of a catalytic amount of FXIIa, pKal, or ellagic acid, which causes FXII auto-activation to FXIIa and consequently generation of cleaved HMWK (FIG. 5, panels A and B). Consistent with the role of plasma kallikrein as the primary plasma enzyme required for the generation of 2-chain HMWK, neither ellagic acid nor FXIIa addition lead to the generation of cleaved HMWK in prekallikrein-deficient plasma. The contact system in FXI deficient plasma was equally activated using either FXIIa, pKal, or ellagic; a result consistent with the understanding that FXIa is generated by FXIIa and does not produce 2-chain HMWK.

Figure 10:
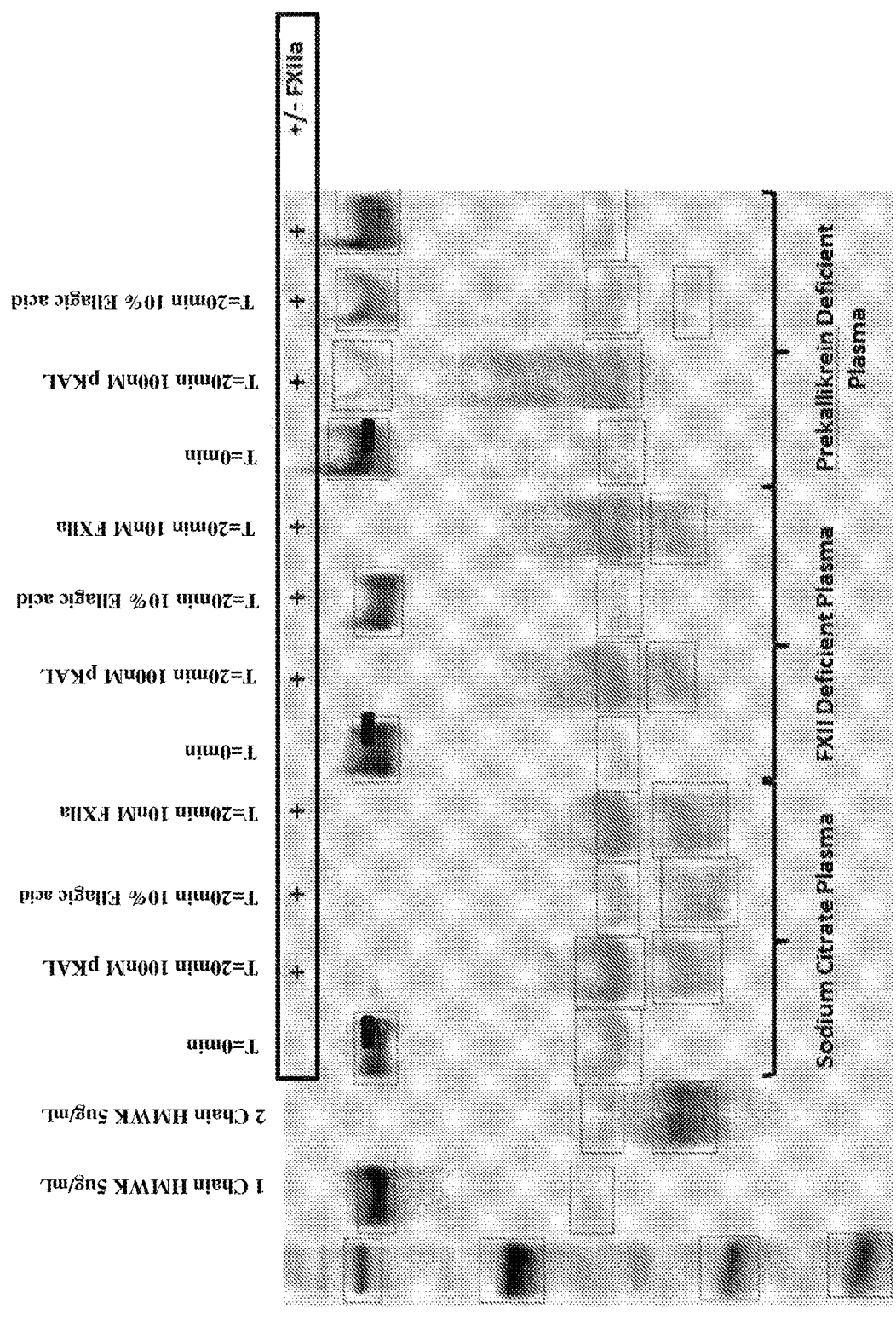
FIG. 10 is photo showing results obtained from a HMWK Western blot analysis, which are consistent with the results obtained from the 2-Chain HMWK ELISA assay described herein. Human citrated plasma samples (normal plasma, FXII-deficient plasma, and prekallikrein-deficient plasma) were probed with a mouse monoclonal anti-HMWK light chain antibody followed by a goat anti-mouse detection antibody. The analyzed plasma samples were either untreated or activated with 100 nM pKal, 10 nM FXIIa, or 10% ellagic acid.

The results from the 2-Chain HMWK ELISA were corroborated by detecting cleaved HMWK generated upon contact activation in human plasma by Western blot analysis using the mouse monoclonal antibody, 11H05 (FIG. 10). The 11H05 antibody specifically binds the light chain of HMWK and illuminates both the 56 kDa light chain and the further proteolyzed 46 kDa light chain, which is subsequently generated through the proteolytic activity of plasma kallikrein at a site near the N-terminus of the HMWK light chain (Colman et al. *Blood* (1997) 90: 3819-3843).

Figure 6:
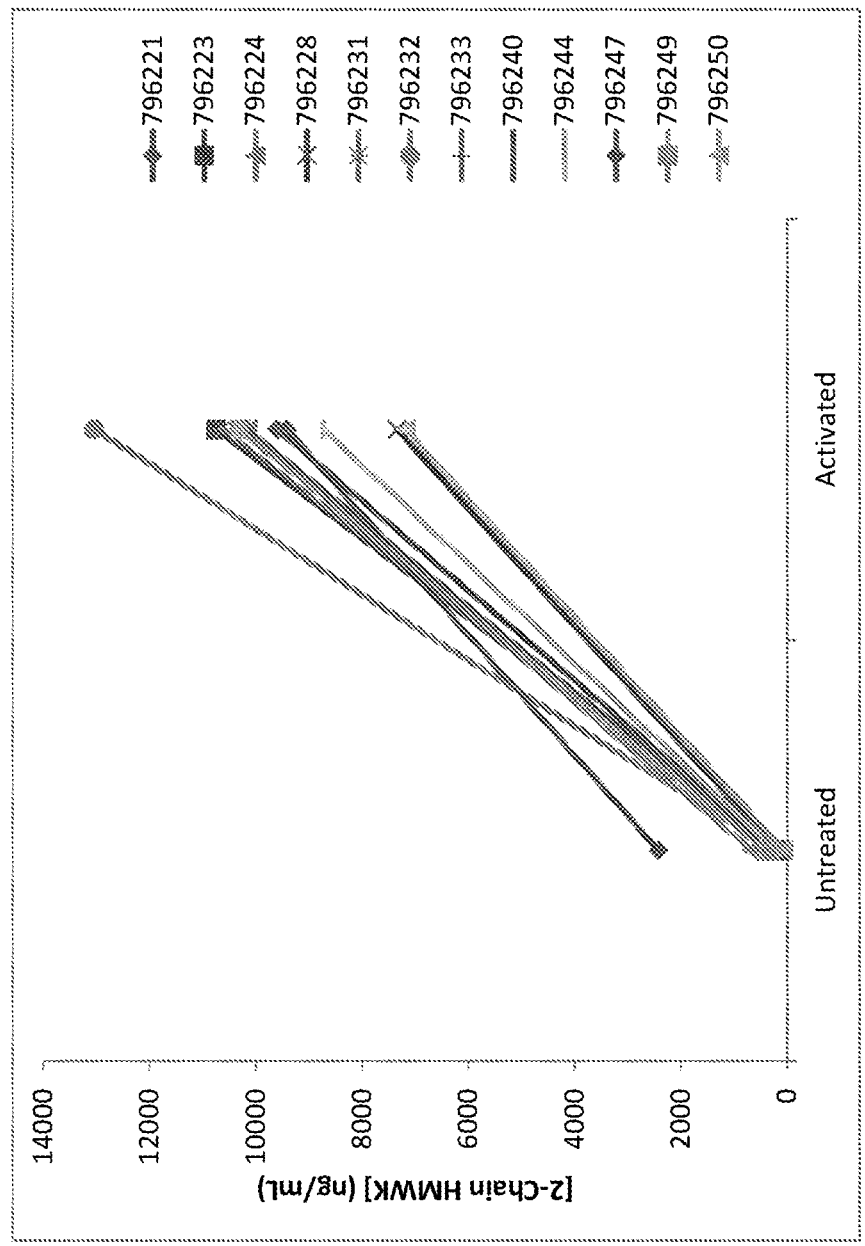
FIG. 6 is a graph showing levels of cleaved HMWK in plasma samples from 12 normal human donors prior to and after activation of the contact system with ellagic acid.
Figure 7:
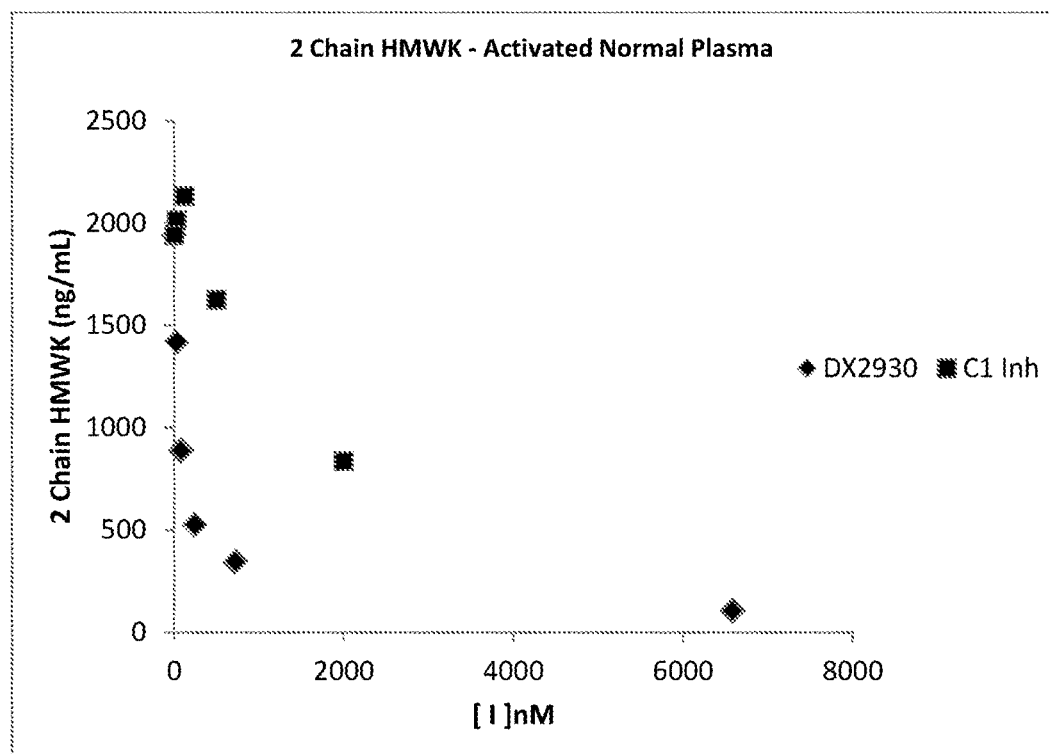
FIG. 7 presents graphs showing levels of cleaved HMWK following inhibition with a pKal inhibitor. A: inhibition with landadelumab/DX-2930 or C1-INH prior to contact system activation with ellagic acid. B: inhibition of pooled sodium citrate plasma samples with landadelumab/DX-2930 prior to contact system activation with 10 nM FXIIa.
Figure 7:
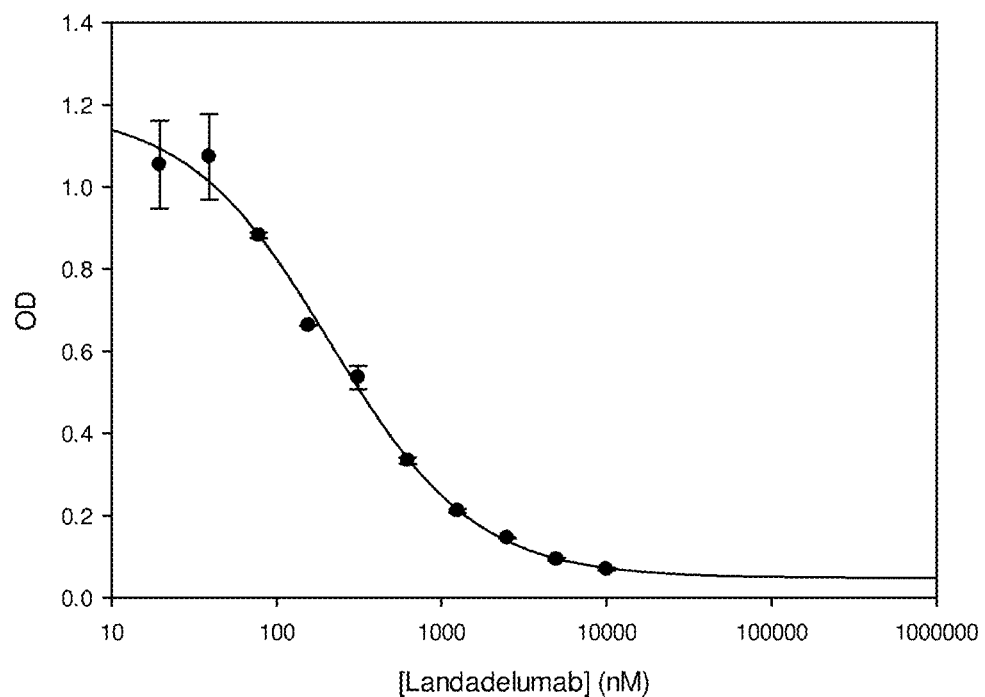

The ELISA assay was also evaluated for the ability to detect cleaved HMWK generated in plasma from 12 normal donors (FIG. 6). Following ellagic acid activation of the contact activation system, cleaved HMWK was detected in each of the 12 samples. The amount of cleaved HMWK was also measured after the contact activation system was inhibited in normal plasma using various concentrations of lanadelumab (DX-2930; a specific inhibitor of plasma kallikrein) or an inhibitor of the serpin C1-INH, then activated with ellagic acid (FIG. 7, panels A and B). Landadelumab (DX-2930) is a fully human antibody potent ($K_1=0.12$ nM) and specific inhibitor of plasma kallikrein that was discovered using phage and is in clinical development for the prophylactic treatment of HAE-C1INH attacks (Chyung et al. *Ann. Allergy Asthma Immunol.* (2014) 113: 460-466; Kenniston et al. *J. Biol. Chem.* (1994) 289: 23596-23608). When lanadelumab was spiked into citrated plasma at different concentrations it effectively inhibited the generation of 2-chain HMWK induced by FXIIa as shown by Western blot and sandwich ELISA (FIG. 7B). The $IC_{50}$ for lanadelumab inhibition of 2-chain HMWK generation was 212±28 nM, which is consistent with the value expected for the activation of all prekallikrein in neat plasma (approximately 500 nM). The complete inhibition of signal by landadelumab in plasma treated with a contact system activator confirms that M004-B04 is specific for 2-chain HMWK generated by plasma kallikrein.

Activation of the contact system in kininogen-deficient plasma did not yield an increase in ELISA signal in this preliminary assay using M004-B04 as the capture antibody and a HRP-conjugated sheep polyclonal anti-kininogen as the detection antibody (data not shown).

Figure 11:
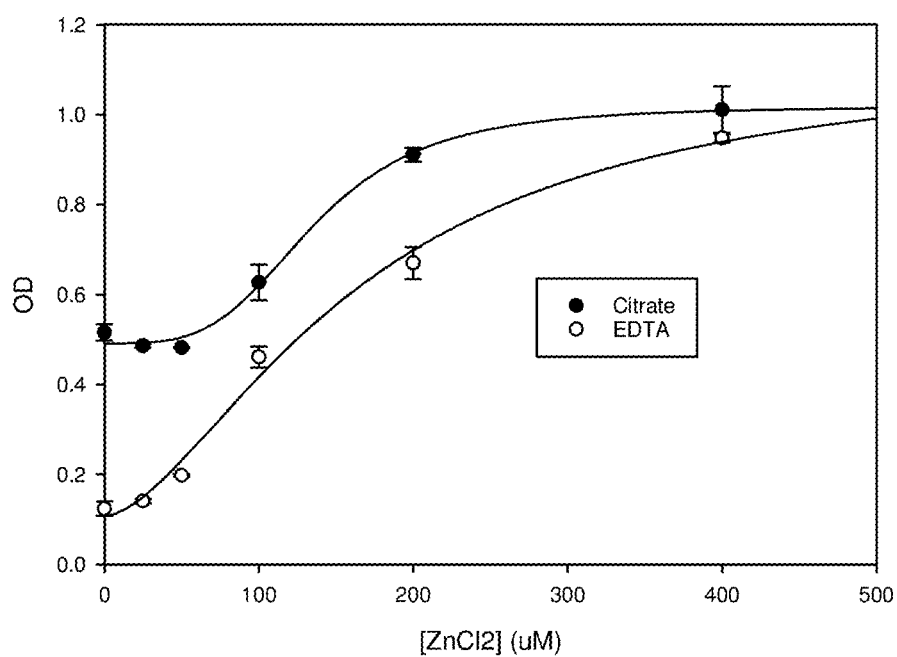
FIG. 11 is a graph showing that the addition of $ZnCl_2$ to either citrated or EDTA plasma samples increased the signal of the 2-Chain HMWK in an ELISA assay. The x-axis shows the concentration of $ZnCl_2$ in the assay well after a 40-fold dilution.

It is also evident from FIG. 10 that plasma collected from a healthy subject using EDTA as an anti-coagulant was activated similarly as citrated plasma; supporting the observation that metal ions are not required for contact system activation (Colman et al. *Blood* (1997) 90: 3819-3843). However, 2-chain HMWK was not detected by ELISA in EDTA plasma (FIG. 5B) suggesting that M004-B04 antibody binding to 2-chain HMWK is dependent upon a metal ion. A zinc binding site on HMWK in domain 5 (amino acids 479-498) of the light chain was previously identified and shown to mediate kininogen interactions with the endothelial cell surface receptors gC1qR, cytokeratin 1, and the urokinase plasminogen activator receptor and thereby enhance contact system activation (Kaplan et al. *Adv. Immunol.* (2014) 121: 41-89; Bjorkqvist et al. *Biol. Chem.* (2013) 394: 1195-1204). The addition of $ZnCl_2$ to the assay buffer was tested at various concentrations and was found to enhance binding of the antibody to cleaved HMWK (FIG. 11). Increasing concentrations of ZnCl2 on the ELISA signal observed with ellagic acid activated citrated and EDTA plasma was investigated. The ELISA signal in EDTA plasma increased to an apparent maximum at $ZnCl_2$ concentrations above 400 μM (in well concentration).

Binding of 1-chain HMWK to zinc was previously shown using electron microscopy to promote a more compact and spherical quaternary structure (Herwald et al. *Eur J. Biochem.* (2001) 268: 396-404). It was also shown by electron microscopy that 2-chain HMWK adopts a more elongated, less spherical, quaternary structure than 1-chain HMWK in a buffer containing EDTA (Herwald et al. *Eur J. Biochem.* (2001) 268: 396-404). Though the effect of zinc on the structure of 2-chain HMWK was not previously reported, the apparent zinc dependent binding of M004-B04 described herein suggests the 2-chain HMWK exists in a unique conformation in the presence of zinc.

The EDTA concentration in plasma collected in commercially available spray coated $K_2EDTA$ tubes is approximately 4 mM, which following a 1:20 dilution converts to an in-well concentration of approximately 200 μM and is consistent with the restoration of Zinc-dependent binding upon addition of sufficient $ZnCl_2$ to overwhelm the chelating capacity of EDTA. In contrast, the ELISA signal citrated plasma activated using ellagic acid was not increased in the presence of 25 or 50 μM $ZnCl_2$ (in well concentrations) but at concentrations above 100 μM $ZnCl_2$ the ELISA signal increased to a maximum above 200 μM $ZnCl_2$. (FIG. 11) The normal concentration for zinc in plasma from healthy volunteers is 10-17 μM (Wessells et al. *J. Nutr.* (2014) 144: 1204-1210). Since the ELISA signal observed in activated citrated plasma only increased when with in-well $ZnCl_2$ concentrations >50 μM, which would equates to in-plasma concentrations >1 mM, it appears that the ELISA is not susceptible to physiologic fluctuations in the concentration of zinc in the plasma. Consequently, the subsequent experiments did not add $ZnCl_2$ to the assay buffer.

As described above, the binding of 559B-M004-B04 to 2-chain HMWK was enhanced by supra-physiologic concentrations of $ZnCl_2$ and inhibited by metal chelation with high concentrations of EDTA. A zinc binding site has been described in domain of 2-chain HWMK and a synthetic peptide encompassing this site (HKH20, HKHGHGHGKHKNKGKKNGKH (SEQ ID NO: 83) was shown to inhibit contact system activation via an attenuation of cell surface association (Nakazawa et al. *Int. Immunopharmacol.* (2002) 2: 1875-1885). Consequently, the HKH20 peptide, as well as the GCP28 peptide corresponding to sequences in domain 3 were tested for their ability to inhibit 2-chain HMWK binding to 559B-M004-B04 by ELISA. As shown in FIG. 15, the HKH20 peptide but not the GCP28 peptide inhibits 2-chain HMWK binding to M004-B04, which suggests that the M004-B04 epitope could reside within domain 5 in the vicinity of the zinc binding site. To perform the assay, the kininogen peptides were diluted to 250 μg/mL and allowed to preincubate on assay plate. Then, purified 2-chain HMWK in deficient human plasma was diluted 160 and then added to plate.

Figure 8:
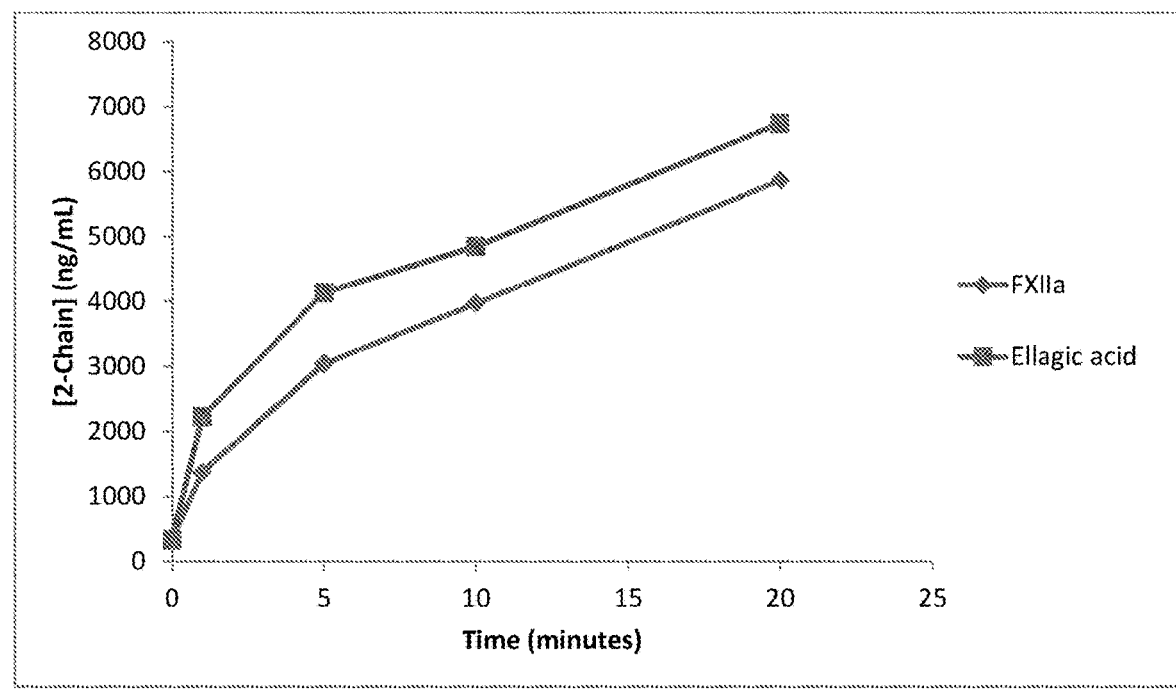
FIG. 8 is a graph showing cleaved HMWK generation at the indicated time points following contact system activation with FXIIa or ellagic acid.
Figure 9:
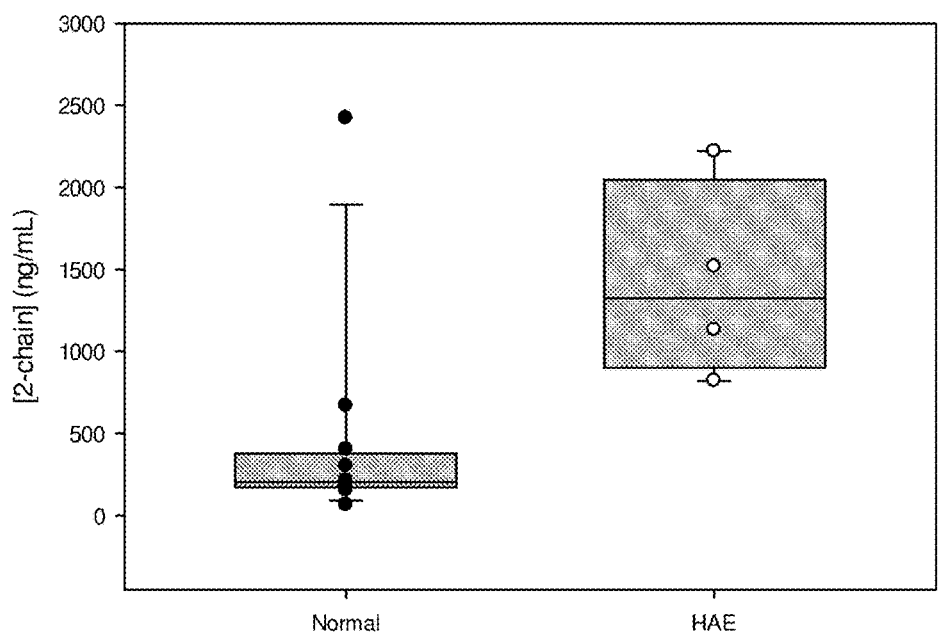
FIG. 9 is a graph showing levels of 2-chain HMWK in plasma samples from normal subjects and subjects having HAE.

Time dependence of generation of cleaved HMWK in normal citrated human plasma was assessed at various time points following activation of the contact activation system with ellagic acid or FXIIa (FIG. 8). Finally, the ELISA assay was used to assess the presence and quantity of cleaved HMWK in plasma samples from patients with hereditary angioedema (HAE) compared to citrated plasma samples from normal patients (without HAE). The samples from patients with HAE were found to contain elevated levels of 2-chain HMWK (1423±603 ng/mL) relative to samples from normal donors (432.4±186 ng/mL) (FIG. 9), which are statistically different ($P=0.017$) by one way ANOVA analysis.

Having determined that M004-B04 specifically binds a neo-epitope on 2-chain HMWK that is not present on 1-chain HMWK or LMWK and demonstrating that the antibody binding is dependent on plasma kallikrein activity, the assay was also tested using a pair of mouse monoclonal antibodies (11H05 and 13B12) for the detection (FIG. 16). Antibody 13B12 appears to bind the heavy chain of HMWK and 11H05 appears to bind the light chain of HMWK, the combination of both antibodies for detection resulted in a signal boost, possibly due to their non-overlapping binding epitopes in the antigen.

The importance of plasma collection on the assessment of contact system has been previously described (Suffritti et al.

*Clin. Exp. Allergy* (2014) 44: 1503-1514). It is well known that contact of plasma with glass or other polar surfaces results in extensive ex vivo contact system activation that can mask the accurate determination of endogenous contact system activation (Colman et al. *Blood* (1997) 90: 3819-3843). The ability of the optimized sandwich ELISA to detect 2-chain HMWK was compared in different plasma types, including a customized plasma containing a mixture of protease inhibitors in acid citrate dextrose in an evacuated, plastic blood collection tube referred to as SCAT169 (HTI, Essex Vt). As shown in FIG. 6, the standard curve prepared in SCAT169 plasma is less sensitive than the curve prepared in citrated plasma, likely due to the inclusion of 2 mM EDTA in the collected plasma. At the plasma dilution used in this assay (1:320) this concentration of EDTA (3.1 µM) does not interfere significantly with the 2-chain HMWK and may assist in stabilizing the plasma from proteolytic degradation due to metalloproteases.

Citrated and SCAT169 plasma from healthy volunteers was compared to samples from HAE patients by Western blot and the sandwich ELISA assay. In FIG. 17, panels A-C, the Western blot method of detecting 2-chain HMWK (i.e. cleaved kininogen) in citrated plasma was capable of differentiating samples from HAE patients from healthy volunteers (HV), as shown by receiver operator characteristic (ROC) analysis with an area under the curve (AUC) value of 0.977 for the comparison of basal to HV, or 1.0 for the comparison of attack to HV. Citrated plasma samples from HAE patients during quiescence (basal) were differentiated from attack samples with an AUC of 0.625 (FIG. 17, panel D).

As shown in FIG. 18, panels A-C, the Western blot method of detecting 2-chain HMWK in SCAT169 plasma was capable of differentiating samples from HAE patients from samples from healthy volunteers (HV), as shown by ROC analysis an AUC value of 0.915 for the comparison of basal to HV, or 0.967 for the comparison of attack to HV. SCAT169 samples from HAE patients during quiescence (basal) were differentiated from from attack samples with an AUC of 0.597 (FIG. 18, panel D).

In FIG. 19, panels A-C, the 2-chain ELISA method of detecting 2-chain HMWK in citrated plasma was capable of differentiating samples from HAE patients from healthy volunteers, as shown by ROC analysis with an AUC value of 0.915 for the comparison of basal to HV, or 0.866 for the comparison of attack to HV. Citrated plasma samples from HAE patients during quiescence (basal) were differentiated from from attack samples with an AUC of 0.709 (FIG. 19, panel D).

As shown in FIG. 20, panels A-C. the 2-chain ELISA method of detecting 2-chain HMWK in SCAT169 samples was capable of differentiating samples from HAE patients from healthy volunteers, as shown by ROC analysis with an AUC value of 0.999 for the comparison of basal to HV, or 1.0 for the comparison of attack to HV. Citrated plasma samples from HAE patients during quiescence (basal) were differentiated from from attack samples with an AUC of 0.8176 (FIG. 20, panel D).

For the above ROC analysis, both the 2-chain HMWK Western blot and the 2-chain HMWK ELISA demonstrated herein may be useful in differentiating patients having or at risk of having HAE based on the levels of cleaved kininogen in plasma, as compared to healthy volunteers. The presence of protease inhibitors in SCAT169 plasma reduced the ex vivo plasma activation during blood collection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. An immunoassay for determining a level of a cleaved high molecular weight kininogen (HMWK), the immunoassay comprising:
   (i) providing a support member, on which a first agent that specifically binds a cleaved HMWK is immobilized;
   (ii) contacting the support member of (i) with a biological sample suspected of containing the cleaved HMWK;
   (iii) contacting the support member obtained in (ii) with a second agent that binds HMWK, wherein the second agent is conjugated to a label; and
   (iv) detecting a signal released from the label of the second agent that is bound to the support member, to determine the level of the cleaved HMWK in the biological sample,
   wherein the first agent is an antibody comprising a heavy chain complementarity determining region (CDR) 1 sequence FSFYVMV, a heavy chain CDR2 sequence GISPSGGNTAYADSVK, and a heavy chain CDR3 sequence KLFYYDDTKGYFDF and a light chain CDR1 sequence SGSSSNIGSNYVY, a light chain CDR2 sequence RNNQRPS, and a light chain CDR3 sequence AWDDSLNGRV.

2. The immunoassay of claim 1, wherein the support member is a 96-well plate.

3. The immunoassay of claim 1, wherein, prior to step (ii), the support member of (i) is incubated with a blocking buffer.

4. The immunoassay of claim 1, wherein the second agent is a polyclonal antibody, a monoclonal antibody, or a mixture of two or more monoclonal antibodies that bind to HMWK.

5. The immunoassay of claim 1, wherein the label is a signal releasing agent, wherein the signal releasing agent is a dye or fluorophore.

6. The immunoassay of claim 1, wherein the label is a member of a receptor-ligand pair and the immunoassay further comprises, prior to step (iv), contacting the second agent in (iii) that is bound to the support member, with the other member of the receptor-ligand pair, wherein the other member is conjugated to a signal releasing agent.

7. The immunoassay of claim 6, wherein the receptor-ligand pair is biotin and streptavidin.

8. The immunoassay of claim 1, wherein the immunoassay is a Western blot assay, an enzyme-linked immunosorbent assay (ELISA), or a lateral flow assay.

9. The immunoassay of claim 1, wherein step (ii) is performed in the presence of $ZnCl_1$.

10. The immunoassay of claim 1, wherein the biological sample is obtained from a human subject.

11. The immunoassay of claim 10, wherein the biological sample is a serum sample or plasma sample, which is processed from a blood sample collected in an evacuated blood collection tube comprising one or more protease inhibitors.

12. The immunoassay of claim 10, wherein the human subject has a disease and wherein the immunoassay further comprises determining whether the disease is mediated by plasma kallikrein (pKal) based on the level of the cleaved HMWK determined in step (iv), wherein if the level of the cleaved HMWK is greater than a reference value, the disease is mediated by pKal.

13. The immunoassay of claim 10, further comprising determining whether the human subject has or is at risk for a disease mediated by pKal, wherein if the level of the cleaved HMWK is greater than a reference value, the subject is identified as having or at risk of having the disease.

14. The immunoassay of claim 13, further comprising administering to the subject an effective amount of a therapeutic agent for treating the disease, if the subject is identified as having the disease.

15. The immunoassay of claim 14, wherein the therapeutic agent is a plasma kallikrein (pKal) inhibitor, a bradykinin 2 receptor (B2R) inhibitor, and/or a C1 esterase inhibitor.

16. The immunoassay of claim 15, wherein the pKal inhibitor is an anti-pKal antibody or an inhibitory peptide.

17. The immunoassay of claim 15, wherein the therapeutic agent is lanadelumab, ecallantide, icatibant, or human plasma-derived C 1-INH.

18. The immunoassay of claim 10, wherein the human subject is on a treatment for a disease mediated by pKal, and wherein the method further comprises assessing the efficacy of the treatment based on the level of the cleaved HMWK determined in step (iv), wherein if the level of the cleaved HMWK is equal to or less than a reference value, the treatment is effective.

19. The immunoassay of claim 10, further comprising identifying a treatment for the subject based on the level of the cleaved HMWK.

20. The immunoassay of claim 10, further comprising identifying the subject as a candidate for a treatment of a disease based on the level of the cleaved HMWK.

21. The immunoassay of claim 10, wherein the human subject has one or more symptom of a disease mediated by pKal, wherein the symptom is selected from the group consisting of *Erythema marginatum*; airway blockage; abdominal cramping; vomiting; dehydration; diarrhea; pain; shock; and swelling in the arms, legs, lips, eyes, tongue, intestines and/or throat.

22. The immunoassay of claim 21, wherein the disease is hereditary angioedema (HAE).

23. The immunoassay of claim 10, wherein the human subject has one or more symptoms of hereditary angioedema (HAE), and wherein the immunoassay further comprises assessing the risk of disease attack in the subject, wherein if the level of the cleaved HMWK is greater than a reference value, there is an indication of the risk of disease attack.

24. The immunoassay of claim 23, further comprising administering a therapeutic agent to the subject, if the subject is at risk of disease attack.

25. The immunoassay of claim 1, wherein the antibody comprises a heavy chain variable domain comprising EVQLLESGGGLVQPGGSLRLS-CAASGFTFSFYVMVWVRQAPGKGLEWVS-GISPSGGNT AYADSVKGRFTISRDNSKNT-LYLQMNSLRAEDTAVYYCARKLFYYDDTKGYFDFW GQ GTLVTVSS (SEQ ID NO: 4) and a light chain variable domain that comprises comprising QYELTQPPSASGTPGQRVTLSCSGSSSNIG-SNYVYWYQQLPGTAPKLLIYRNNQRPSGVP DRFSG-SKSGTSASLAISGLQSEDEADYYCAAWDDSLNGRVF GGGTKLTVL (SEQ ID NO: 5).

26. An immunoassay for determining a level of a cleaved high molecular weight kininogen (HMWK), the immunoassay comprising:
(i) providing a support member, on which a first agent that specifically binds a cleaved HMWK is immobilized;
(ii) contacting the support member of (i) with a biological sample suspected of containing the cleaved HMWK;
(iii) contacting the support member obtained in (ii) with a second agent that binds HMWK, wherein the second agent is conjugated to a label; and
(iv) detecting a signal released from the label of the second agent that is bound to the support member to determine the level of the cleaved HMWK in the biological sample; and
wherein step (ii) is performed in the presence of $ZnCl_2$.

27. The immunoassay of claim 26, wherein the first agent is an antibody comprising a heavy chain complementarity determining region (CDR) 1 sequence FSFYVMV, a heavy chain CDR2 sequence GISPSGGNTAYADSVK, and a heavy chain CDR3 sequence KLFYYDDTKGYFDF and a light chain CDR1 sequence SGSSSNIGSNYVY, a light chain CDR2 sequence RNNQRPS, and a light chain CDR3 sequence AWDDSLNGRV.

28. The immunoassay of claim 27, wherein the antibody comprises a heavy chain variable domain comprising EVQLLESGGGLVQPGGSLRLS-CAASGFTFSFYVMVWVRQAPGKGLEWVS-GISPSGGNT AYADSVKGRFTISRDNSKNT-LYLQMNSLRAEDTAVYYCARKLFYYDDTKGYFDFW GQ GTLVTVSS (SEQ ID NO: 4) and a light chain variable domain that comprises comprising QYELTQPP-SASGTPGQRVTLSCSGSSSNIG-SNYVYWYQQLPGTAPKLLIYRNNQRPSGVP DRFSG-SKSGTSASLAISGLQSEDEADYYCAAWDDSLNGRVF GGGTKLTVL (SEQ ID NO: 5).

29. The immunoassay of claim 26, wherein the support member is a 96-well plate.

30. The immunoassay of claim 26, wherein, prior to step (ii), the support member of (i) is incubated with a blocking buffer.

31. The immunoassay of claim 26, wherein the second agent is a polyclonal antibody, a monoclonal antibody, or a mixture of two or more monoclonal antibodies that bind to HMWK.

32. The immunoassay of claim 26, wherein the label is a signal releasing agent, wherein the signal releasing agent is a dye or fluorophore.

33. The immunoassay of claim 26, wherein the label is a member of a receptor-ligand pair and the immunoassay further comprises, prior to step (iv), contacting the second agent in (iii) that is bound to the support member, with the other member of the receptor-ligand pair, wherein the other member is conjugated to a signal releasing agent.

34. The immunoassay of claim 33, wherein the receptor-ligand pair is biotin and streptavidin.

35. The immunoassay of claim 26, wherein the immunoassay is a Western blot assay, an enzyme-linked immunosorbent assay (ELISA), or a lateral flow assay.

36. The immunoassay of claim 26, wherein the biological sample is obtained from a human subject.

37. The immunoassay of claim 36, wherein the biological sample is a serum sample or plasma sample, which is processed from a blood sample collected in an evacuated blood collection tube comprising one or more protease inhibitors.

38. The immunoassay of claim 36, wherein the human subject has a disease and wherein the immunoassay further comprises determining whether the disease is mediated by plasma kallikrein (pKal) based on the level of the cleaved HMWK determined in step (iv), wherein if the level of the cleaved HMWK is greater than a reference value, the disease is mediated by pKal.

39. The immunoassay of claim 36, further comprising determining whether the human subject has or is at risk for a disease mediated by pKal, wherein if the level of the cleaved HMWK is greater than a reference value, the subject is identified as having or at risk of having the disease.

40. The immunoassay of claim 39, further comprising administering to the subject an effective amount of a therapeutic agent for treating the disease, if the subject is identified as having the disease.

41. The immunoassay of claim 40, wherein the therapeutic agent is a plasma kallikrein (pKal) inhibitor, a bradykinin 2 receptor (B2R) inhibitor, and/or a C1 esterase inhibitor.

42. The immunoassay of claim 41, wherein the pKal inhibitor is an anti-pKal antibody or an inhibitory peptide.

43. The immunoassay of claim 41, wherein the therapeutic agent is lanadelumab, ecallantide, icatibant, or human plasma-derived C1-INH.

44. The immunoassay of claim 36, wherein the human subject is on a treatment of a disease mediated by pKal, and wherein the method further comprises assessing the efficacy of the treatment based on the level of the cleaved HMWK determined in step (iv), wherein if the level of the cleaved HMWK is equal to or less than a reference value, from that of a control sample being indicative of the treatment is effective.

45. The immunoassay of claim 36, further comprising identifying a treatment for the subject based on the level of the cleaved HMWK.

46. The immunoassay of claim 36, further comprising identifying the subject as a candidate for a treatment of a disease based on the level of the cleaved HMWK.

47. The immunoassay of claim 36, wherein the human subject has one or more symptom of a disease mediated by pKal, wherein the symptom is selected from the group consisting of *Erythema marginatum*; airway blockage; abdominal cramping; vomiting; dehydration; diarrhea; pain; shock; and swelling in the arms, legs, lips, eyes, tongue, intestines and/or throat.

48. The immunoassay of claim 47, wherein the disease is hereditary angioedema (HAE).

49. The immunoassay of claim 36, wherein the human subject has one or more symptoms of hereditary angioedema (HAE), and wherein the immunoassay further comprises assessing the risk of disease attack in the subject, wherein if the level of the cleaved HMWK is greater than a reference value, there is an indication of the risk of disease attack.

50. The immunoassay of claim 49, further comprising administering a therapeutic agent to the subject, if the subject is at risk of disease attack.

* * * * *

UNITED STATES PATENT AND TRADEMARK OFFICE
CERTIFICATE OF CORRECTION

Page 1 of 1

PATENT NO. : 10,914,747 B2
APPLICATION NO. : 15/769237
DATED : February 9, 2021
INVENTOR(S) : Daniel J. Sexton et al.

It is certified that error appears in the above-identified patent and that said Letters Patent is hereby corrected as shown below:

In the Claims

Claim 21, at Column 127, beginning at Line 27, should read:
21. The immunoassay of claim 10, wherein the human subject has one or more symptom of a disease mediated by pKal, wherein the symptom is selected form the group consisting of erythema marginatum; airway blockage; abdominal cramping; vomiting; dehydration; diarrhea; pain; shock; and swelling in the arms, legs, lips, eyes, tongue, intestines and/or throat.

Signed and Sealed this
Sixth Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 83

<210> SEQ ID NO 1
<211> LENGTH: 644
<212> TYPE: PRT
<213> ORGANISM: Homo sapiens

<400> SEQUENCE: 1

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300
```

Lys Lys Ala Arg Val Gln Val Ala Gly Lys Lys Tyr Phe Ile Asp
305                 310                 315                 320

Phe Val Ala Arg Glu Thr Thr Cys Ser Lys Glu Ser Asn Glu Leu
                325                 330                 335

Thr Glu Ser Cys Glu Thr Lys Lys Leu Gly Gln Ser Leu Asp Cys Asn
            340                 345                 350

Ala Glu Val Tyr Val Pro Trp Glu Lys Lys Ile Tyr Pro Thr Val
            355                 360                 365

Asn Cys Gln Pro Leu Gly Met Ile Ser Leu Met Lys Arg Pro Pro Gly
        370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
            580                 585                 590

Ile Asp Pro Asn Gly Leu Ser Phe Asn Pro Ile Ser Asp Phe Pro Asp
    595                 600                 605

Thr Thr Ser Pro Lys Cys Pro Gly Arg Pro Trp Lys Ser Val Ser Glu
            610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 2
<211> LENGTH: 362
<212> TYPE: PRT
<213> ORGANISM: Homo sapiens

<400> SEQUENCE: 2

Gln Glu Ser Gln Ser Glu Glu Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
         35                  40                  45

Gly Ser Asp Thr Phe Tyr Ser Phe Lys Tyr Glu Ile Lys Glu Gly Asp
     50                  55                  60

Cys Pro Val Gln Ser Gly Lys Thr Trp Gln Asp Cys Glu Tyr Lys Asp
 65                  70                  75                  80

Ala Ala Lys Ala Ala Thr Gly Glu Cys Thr Ala Thr Val Gly Lys Arg
                 85                  90                  95

Ser Ser Thr Lys Phe Ser Val Ala Thr Gln Thr Cys Gln Ile Thr Pro
                100                 105                 110

Ala Glu Gly Pro Val Val Thr Ala Gln Tyr Asp Cys Leu Gly Cys Val
                115                 120                 125

His Pro Ile Ser Thr Gln Ser Pro Asp Leu Glu Pro Ile Leu Arg His
            130                 135                 140

Gly Ile Gln Tyr Phe Asn Asn Thr Gln His Ser Ser Leu Phe Met
145                 150                 155                 160

Leu Asn Glu Val Lys Arg Ala Gln Arg Gln Val Val Ala Gly Leu Asn
                165                 170                 175

Phe Arg Ile Thr Tyr Ser Ile Val Gln Thr Asn Cys Ser Lys Glu Asn
            180                 185                 190

Phe Leu Phe Leu Thr Pro Asp Cys Lys Ser Leu Trp Asn Gly Asp Thr
            195                 200                 205

Gly Glu Cys Thr Asp Asn Ala Tyr Ile Asp Ile Gln Leu Arg Ile Ala
210                 215                 220

Ser Phe Ser Gln Asn Cys Asp Ile Tyr Pro Gly Lys Asp Phe Val Gln
225                 230                 235                 240

Pro Pro Thr Lys Ile Cys Val Gly Cys Pro Arg Asp Ile Pro Thr Asn
                245                 250                 255

Ser Pro Glu Leu Glu Glu Thr Leu Thr His Thr Ile Thr Lys Leu Asn
                260                 265                 270

Ala Glu Asn Asn Ala Thr Phe Tyr Phe Lys Ile Asp Asn Val Lys Lys
            275                 280                 285

Ala Arg Val Gln Val Val Ala Gly Lys Lys Tyr Phe Ile Asp Phe Val
            290                 295                 300

Ala Arg Glu Thr Thr Cys Ser Lys Glu Ser Asn Glu Glu Leu Thr Glu
305                 310                 315                 320

Ser Cys Glu Thr Lys Lys Leu Gly Gln Ser Leu Asp Cys Asn Ala Glu
                325                 330                 335

Val Tyr Val Val Pro Trp Glu Lys Lys Ile Tyr Pro Thr Val Asn Cys
                340                 345                 350

Gln Pro Leu Gly Met Ile Ser Leu Met Lys
                355                 360

<210> SEQ ID NO 3
<211> LENGTH: 255
<212> TYPE: PRT
<213> ORGANISM: Homo sapiens

<400> SEQUENCE: 3

Ser Ser Arg Ile Gly Glu Ile Lys Glu Glu Thr Val Ser Pro Pro
1               5                   10                  15

His Thr Ser Met Ala Pro Ala Gln Asp Glu Glu Arg Asp Ser Gly Lys
                20                  25                  30

Glu Gln Gly His Thr Arg Arg His Asp Trp Gly His Glu Lys Gln Arg

```
            35                  40                  45
Lys His Asn Leu Gly His Gly His Lys His Glu Arg Asp Gln Gly His
    50                  55                  60

Gly His Gln Arg Gly His Gly Leu Gly His Gly His Glu Gln Gln His
65                  70                  75                  80

Gly Leu Gly His Gly His Lys Phe Lys Leu Asp Asp Asp Leu Glu His
                85                  90                  95

Gln Gly Gly His Val Leu Asp His Gly His Lys His Lys His Gly His
            100                 105                 110

Gly His Gly Lys His Lys Asn Lys Gly Lys Lys Asn Gly Lys His Asn
        115                 120                 125

Gly Trp Lys Thr Glu His Leu Ala Ser Ser Ser Glu Asp Ser Thr Thr
    130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
                165                 170                 175

Ser Asp Leu Ile Ala Thr Met Met Pro Pro Ile Ser Pro Ala Pro Ile
            180                 185                 190

Gln Ser Asp Asp Asp Trp Ile Pro Asp Ile Gln Ile Asp Pro Asn Gly
        195                 200                 205

Leu Ser Phe Asn Pro Ile Ser Asp Phe Pro Asp Thr Thr Ser Pro Lys
    210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
                245                 250                 255

<210> SEQ ID NO 4
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Val Met Val Trp Val Arg Gln Ala Pro Gly Lys Gly Leu Glu Trp Val
        35                  40                  45

Ser Gly Ile Ser Pro Ser Gly Gly Asn Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Leu Phe Tyr Tyr Asp Asp Thr Lys Gly Tyr Phe Asp Phe
            100                 105                 110

Trp Gly Gln Gly Thr Leu Val Thr Val Ser Ser
        115                 120

<210> SEQ ID NO 5
<211> LENGTH: 110
<212> TYPE: PRT
```

<213> ORGANISM: Artificial Sequence
<220> FEATURE:
<223> OTHER INFORMATION: Synthetic Polypeptide

<400> SEQUENCE: 5

```
Gln Tyr Glu Leu Thr Gln Pro Pro Ser Ala Ser Gly Thr Pro Gly Gln
1               5                   10                  15

Arg Val Thr Leu Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Arg Val Phe Gly Gly Gly Thr Lys Leu Thr Val Leu
            100                 105                 110
```

<210> SEQ ID NO 6
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Pro Met Val Trp Val Arg Gln Ala Pro Gly Lys Gly Leu Glu Trp Val
        35                  40                  45

Ser Ser Ile Tyr Pro Ser Gly Gly Phe Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Arg Tyr Tyr Tyr Gly Met Asp Val Trp Gly Gln
            100                 105                 110

Gly Thr Thr Val Thr Val Ser Ser
        115                 120
```

<210> SEQ ID NO 7
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 7

```
Gln Tyr Glu Leu Thr Gln Pro Pro Ser Met Ser Gly Thr Pro Gly Gln
1               5                   10                  15

Arg Val Thr Ile Ser Cys Ser Gly Ser Ser Ser Asn Ile Gly Ser Glu
            20                  25                  30

Tyr Val Tyr Trp Phe Gln Gln Leu Pro Gly Thr Ala Pro Lys Leu Leu
        35                  40                  45
```

```
Ile Tyr Arg Asn Asp Gln Arg Pro Ser Gly Val Pro Asp Arg Phe Ser
             50                  55                  60

Gly Ser Lys Ser Gly Thr Ser Ala Ser Leu Ala Ile Ser Gly Leu Arg
 65                  70                  75                  80

Ser Glu Asp Glu Thr Asp Tyr Tyr Cys Ser Trp Asp Asp Thr Leu
                 85                  90                  95

Arg Thr Gly Val Phe Gly Gly Gly Thr Lys Val Thr Val Leu
                100                 105                 110
```

<210> SEQ ID NO 8
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 8

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                 20                  25                  30

Arg Met Arg Trp Val Arg Gln Ala Pro Gly Lys Gly Leu Glu Trp Val
             35                  40                  45

Ser Gly Ile Ser Pro Ser Gly Gly Trp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Asp Asn Gly Asp Tyr Ala Leu Ala His Trp Gly Gln Gly Thr
                100                 105                 110

Leu Val Thr Val Ser Ser
            115
```

<210> SEQ ID NO 9
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 9

```
Gln Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Arg Ile Ile Asn
                 20                  25                  30

Tyr Leu Asn Trp Tyr Gln Gln Lys Pro Gly Lys Ala Pro Lys Leu Leu
             35                  40                  45

Ile Tyr Ala Ala Ser Ser Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Tyr Ser Ala Pro
                 85                  90                  95

Leu Thr Phe Gly Gly Gly Thr Arg Val Glu Ile Lys
                100                 105
```

<210> SEQ ID NO 10
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Ser Met Gly Trp Val Arg Gln Ala Pro Gly Lys Gly Leu Glu Trp Val
        35                  40                  45

Ser Ser Ile Tyr Ser Ser Gly Gly Ser Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Thr Arg Arg Gly Trp Phe Gly Glu Asp Tyr Tyr Tyr Tyr Met
            100                 105                 110

Asp Val Trp Gly Lys Gly Thr Thr Val Thr Val Ser Ser
        115                 120                 125
```

<210> SEQ ID NO 11
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 11

```
Gln Asp Ile Gln Met Thr Gln Ser Pro Ser Ser Leu Ser Ala Ser Val
1               5                   10                  15

Gly Asp Arg Ile Thr Ile Thr Cys Arg Ala Ser Gln Gly Ile Arg Asn
            20                  25                  30

Asp Val Gly Trp Tyr Gln Gln Lys Pro Gly Lys Ala Pro Gln Arg Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Leu Thr Phe Gly Gly Gly Thr Lys Val Glu Ile Lys
            100                 105
```

<210> SEQ ID NO 12
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30
```

Met Met Tyr Trp Val Arg Gln Ala Pro Gly Lys Gly Leu Glu Trp Val
            35                  40                  45

Ser Ser Ile Ser Pro Ser Gly Gly Lys Thr Trp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Ser Ser Tyr Tyr Tyr Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 13
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 13

Gln Ser Ala Leu Thr Gln Ser Pro Ser Ala Ser Gly Thr Pro Gly Gln
 1               5                  10                  15

Arg Val Thr Ile Ser Cys Ser Gly Ser Ser Ser Asn Ile Gly Gly Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Ile Tyr Tyr Cys Ala Ser Trp Asp Asp Arg Leu
                 85                  90                  95

Asn Gly His Trp Val Phe Gly Gly Gly Thr Arg Leu Thr Val Leu
            100                 105                 110

<210> SEQ ID NO 14
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 14

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Asp Met His Trp Val Arg Gln Ala Pro Gly Lys Gly Leu Glu Trp Val
        35                  40                  45

Ser Ser Ile Trp Pro Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Tyr Asp Tyr Gly Asp Phe Thr Asp Ala Phe Asp Ile

```
                    100                 105                 110
Trp Gly Gln Gly Thr Met Val Thr Val Ser Ser
            115                 120

<210> SEQ ID NO 15
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Pro Asp Arg Phe
    50                  55                  60

Ser Gly Ser Lys Ser Gly Asn Thr Ala Ser Leu Ile Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Ser Tyr Val Phe Gly Thr Gly Thr Arg Val Thr Val Leu
            100                 105                 110

<210> SEQ ID NO 16
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gln Trp Val Arg Gln Ala Pro Gly Lys Gly Leu Glu Trp Val
        35                  40                  45

Ser Trp Ile Tyr Ser Ser Gly Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Pro Gly Gln Pro Phe Asp Tyr Trp Gly Gln Gly Thr
            100                 105                 110

Leu Val Thr Val Ser Ser
            115

<210> SEQ ID NO 17
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 17
```

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Tyr Trp Tyr Gln Gln Phe Pro Gly Thr Ala Pro Lys Leu Leu
                35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Arg Leu
                85                  90                  95

Ser Gly Trp Val Phe Gly Gly Gly Thr Lys Leu Thr Val Leu
                100                 105                 110

<210> SEQ ID NO 18
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met His Trp Val Arg Gln Ala Pro Gly Lys Gly Leu Glu Trp Val
        35                  40                  45

Ser Gly Ile Tyr Ser Ser Gly Ser Thr Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His His Gly Met Asp Val Trp Gly Gln Gly Thr Thr Val
                100                 105                 110

Thr Val Ser Ser
        115

<210> SEQ ID NO 19
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 19

Gln Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Leu Ala Trp Tyr Gln Gln Lys Pro Gly Lys Ala Pro Lys Leu Leu
                35                  40                  45

Ile Tyr Ala Ala Ser Asn Leu Gln Ser Gly Val Pro Ser Arg Phe Ser
50                  55                  60

Gly Ser Gly Ser Gly Thr Asp Phe Thr Leu Thr Ile Ser Ser Leu Gln

```
                65                  70                  75                  80
Pro Glu Asp Phe Ala Thr Tyr Tyr Cys Gln Lys Tyr Asn Ile Ala Pro
                    85                  90                  95

Tyr Thr Phe Gly Gln Gly Thr Lys Leu Glu Ile Lys
                100                 105
```

<210> SEQ ID NO 20
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Thr Trp Val Arg Gln Ala Pro Gly Lys Gly Leu Glu Trp Val
        35                  40                  45

Ser Gly Ile Ser Ser Ser Gly Gly Phe Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Val Arg Gly Val Ile Lys Ala Phe Asp Ile Trp Gly Gln
            100                 105                 110

Gly Thr Met Val Thr Val Ser Ser
        115                 120
```

<210> SEQ ID NO 21
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 21

```
Gln Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser His
            20                  25                  30

Tyr Val Phe Trp Tyr Gln Gln Leu Pro Gly Ala Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asn Ser Leu
                85                  90                  95

Ser Ala Trp Val Phe Gly Gly Gly Thr Lys Leu Thr Val Leu
            100                 105                 110
```

<210> SEQ ID NO 22
<211> LENGTH: 117
<212> TYPE: PRT
<213> ORGANISM: Artificial Sequence
<220> FEATURE:

<223> OTHER INFORMATION: Synthetic Polypeptide

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Thr Met Trp Trp Val Arg Gln Ala Pro Gly Lys Gly Leu Glu Trp Val
        35                  40                  45

Ser Val Ile Ser Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ala Asn Arg Ala Phe Asp Ile Trp Gly Gln Gly Thr Met
            100                 105                 110

Val Thr Val Ser Ser
            115

<210> SEQ ID NO 23
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 23

Gln Asp Ile Gln Met Thr Gln Ser Pro Ala Ala Leu Ser Val Ser Pro
1               5                   10                  15

Gly Glu Arg Ala Thr Leu Ser Cys Arg Ala Ser Gln Ser Val Ser Ser
            20                  25                  30

Asp Leu Ala Trp Tyr Gln Gln Lys Pro Gly Gln Ala Pro Arg Leu Leu
        35                  40                  45

Ile His Gly Ala Ser Thr Arg Ala Thr Gly Ile Pro Ala Arg Phe Ser
    50                  55                  60

Gly Ser Gly Ser Gly Arg Glu Phe Thr Leu Thr Ile Ser Ser Leu Gln
65                  70                  75                  80

Ser Glu Asp Phe Ala Val Tyr Tyr Cys Gln Gln Tyr Asn Asp Trp Pro
                85                  90                  95

Pro Leu Phe Gly Pro Gly Thr Lys Val Asn Ile Lys
            100                 105

<210> SEQ ID NO 24
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met Ala Trp Val Arg Gln Ala Pro Gly Lys Gly Leu Glu Trp Val
        35                  40                  45

Ser Gly Ile Val Pro Ser Gly Gly Gln Thr Gly Tyr Ala Asp Ser Val

```
                  50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Thr Arg Arg Gly Trp Phe Gly Glu Asp Tyr Tyr Tyr Tyr Met
                100                 105                 110

Asp Val Trp Gly Lys Gly Thr Leu Val Thr Val Ser Ser
            115                 120                 125

<210> SEQ ID NO 25
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 25

Gln Asp Ile Gln Met Thr Gln Ser Pro Gly Thr Leu Ser Leu Ser Pro
  1               5                  10                  15

Gly Glu Arg Ala Thr Val Ser Cys Arg Ala Ser Gln Ser Val Gly Ser
                 20                  25                  30

Thr Tyr Leu Ala Trp Tyr Gln His Lys Pro Gly Gln Ala Pro Arg Leu
             35                  40                  45

Leu Ile Tyr Gly Ala Ser Ser Arg Ala Thr Gly Ile Pro Asp Arg Phe
         50                  55                  60

Ser Gly Ser Gly Ser Gly Thr Asp Phe Thr Leu Thr Ile Ser Ser Leu
 65                  70                  75                  80

Glu Pro Glu Asp Phe Ala Ile Tyr Tyr Cys Gln His Phe His Thr Ser
                 85                  90                  95

Pro Pro Gly Ile Thr Phe Gly Gln Gly Thr Arg Leu Glu Ile Lys
                100                 105                 110

<210> SEQ ID NO 26
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 26

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Met Tyr
                 20                  25                  30

Lys Met Ser Trp Val Arg Gln Ala Pro Gly Lys Gly Leu Glu Trp Val
             35                  40                  45

Ser Val Ile Ser Pro Ser Gly Gly Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Thr Arg Thr Ser Gly Leu Asp Tyr Trp Gly Gln Gly Thr
                100                 105                 110

Leu Val Thr Val Ser Ser
            115
```

<210> SEQ ID NO 27
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 27

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Val Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Thr Val Val Phe Gly Gly Gly Thr Lys Leu Thr Val Leu
            100                 105                 110
```

<210> SEQ ID NO 28
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Arg Trp Val Arg Gln Ala Pro Gly Lys Gly Leu Glu Trp Val
        35                  40                  45

Ser Val Ile Ser Pro Ser Gly Gly Lys Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Asp Tyr Tyr Ala Met Asp Val Trp Gly Gln Gly
            100                 105                 110

Thr Thr Val Thr Val Ser Ser
        115
```

<210> SEQ ID NO 29
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 29

```
Gln Ser Ala Leu Thr Gln Pro Pro Ser Ala Ser Gly Ala Pro Gly Gln
1               5                   10                  15

Arg Val Thr Ile Ser Cys Ser Gly Ser Ser Ser Asn Ile Gly Ser Asn
```

```
                    20                  25                  30

Thr Val Asn Trp Tyr Gln Lys Leu Pro Gly Thr Ala Pro Lys Leu Leu
                35                  40                  45

Ile Tyr Tyr Asn Asp Arg Arg Pro Ser Gly Val Pro Asp Arg Phe Ser
            50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu
            100                 105                 110

<210> SEQ ID NO 30
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Ser Trp Val Arg Gln Ala Pro Gly Lys Gly Leu Glu Trp Val
            35                  40                  45

Ser Gly Ile Ser Pro Ser Gly Lys Thr Ala Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Gly Arg Ala Val Arg Gly Lys Leu Tyr Tyr Tyr Gly
            100                 105                 110

Met Asp Val Trp Gly Gln Gly Thr Thr Val Thr Val Ser Ser
        115                 120                 125

<210> SEQ ID NO 31
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 31

Gln Ser Ala Leu Thr Gln Pro Pro Ser Ala Ser Gln Thr Pro Gly Gln
1               5                   10                  15

Thr Val Thr Ile Ser Cys Ser Gly Ser Ser Ser Asn Ile Gly Thr Asn
                20                  25                  30

Asn Val Asn Trp Tyr Gln Gln Leu Pro Gly Thr Ala Pro Lys Leu Leu
            35                  40                  45

Ile Ser Ser His His Arg Arg Pro Ser Gly Val Pro Asp Arg Phe Ser
        50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95
```

Asn Gly Pro Val Phe Gly Gly Thr Lys Leu Thr Val Leu
            100                 105                 110

<210> SEQ ID NO 32
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

His Met Asn Trp Val Arg Gln Ala Pro Gly Lys Gly Leu Glu Trp Val
        35                  40                  45

Ser Ser Ile Tyr Ser Ser Gly Gly Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Arg Tyr Gly Met Asp Val Trp Gly Gln Gly Thr Thr
            100                 105                 110

Val Thr Val Ser Ser
        115

<210> SEQ ID NO 33
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 33

Gln Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Asn Ser Phe Pro
                85                  90                  95

Ile Thr Phe Gly Gln Gly Thr Arg Leu Glu Ile Lys
            100                 105

<210> SEQ ID NO 34
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 34

Glu Val Gln Leu Leu Glu Ser Gly Gly Gly Leu Val Gln Pro Gly Gly

```
            1               5                  10                  15
         Ser Leu Arg Leu Ser Cys Ala Ala Ser Gly Phe Thr Phe Ser Met Tyr
                     20                  25                  30

Asp Met His Trp Val Arg Gln Ala Pro Gly Lys Gly Leu Glu Trp Val
                     35                  40                  45

Ser Ser Ile Ser Ser Gly Gly Tyr Thr Gln Tyr Ala Asp Ser Val
                     50                  55                  60

Lys Gly Arg Phe Thr Ile Ser Arg Asp Asn Ser Lys Asn Thr Leu Tyr
          65                  70                  75                  80

Leu Gln Met Asn Ser Leu Arg Ala Glu Asp Thr Ala Met Tyr Tyr Cys
                         85                  90                  95

Ala Arg Asp Arg Gly Leu Ile Ala Ala Gly Gly Phe Asp Pro Trp
                         100                 105                 110

Gly Gln Gly Thr Leu Val Thr Val Ser Ser
                         115                 120
```

<210> SEQ ID NO 35
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 35

```
         Gln Asp Ile Gln Met Thr Gln Ser Pro Ser Ser Leu Ser Ala Ser Val
          1               5                  10                  15

Gly Asp Arg Val Thr Ile Thr Cys Arg Ala Ser Gln Ser Ile Gly Ile
                     20                  25                  30

Tyr Leu Asn Trp Tyr Gln Gln Lys Pro Gly Thr Ala Pro Lys Leu Leu
                     35                  40                  45

Ile Tyr Ala Ala Ser Ser Leu Gln Ser Gly Val Pro Ser Arg Phe Thr
                     50                  55                  60

Gly Ser Gly Ser Gly Thr Asp Phe Thr Leu Thr Ile Ser Ser Leu Gln
          65                  70                  75                  80

Pro Asp Asp Phe Ala Thr Tyr Tyr Cys Gln Arg Thr Tyr Gly Arg Pro
                         85                  90                  95

Leu Thr Phe Gly Gly Gly Thr Lys Val Glu Ile Lys
                         100                 105
```

<210> SEQ ID NO 36
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 36

```
         Glu Val Gln Leu Leu Glu Ser Gly Gly Gly Leu Val Gln Pro Gly Gly
          1               5                  10                  15

Ser Leu Arg Leu Ser Cys Ala Ala Ser Gly Phe Thr Phe Ser Lys Tyr
                     20                  25                  30

Glu Met Met Trp Val Arg Gln Ala Pro Gly Lys Gly Leu Glu Trp Val
                     35                  40                  45

Ser Ser Ile Ser Pro Ser Gly Gly Tyr Thr Met Tyr Ala Asp Ser Val
                     50                  55                  60

Lys Gly Arg Phe Thr Ile Ser Arg Asp Asn Ser Lys Asn Thr Leu Tyr
          65                  70                  75                  80
```

Leu Gln Met Asn Ser Leu Arg Ala Glu Asp Thr Ala Val Tyr Tyr Cys
            85                  90                  95

Ala Arg His Arg Ser Lys Trp Asn Asp Ala Pro Phe Asp Ser Trp Gly
            100                 105                 110

Gln Gly Thr Leu Val Thr Val Ser Ser
        115                 120

<210> SEQ ID NO 37
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 37

Gln Asp Ile Gln Met Thr Gln Ser Pro Ser Ser Leu Ser Ala Ser Val
1               5                   10                  15

Gly Asp Arg Val Ala Ile Thr Cys Arg Ala Ser Gln Ser Ile Asp Thr
            20                  25                  30

Tyr Leu Asn Trp Tyr Gln Gln Lys Pro Gly Lys Ala Pro Lys Leu Leu
        35                  40                  45

Ile Tyr Ala Ala Ser Lys Leu Glu Asp Gly Val Pro Ser Arg Phe Ser
    50                  55                  60

Gly Ser Gly Thr Gly Thr Asp Phe Thr Leu Thr Ile Arg Ser Leu Gln
65                  70                  75                  80

Pro Glu Asp Phe Ala Ser Tyr Phe Cys Gln Gln Ser Tyr Ser Pro
                85                  90                  95

Gly Ile Thr Phe Gly Pro Gly Thr Lys Val Glu Ile Lys
            100                 105

<210> SEQ ID NO 38
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Gln Met Tyr Trp Val Arg Gln Ala Pro Gly Lys Gly Leu Glu Trp Val
        35                  40                  45

Ser Ser Ile Tyr Ser Ser Gly Arg Thr Phe Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Thr Arg Gly Ser Trp Tyr Val Gly Gly Asn Glu Tyr Phe Gln His
            100                 105                 110

Trp Gly Gln Gly Thr Leu Val Thr Val Ser Ser
        115                 120

<210> SEQ ID NO 39
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 39

Gln Ser Val Leu Thr Gln Ser Pro Ser Leu Ser Leu Ser Pro Gly Gln
1               5                   10                  15

Thr Ala Ser Ile Pro Cys Ser Gly Asp Thr Leu Gly Asn Lys Phe Val
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Thr Gly Thr Gln Ala Met
65                  70                  75                  80

Asp Glu Ala Asp Tyr Tyr Cys Gln Val Trp Asp Ser Asn Ser Tyr Ala
                85                  90                  95

Phe Gly Pro Gly Thr Lys Val Thr Val Leu
            100                 105

<210> SEQ ID NO 40
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Met Met Tyr Trp Val Arg Gln Ala Pro Gly Lys Gly Leu Glu Trp Val
        35                  40                  45

Ser Ser Ile Ser Ser Ser Gly Gly Phe Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Leu Ala Val Ala Ala Pro Asp Tyr Trp Gly Gln
            100                 105                 110

Gly Thr Leu Val Thr Val Ser Ser
        115                 120

<210> SEQ ID NO 41
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 41

Gln Ser Glu Leu Thr Gln Pro Ala Ser Val Ser Gly Ser Pro Gly Gln
1               5                   10                  15

Ser Ile Thr Ile Ser Cys Ile Gly Thr Ser Ser Asp Ile Gly Thr Tyr
            20                  25                  30

Asn Tyr Val Ser Trp Tyr Gln Gln His Pro Gly Lys Ala Pro Lys Leu
        35                  40                  45

```
Met Ile Tyr Asp Val Asn Thr Arg Pro Ser Gly Val Ser Asp Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                85                  90                  95

Val Thr Trp Val Phe Gly Gly Gly Thr Thr Leu Thr Val Leu
                100                 105                 110
```

<210> SEQ ID NO 42
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 42

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
                20                  25                  30

Asn Met Tyr Trp Val Arg Gln Ala Pro Gly Lys Gly Leu Glu Trp Val
                35                  40                  45

Ser Arg Ile Ser Pro Ser Gly Gly Trp Thr Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gly Gln Trp Met Asp Trp Trp Gly Gln Gly Thr Met Val Thr
                100                 105                 110

Val Ser Ser
        115
```

<210> SEQ ID NO 43
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 43

```
Gln Asp Ile Gln Met Thr Gln Ser Pro Ser Ser Leu Ser Ala Ser Val
 1               5                  10                  15

Gly Asp Arg Val Ile Ile Thr Cys Arg Ala Ser Gln Asn Ile Thr Gly
                20                  25                  30

Tyr Leu Asn Trp Tyr Gln Gln Lys Pro Gly Lys Ala Pro Asn Leu Leu
                35                  40                  45

Ile Tyr Asp Ala Ser Arg Met Asn Thr Gly Val Pro Ser Arg Phe Arg
 50                  55                  60

Gly Ser Gly Ser Gly Thr Asp Tyr Ile Leu Thr Ile Tyr Lys Leu Glu
 65                  70                  75                  80

Pro Glu Asp Ile Gly Thr Tyr Phe Cys Gln His Thr Asp Asp Phe Ser
                85                  90                  95

Val Thr Phe Gly Gly Gly Thr Lys Val Asp Leu Lys
                100                 105
```

<210> SEQ ID NO 44

```
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Tyr Arg
            20                  25                  30

Met Met Trp Val Arg Gln Ala Pro Gly Lys Gly Leu Glu Trp Val Ser
        35                  40                  45

Tyr Ile Ser Ser Ser Gly Gly Tyr Thr Ala Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Lys Arg Asn Arg Ala Phe Asp Ile Trp Gly Gln Gly Thr Met Val
            100                 105                 110

Thr Val Ser Ser
        115

<210> SEQ ID NO 45
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 45

Gln Asp Ile Gln Met Thr Gln Ser Pro Asp Ser Leu Ala Val Ser Leu
1               5                   10                  15

Gly Glu Arg Ala Thr Ile Asn Cys Lys Ser Ser Gln Ser Val Leu Tyr
            20                  25                  30

Ser Ser Asn Asn Lys Asn Tyr Leu Ala Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

Val Pro Asp Arg Phe Ser Gly Ser Gly Ser Gly Thr Asp Phe Thr Leu
65                  70                  75                  80

Thr Ile Ser Ser Leu Gln Ala Glu Asp Val Ala Val Tyr Tyr Cys Gln
                85                  90                  95

Gln Tyr Tyr Ser Thr Pro Leu Gly Phe Gly Gln Gly Thr Lys Leu Glu
            100                 105                 110

Ile Lys

<210> SEQ ID NO 46
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
```

```
                 20                  25                  30
Gln Met Thr Trp Val Arg Gln Ala Pro Gly Lys Gly Leu Glu Trp Val
                 35                  40                  45

Ser Ser Ile Gly Ser Ser Gly Gly Phe Thr Asn Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Ala Asn Phe Tyr Tyr Met Asp Val Trp Gly Lys
                100                 105                 110

Gly Thr Thr Val Thr Val Ser Ser
                115                 120

<210> SEQ ID NO 47
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 47

Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asn Ile Tyr Ser
                 20                  25                  30

Phe Leu Asn Trp Tyr Gln Gln Lys Pro Gly Lys Ala Pro Lys Leu Leu
                 35                  40                  45

Ile Tyr Ala Thr Ser Ser Leu Gln Ser Gly Val Pro Ser Arg Phe Ser
                 50                  55                  60

Gly Ser Gly Ser Gly Thr Asp Phe Thr Leu Thr Ile Ser Ser Leu Gln
 65                  70                  75                  80

Pro Glu Asp Phe Ala Ser Tyr Tyr Cys Gln Gln Asn Tyr Asn Ile Pro
                 85                  90                  95

Trp Thr Phe Gly Gln Gly Thr Lys Val Glu Ile Lys
                100                 105

<210> SEQ ID NO 48
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                 20                  25                  30

Met Met Lys Trp Val Arg Gln Ala Pro Gly Lys Gly Leu Glu Trp Val
                 35                  40                  45

Ser Ser Ile Val Pro Ser Gly Gly Trp Thr Thr Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Thr Glu Gly Asn Leu Trp Phe Gly Gly Arg Ala Phe Asp Ile
            100                 105                 110

Trp Gly Gln Gly Thr Met Val Thr Val Ser Ser
        115                 120

<210> SEQ ID NO 49
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 49

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Arg Ser Asn Trp
                85                  90                  95

Pro Pro Ser Phe Gly Gln Gly Thr Arg Leu Asp Ile Lys
            100                 105

<210> SEQ ID NO 50
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met His Trp Val Arg Gln Ala Pro Gly Lys Gly Leu Glu Trp Val
        35                  40                  45

Ser Arg Ile Ser Ser Ser Gly Gly Lys Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Arg Tyr Cys Thr Ala Asn Thr Cys Ser Leu Tyr Gly
            100                 105                 110

Met Asp Val Trp Gly Arg Gly Thr Thr Val Thr Val Ser Ser
        115                 120                 125

<210> SEQ ID NO 51
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 51

Gln Asp Ile Gln Met Thr Gln Ser Pro Ser Ser Leu Ser Ala Ser Val
1               5                   10                  15

Gly Asp Arg Val Ala Ile Thr Cys Arg Thr Ser Gln Gly Val Arg Ser
            20                  25                  30

Asp Phe Ala Trp Tyr Gln Gln Thr Pro Gly Lys Ala Pro Arg Arg Leu
        35                  40                  45

Ile Tyr Ala Ala Phe Ile Leu Asp Asn Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Leu Thr Phe Gly Gly Gly Thr Lys Val Glu Met Lys
            100                 105

<210> SEQ ID NO 52
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met His Trp Val Arg Gln Ala Pro Gly Lys Gly Leu Glu Trp Val
        35                  40                  45

Ser Val Ile Ser Pro Ser Gly Gly Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Gly Ser Gly Ser His Glu Asp Tyr Trp Gly Gln
            100                 105                 110

Gly Thr Leu Val Thr Val Ser Ser
        115                 120

<210> SEQ ID NO 53
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 53

Gln Asp Ile Gln Met Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Gly Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Phe Cys Gln Gln Tyr Lys Asn Trp Pro
                85                  90                  95

Asn Leu Thr Phe Gly Gly Gly Thr Lys Val Asp Ile Lys
            100                 105

<210> SEQ ID NO 54
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Pro Met Ala Trp Val Arg Gln Ala Pro Gly Lys Gly Leu Glu Trp Val
        35                  40                  45

Ser Gly Ile Val Ser Ser Gly Arg Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Asp Phe Trp Ser Glu Gly Ala Phe Asp Ile Trp
            100                 105                 110

Gly Gln Gly Thr Met Val Thr Val Ser Ser
        115                 120

<210> SEQ ID NO 55
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Phe Val Tyr Trp Tyr His Gln Val Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Ala Ala Ser Ala Ser Leu Ala Ile Ser Gly Leu Arg
65                  70                  75                  80

Ser Glu Asp Glu Ala Asp Tyr Tyr Cys Ala Ala Trp Asp Asn Ser Leu
                85                  90                  95

Ser Gly Phe Tyr Val Phe Gly Ala Gly Thr Lys Val Thr Val Leu
            100                 105                 110

<210> SEQ ID NO 56
<211> LENGTH: 120
<212> TYPE: PRT
<213> ORGANISM: Artificial Sequence

```
<220> FEATURE:
<223> OTHER INFORMATION: Synthetic Polypeptide

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gly Met His Trp Val Arg Gln Ala Pro Gly Lys Gly Leu Glu Trp Val
        35                  40                  45

Ser Arg Ile Gly Pro Ser Gly Gly Pro Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Gly Thr Gly Arg Tyr Phe Gln His Trp Gly Gln
            100                 105                 110

Gly Thr Leu Val Thr Val Ser Ser
        115                 120

<210> SEQ ID NO 57
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 57

Gln Asp Ile Gln Met Thr Gln Ser Pro Asp Ser Leu Ser Leu Ser Pro
1               5                   10                  15

Gly Asp Arg Ala Thr Leu Ser Cys Arg Ala Ser Gln Ser Val Gly Ser
            20                  25                  30

Asp Tyr Leu Ala Trp Tyr Gln Gln Lys Pro Gly Gln Ala Pro Arg Leu
        35                  40                  45

Leu Ile Tyr Asp Ala Ser Asn Arg Ala Thr Gly Ile Pro Ala Arg Phe
    50                  55                  60

Ser Gly Ser Gly Ser Gly Thr Asp Phe Thr Leu Thr Ile Ser Ser Leu
65                  70                  75                  80

Glu Pro Glu Asp Phe Ala Val Tyr Tyr Cys Gln Gln Arg Ser Asn Trp
                85                  90                  95

Pro Pro Thr Phe Gly Gly Gly Thr Lys Val Glu Ile Lys
            100                 105

<210> SEQ ID NO 58
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Arg Trp Val Arg Gln Ala Pro Gly Lys Gly Leu Glu Trp Val
        35                  40                  45
```

```
Ser Tyr Ile Ser Ser Gly Gly Glu Thr Met Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Gly Tyr Gly Arg Ile Asp Tyr Trp Gly Gln Gly Thr Leu Val
            100                 105                 110

Thr Val Ser Ser
        115
```

<210> SEQ ID NO 59
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 59

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Gly
                 85                  90                  95

Ser Thr Arg Val Phe Gly Thr Gly Thr Arg Val Thr Val Leu
            100                 105                 110
```

<210> SEQ ID NO 60
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 60

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Val Met Arg Trp Val Arg Gln Ala Pro Gly Lys Gly Leu Glu Trp Val
        35                  40                  45

Ser Ser Ile Gly Ser Ser Gly Gly Pro Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Gly Ser Gly Ser Ser His Ala Phe Asp Ile Trp Gly
            100                 105                 110

Gln Gly Thr Met Val Thr Val Ser Ser
        115                 120
```

<210> SEQ ID NO 61
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 61

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ser Gly Thr Tyr Tyr Cys Gln Gln Tyr Asn Ser Phe Pro
                85                  90                  95

Leu Thr Phe Gly Gly Gly Thr Lys Val Glu Ile Lys
            100                 105
```

<210> SEQ ID NO 62
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Val Ile Ser Pro Ser Gly Gly Leu Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Thr Gly Phe Ala Val Gln His Gly Gly Gly Ala Phe Asp Ile Trp
            100                 105                 110

Gly Gln Gly Thr Met Val Thr Val Ser Ser
        115                 120
```

<210> SEQ ID NO 63
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 63

```
Gln Asp Ile Gln Met Thr Gln Ser Pro Ala Thr Leu Ser Met Ser Pro
1               5                   10                  15
```

```
Gly Glu Arg Ala Thr Leu Ser Cys Arg Ala Ser Gln Ser Val Thr Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ile Arg Ala Thr Gly Val Pro Ala Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Arg Thr Ile Trp Pro
                85                  90                  95

Leu Thr Phe Gly Gly Gly Thr Lys Val Glu Ile Lys
            100                 105
```

<210> SEQ ID NO 64
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 64

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Tyr
            20                  25                  30

Glu Met Val Trp Val Arg Gln Ala Pro Gly Lys Gly Leu Glu Trp Val
        35                  40                  45

Ser Ser Ile Val Pro Ser Gly Gly Trp Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Pro Ser Gly Arg Gly Leu Ala Phe Asp Ile Trp Gly Gln Gly
            100                 105                 110

Thr Met Val Thr Val Ser Ser
        115
```

<210> SEQ ID NO 65
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 65

```
Gln Asp Ile Gln Met Thr Gln Ser Pro Gly Thr Leu Ser Leu Ser Pro
 1               5                  10                  15

Gly Glu Arg Ala Thr Leu Ser Cys Arg Ala Ser Gln Ser Ile Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Arg Ala Thr Gly Val Pro Asp Arg Phe
 50                  55                  60

Ser Gly Ser Gly Ser Gly Thr Glu Phe Thr Leu Thr Ile Ser Ser Leu
 65                  70                  75                  80

Gln Pro Glu Asp Phe Ala Thr Tyr Tyr Cys Leu Gln Gln Lys Ser Tyr
                85                  90                  95
```

```
Pro Tyr Thr Phe Gly Gln Gly Thr Lys Val Glu Ile Lys
            100                 105
```

<210> SEQ ID NO 66
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 66

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Phe Met Thr Trp Val Arg Gln Ala Pro Gly Lys Gly Leu Glu Trp Val
            35                  40                  45

Ser Trp Ile Ser Ser Ser Gly Gly Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Ala Tyr Tyr Tyr Asp Ala Phe Asp Ile Trp Gly Gln Gly
            100                 105                 110

Thr Met Val Thr Val Ser Ser
        115
```

<210> SEQ ID NO 67
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 67

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ala Ile
            20                  25                  30

Phe Leu Asn Trp Tyr Gln Gln Thr Pro Gly Lys Pro Pro Lys Leu Leu
            35                  40                  45

Ile Tyr Gly Ala Ser Thr Leu Gln Ser Gly Val Pro Ser Arg Phe Ser
    50                  55                  60

Gly Ser Gly Ser Gly Ala Asp Phe Thr Leu Thr Ile Ser Asn Leu Gln
65                  70                  75                  80

Leu Glu Asp Phe Thr Thr Tyr Tyr Cys Gln Gln Ser Tyr Ser Thr Leu
            85                  90                  95

Tyr Thr Phe Gly Gln Gly Thr Lys Leu Glu Ile Lys
            100                 105
```

<210> SEQ ID NO 68
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Trp Val
        35                  40                  45

Ser Val Ile Ser Ser Gly Gly Met Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Tyr Tyr Gly Asn Met Asp Val Trp Gly Lys Gly Thr Thr
                100                 105                 110

Val Thr Val Ser Ser
        115
```

<210> SEQ ID NO 69
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 69

```
Gln Asp Ile Gln Met Thr Gln Ser Pro Ser Ser Leu Ser Thr Ser Val
1               5                   10                  15

Gly Asp Arg Val Thr Ile Thr Cys Arg Thr Ser Gln Asp Ile Ser Gly
            20                  25                  30

Ala Leu Ala Trp Tyr Gln Gln Lys Pro Gly Lys Ala Pro Arg Leu Leu
        35                  40                  45

Ile Phe Gly Ala Ser Ser Leu Glu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Phe Asn Lys Tyr Pro
                85                  90                  95

Leu Thr Phe Gly Gly Gly Thr Lys Val Glu Ile Lys
                100                 105
```

<210> SEQ ID NO 70
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Thr Met Gly Trp Val Arg Gln Ala Pro Gly Lys Gly Leu Glu Trp Val
        35                  40                  45

Ser Tyr Ile Tyr Pro Ser Gly Gly Tyr Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Asn Pro Tyr Ser Ser Gly Gly Tyr Trp Gly Gln Gly Thr Leu Val
            100                 105                 110

Thr Val Ser Ser
        115

<210> SEQ ID NO 71
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 71

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Asp
            20                  25                  30

Ser Asn Gly Tyr Asn Tyr Leu Asp Trp Phe Leu Gln Lys Pro Gly Gln
        35                  40                  45

Ser Pro Gln Leu Leu Ile Tyr Leu Gly Phe Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro Tyr Thr Phe Gly Gln Gly Thr Lys Leu Glu Ile
            100                 105                 110

Thr

<210> SEQ ID NO 72
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Leu Met Thr Trp Val Arg Gln Ala Pro Gly Lys Gly Leu Glu Trp Val
        35                  40                  45

Ser Gly Ile Ser Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Pro Asn Trp Ile Tyr Gly Met Asp Val Trp Gly Gln
            100                 105                 110

Gly Thr Thr Val Thr Val Ser Ser
        115                 120

<210> SEQ ID NO 73
```

```
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 73

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Tyr Ala
            20                  25                  30

Ser Trp Tyr Gln Gln Lys Pro Gly Gln Ser Pro Val Leu Val Ile Tyr
        35                  40                  45

Gln Asp Arg Arg Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Gly Val Val Phe
                85                  90                  95

Gly Gly Gly Thr Lys Leu Thr Val Leu
            100                 105

<210> SEQ ID NO 74
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Leu Trp Val Arg Gln Ala Pro Gly Lys Gly Leu Glu Trp Val
        35                  40                  45

Ser Gly Ile Ser Pro Ser Gly Gly Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Val Ala Tyr Ser Gly Ser Tyr Tyr Tyr Tyr Tyr Met Asp
            100                 105                 110

Val Trp Gly Lys Gly Thr Thr Val Thr Val Ser Ser
        115                 120

<210> SEQ ID NO 75
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 75

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30
```

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Tyr Ser Thr His
                 85                  90                  95

Ser Ile Thr Phe Gly Gln Gly Thr Arg Leu Glu Ile Lys
            100                 105

<210> SEQ ID NO 76
<211> LENGTH: 137
<212> TYPE: PRT
<213> ORGANISM: Artificial Sequence
<220> FEATURE:
<223> OTHER INFORMATION: Synthetic Polypeptide

<400> SEQUENCE: 76

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
            20                  25                  30

Ile Met Gly Trp Val Arg Gln Ala Pro Gly Lys Gly Leu Glu Trp Val
        35                  40                  45

Ser Ser Ile Gly Ser Ser Gly Val Thr Val Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Gly Val Thr Val Leu His Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser
    130                 135

<210> SEQ ID NO 77
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 77

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Val Pro Lys Leu
        35                  40                  45

Ile Ile Tyr Glu Gly Asn Lys Arg Pro Ser Gly Val Pro Asp Arg Phe
 50                  55                  60

Ser Gly Ser Lys Ala Gly Asn Thr Ala Ser Leu Thr Val Ser Gly Leu
 65                  70                  75                  80

Gln Ala Glu Asp Glu Ala Asp Tyr Tyr Cys Thr Ala Tyr Gly Gly His
                 85                  90                  95

Ser Arg Phe Tyr Val Phe Gly Thr Gly Thr Lys Val Thr Val Leu Gly
            100                 105                 110

Gln Pro Lys Ala Asn Pro
        115

<210> SEQ ID NO 78
<211> LENGTH: 304
<212> TYPE: PRT
<213> ORGANISM: Homo sapiens

<400> SEQUENCE: 78

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
            35                  40                  45

Leu Met His Ser Phe Cys Ala Phe Lys Ala Asp Asp Gly Pro Cys Lys
        50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
            115                 120                 125

Glu Asp Pro Gly Ile Cys Arg Gly Tyr Ile Thr Arg Tyr Phe Tyr Asn
        130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300

<210> SEQ ID NO 79
<211> LENGTH: 58
<212> TYPE: PRT
<213> ORGANISM: Homo sapiens

<400> SEQUENCE: 79

```
Arg Pro Asp Phe Cys Leu Glu Pro Tyr Thr Gly Pro Cys Lys Ala
1               5                   10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
    50                  55
```

<210> SEQ ID NO 80
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 80

```
Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
                20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
    50                  55                  60
```

<210> SEQ ID NO 81
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Ile Met Met Trp Val Arg Gln Ala Pro Gly Lys Gly Leu Glu Trp Val
            35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
            115                 120
```

<210> SEQ ID NO 82
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 82

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile
                100                 105

<210> SEQ ID NO 83
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 83

His Lys His Gly His Gly His Gly Lys His Lys Asn Lys Gly Lys Lys
1               5                   10                  15

Asn Gly Lys His
            20
```